US012208106B2

(12) United States Patent
Melnick et al.

(10) Patent No.: US 12,208,106 B2
(45) Date of Patent: Jan. 28, 2025

(54) METHODS OF VITAMIN D TREATMENT

(71) Applicant: EIRGEN PHARMA LTD., Waterford (IE)

(72) Inventors: Joel Z. Melnick, Evanston, IL (US); Charles W. Bishop, Miami, FL (US); P. Martin Petkovich, Kingston (CA); Stephen A. Strugnell, Madison, WI (US)

(73) Assignee: EIRGEN PHARMA LTD., Waterford (IE)

( * ) Notice: Subject to any disclaimer, the term of this patent is extended or adjusted under 35 U.S.C. 154(b) by 63 days.

(21) Appl. No.: 17/498,496

(22) Filed: Oct. 11, 2021

(65) Prior Publication Data

US 2022/0062304 A1 Mar. 3, 2022

Related U.S. Application Data

(63) Continuation of application No. 16/089,235, filed as application No. PCT/EP2017/057282 on Mar. 28, 2017, now Pat. No. 11,173,168.

(60) Provisional application No. 62/314,359, filed on Mar. 28, 2016.

(51) Int. Cl.
*A61K 31/593* (2006.01)
*A61K 9/00* (2006.01)
*A61K 31/592* (2006.01)
*A61P 3/02* (2006.01)
*A61P 13/12* (2006.01)

(52) U.S. Cl.
CPC .......... *A61K 31/593* (2013.01); *A61K 9/0053* (2013.01); *A61K 31/592* (2013.01); *A61P 3/02* (2018.01); *A61P 13/12* (2018.01)

(58) Field of Classification Search
CPC ........... A61K 31/593; A61P 3/02; A61P 13/12
See application file for complete search history.

(56) References Cited

U.S. PATENT DOCUMENTS

| | | |
|---|---|---|
| 3,565,924 A | 2/1971 | DeLuca et al. |
| 3,833,622 A | 9/1974 | Babcock et al. |
| 3,880,894 A | 4/1975 | De Luca et al. |
| 3,974,272 A | 8/1976 | Polli et al. |
| 4,004,003 A | 1/1977 | Babcock et al. |
| 4,230,701 A | 10/1980 | Holick et al. |
| 4,335,120 A | 6/1982 | Holick et al. |
| 4,442,093 A | 4/1984 | Maeda et al. |
| 4,448,721 A | 5/1984 | DeLuca et al. |
| 4,555,364 A | 11/1985 | DeLuca et al. |
| 4,668,517 A | 5/1987 | Weber et al. |
| 4,684,524 A | 8/1987 | Eckenhoff et al. |
| 4,695,591 A | 9/1987 | Hanna et al. |
| 4,721,613 A | 1/1988 | Urquhart et al. |
| 4,729,895 A | 3/1988 | Makino et al. |
| 4,755,544 A | 7/1988 | Makino et al. |
| 4,892,821 A | 1/1990 | Omura et al. |
| 4,997,824 A | 3/1991 | Popovtzer et al. |
| 5,026,559 A | 6/1991 | Eichel et al. |
| 5,160,742 A | 11/1992 | Mazer et al. |
| 5,167,965 A | 12/1992 | Schulz |
| 5,328,903 A | 7/1994 | Ishii et al. |
| 5,342,626 A | 8/1994 | Winston, Jr. et al. |
| 5,354,743 A | 10/1994 | Thys-Jacobs |
| 5,403,831 A | 4/1995 | DeLuca et al. |
| 5,431,917 A | 7/1995 | Yamamoto et al. |
| 5,472,712 A | 12/1995 | Oshlack et al. |
| 5,487,900 A | 1/1996 | Itoh et al. |
| 5,529,991 A | 6/1996 | Knutson et al. |
| 5,593,690 A | 1/1997 | Akiyama et al. |
| 5,602,116 A | 2/1997 | Knutson et al. |
| 5,614,513 A | 3/1997 | Knutson et al. |
| 5,622,941 A | 4/1997 | Knutson et al. |
| 5,693,615 A | 12/1997 | Stone |
| 5,707,980 A | 1/1998 | Knutson et al. |
| 5,756,123 A | 5/1998 | Yamamoto et al. |
| 5,783,215 A | 7/1998 | Arwidsson et al. |
| 5,795,882 A | 8/1998 | Bishop et al. |
| 5,861,386 A | 1/1999 | Knutson et al. |
| 5,869,473 A | 2/1999 | Knutson et al. |
| 5,872,113 A | 2/1999 | Nestor, Jr. et al. |
| 5,888,994 A | 3/1999 | Hennessy et al. |
| 5,919,986 A | 7/1999 | Barbier et al. |

(Continued)

FOREIGN PATENT DOCUMENTS

| | | |
|---|---|---|
| CA | 2241205 A1 | 7/1997 |
| CN | 101668517 A | 3/2010 |

(Continued)

OTHER PUBLICATIONS

Rhee et al. Semin. Dial., Nov. 2013, vol. 26, No. 6, pp. 1-14 (Year: 2013).*
Hidroferol® (calcifediol): Casos de Hipercalcemia e Hipervitaminosis D, Butlletí de Farmacovigilància de Catalunya, 9(5):17-20 (2011).
K/DOQI Clinical Practice Guidelines for Bone Metabolism and Disease in Chronic Kidney Disease, National Kidney Foundation, Am. J. Kidney Dis., 42 (Supplement 3):1-202 (2003).
9 Things That Can Undermine Your Vitamin D Level: Don't Let Your Vitamin D Absorption Slip Away, Harvard Health Publishing, downloaded from the Internet at: <https://www.health.harvard.edu/healthbeat/9-things-that-can-undermine-your-vitamin-d-level> (Feb. 11, 2019)., Feb. 11, 2019.

(Continued)

*Primary Examiner* — James D. Anderson
(74) *Attorney, Agent, or Firm* — MARSHALL, GERSTEIN & BORUN LLP

(57) ABSTRACT

Methods for treating vitamin D insufficiency and secondary hyperparathyroidism in patients having CKD comprising administering repeat doses of 25-hydroxyvitamin D are disclosed. The methods comprise administering 25-hydroxyvitamin D in an amount effective to safely raise the patient's serum 25-hydroxyvitamin D level to greater than 90 ng/ml and/or to control the patient's serum ratio of 25-hydroxyvitamin D to 24,25-dihydroxyvitamin D to less than 20.

15 Claims, 16 Drawing Sheets

(56) References Cited

U.S. PATENT DOCUMENTS

| | | |
|---|---|---|
| 5,939,408 A | 8/1999 | Batcho et al. |
| 5,958,451 A | 9/1999 | Chen |
| 5,976,784 A | 11/1999 | DeLuca et al. |
| 6,001,884 A | 12/1999 | Nemeth et al. |
| 6,011,068 A | 1/2000 | Nemeth et al. |
| 6,031,003 A | 2/2000 | Nemeth et al. |
| 6,034,075 A | 3/2000 | Thys-Jacobs |
| 6,051,567 A | 4/2000 | Abrahamson et al. |
| 6,096,876 A | 8/2000 | St-Arnaud et al. |
| 6,121,469 A | 9/2000 | Norman et al. |
| 6,133,250 A | 10/2000 | Knutson et al. |
| 6,139,875 A | 10/2000 | Adams et al. |
| 6,147,064 A | 11/2000 | Knutson et al. |
| 6,150,346 A | 11/2000 | Knutson et al. |
| 6,190,591 B1 | 2/2001 | van Lengerich |
| 6,190,695 B1 | 2/2001 | Hoshino et al. |
| 6,211,244 B1 | 4/2001 | Van Wagenen et al. |
| 6,214,376 B1 | 4/2001 | Gennadios |
| 6,228,849 B1 | 5/2001 | Thys-Jacobs |
| 6,242,434 B1 | 6/2001 | Bishop et al. |
| 6,265,392 B1 | 7/2001 | Abrahamson et al. |
| 6,274,169 B1 | 8/2001 | Abrahamson et al. |
| 6,288,849 B1 | 9/2001 | Teramoto |
| 6,313,146 B1 | 11/2001 | Van Wagenen et al. |
| 6,340,473 B1 | 1/2002 | Tanner et al. |
| 6,342,249 B1 | 1/2002 | Wong et al. |
| 6,375,981 B1 | 4/2002 | Gilleland et al. |
| 6,376,479 B1 | 4/2002 | Knutson et al. |
| 6,380,408 B1 | 4/2002 | Posner et al. |
| 6,413,463 B1 | 7/2002 | Yamamoto et al. |
| 6,432,936 B1 | 8/2002 | DeLuca et al. |
| 6,491,950 B1 | 12/2002 | Gutierrez-Rocca et al. |
| 6,503,893 B2 | 1/2003 | Bishop et al. |
| 6,521,608 B1 | 2/2003 | Henner et al. |
| 6,524,788 B1 | 2/2003 | Cantor |
| 6,569,463 B2 | 5/2003 | Patel et al. |
| 6,572,888 B2 | 6/2003 | Byrd |
| 6,582,727 B2 | 6/2003 | Tanner et al. |
| 6,596,314 B2 | 7/2003 | Wong et al. |
| 6,627,622 B2 | 9/2003 | DeLuca et al. |
| 6,645,527 B2 | 11/2003 | Oshlack et al. |
| 6,770,295 B1 | 8/2004 | Kreilg et al. |
| 6,887,493 B2 | 5/2005 | Shefer et al. |
| 6,893,658 B1 | 5/2005 | Iida et al. |
| 6,903,083 B2 | 6/2005 | Knutson et al. |
| 6,911,217 B1 | 6/2005 | Gren et al. |
| 6,923,988 B2 | 8/2005 | Patel et al. |
| 6,929,803 B2 | 8/2005 | Wong et al. |
| 6,949,256 B2 | 9/2005 | Fonkwe et al. |
| 6,982,258 B2 | 1/2006 | Posner et al. |
| RE39,079 E | 4/2006 | Tanner et al. |
| 7,033,996 B2 | 4/2006 | Christakos |
| 7,056,655 B2 | 6/2006 | Cantor |
| 7,101,865 B2 | 9/2006 | Posner et al. |
| 7,122,530 B2 | 10/2006 | Bishop et al. |
| 7,166,585 B2 | 1/2007 | Posner et al. |
| 7,189,843 B2 | 3/2007 | Tsai et al. |
| 7,226,932 B2 | 6/2007 | Gokhale et al. |
| 7,255,921 B2 | 8/2007 | Kamaguchi et al. |
| 7,422,758 B2 | 9/2008 | Block et al. |
| 7,528,122 B2 | 5/2009 | DeLuca et al. |
| 7,632,518 B2 | 12/2009 | Tritsch et al. |
| 7,648,826 B1 | 1/2010 | Albertson et al. |
| 7,807,194 B2 | 10/2010 | Modliszewski et al. |
| 7,816,341 B2 | 10/2010 | Sewall et al. |
| 7,829,595 B2 | 11/2010 | Lawrence et al. |
| 7,846,475 B2 | 12/2010 | Shiraishi et al. |
| 7,973,024 B2 | 7/2011 | Posner et al. |
| 8,088,410 B2 | 1/2012 | Tritsch et al. |
| 8,101,203 B2 | 1/2012 | Cao |
| 8,101,204 B2 | 1/2012 | Cao |
| 8,142,811 B2 | 3/2012 | Oshlack et al. |
| 8,207,149 B2 | 6/2012 | Tabash et al. |
| 8,231,896 B2 | 7/2012 | Tanner et al. |
| 8,268,352 B2 | 9/2012 | Vaya et al. |
| 8,293,270 B2 | 10/2012 | Sukuru |
| 8,329,677 B2 | 12/2012 | Bishop et al. |
| 8,361,488 B2 | 1/2013 | Bishop et al. |
| 8,377,470 B2 | 2/2013 | Tanner et al. |
| 8,426,391 B2 | 4/2013 | Bishop et al. |
| 8,592,401 B2 | 11/2013 | Petkovich et al. |
| 8,759,328 B2 | 6/2014 | Deluca et al. |
| 8,778,373 B2 | 7/2014 | Bishop et al. |
| 8,906,410 B2 | 12/2014 | Bishop et al. |
| 8,962,239 B2 | 2/2015 | Petkovich et al. |
| 8,992,971 B2 | 3/2015 | Yang |
| 9,017,720 B2 | 4/2015 | Andersen et al. |
| 9,125,823 B2 | 9/2015 | Selva et al. |
| 9,402,855 B2 | 8/2016 | Bishop et al. |
| 9,408,858 B2 | 8/2016 | Bishop et al. |
| 9,498,486 B1 | 11/2016 | Bishop et al. |
| 9,500,661 B2 | 11/2016 | Petkovich et al. |
| 9,861,644 B2 | 1/2018 | White et al. |
| 9,913,852 B2 | 3/2018 | Bishop et al. |
| 9,918,940 B2 | 3/2018 | Bishop et al. |
| 9,943,530 B2 | 4/2018 | Bishop et al. |
| 10,220,047 B2 | 3/2019 | Petkovich et al. |
| 10,300,078 B2 | 5/2019 | White et al. |
| 10,350,224 B2 | 7/2019 | White et al. |
| 10,357,502 B2 | 7/2019 | White et al. |
| 10,493,084 B2 | 12/2019 | Petkovich et al. |
| 11,173,168 B2 | 11/2021 | Melnick et al. |
| 2001/0028896 A1 | 10/2001 | Byrd |
| 2001/0036472 A1 | 11/2001 | Wong et al. |
| 2002/0018810 A1 | 2/2002 | Oshlack et al. |
| 2002/0031798 A1 | 3/2002 | Anazawa et al. |
| 2002/0044968 A1 | 4/2002 | van Lengerich |
| 2002/0081331 A1 | 6/2002 | Tanner et al. |
| 2002/0128240 A1 | 9/2002 | Mazess |
| 2002/0155154 A1 | 10/2002 | Wong et al. |
| 2002/0183288 A1 | 12/2002 | Mazess et al. |
| 2003/0059471 A1 | 3/2003 | Compton et al. |
| 2003/0083360 A1 | 5/2003 | Crotts et al. |
| 2003/0129194 A1 | 7/2003 | Mazess et al. |
| 2003/0138482 A1 | 7/2003 | Fonkwe et al. |
| 2003/0152629 A1 | 8/2003 | Shefer et al. |
| 2003/0157560 A1 | 8/2003 | Cantor |
| 2003/0191093 A1 | 10/2003 | Chen et al. |
| 2003/0195171 A1 | 10/2003 | Daifotis et al. |
| 2004/0043971 A1 | 3/2004 | Mazess et al. |
| 2004/0092534 A1 | 5/2004 | Yam et al. |
| 2004/0101554 A1 | 5/2004 | Kirschner et al. |
| 2004/0132695 A1 | 7/2004 | Posner et al. |
| 2004/0197407 A1 | 10/2004 | Subramanian et al. |
| 2004/0224930 A1 | 11/2004 | Posner et al. |
| 2004/0258749 A1 | 12/2004 | Guldner et al. |
| 2005/0014211 A1 | 1/2005 | Armbruster et al. |
| 2005/0019374 A1 | 1/2005 | Modliszewski et al. |
| 2005/0037064 A1 | 2/2005 | Basquin et al. |
| 2005/0069579 A1 | 3/2005 | Kamaguchi et al. |
| 2005/0101576 A1 | 5/2005 | Whitehouse et al. |
| 2005/0106233 A1 | 5/2005 | Andersen et al. |
| 2005/0124591 A1 | 6/2005 | Tian et al. |
| 2005/0143358 A1 | 6/2005 | DeLuca et al. |
| 2005/0147669 A1 | 7/2005 | Lawrence et al. |
| 2005/0148557 A1 | 7/2005 | Tian et al. |
| 2005/0148558 A1 | 7/2005 | Knutson et al. |
| 2005/0186268 A1 | 8/2005 | Hoshi et al. |
| 2005/0208055 A1 | 9/2005 | Chuang et al. |
| 2005/0287213 A1 | 12/2005 | Wong et al. |
| 2006/0009425 A1 | 1/2006 | Delgado-Herrera et al. |
| 2006/0019933 A1 | 1/2006 | Boardman et al. |
| 2006/0029660 A1 | 2/2006 | Fonkwe et al. |
| 2006/0034937 A1 | 2/2006 | Patel |
| 2006/0057201 A1 | 3/2006 | Bonney et al. |
| 2006/0193877 A1 | 8/2006 | Tengler et al. |
| 2006/0210610 A1 | 9/2006 | Davidson et al. |
| 2006/0223119 A1 | 10/2006 | Cantor |
| 2006/0228808 A1 | 10/2006 | Clarke et al. |
| 2006/0257481 A1 | 11/2006 | Gurney et al. |
| 2007/0026067 A1 | 2/2007 | Yam et al. |
| 2007/0027120 A1 | 2/2007 | Whitehouse et al. |
| 2007/0032461 A1 | 2/2007 | Adorini et al. |
| 2007/0122477 A1 | 5/2007 | Bishop et al. |

(56) References Cited

U.S. PATENT DOCUMENTS

| | | |
|---|---|---|
| 2007/0155664 A1 | 7/2007 | Ranklove et al. |
| 2007/0190146 A1 | 8/2007 | Roger et al. |
| 2007/0207488 A1 | 9/2007 | Trump et al. |
| 2008/0109983 A1 | 5/2008 | Davis |
| 2008/0134937 A1 | 6/2008 | Yang |
| 2008/0199534 A1 | 8/2008 | Goldberg et al. |
| 2008/0317764 A1 | 12/2008 | Huber et al. |
| 2009/0004284 A1 | 1/2009 | Cheng et al. |
| 2009/0069389 A1 | 3/2009 | Choi et al. |
| 2009/0137536 A1 | 5/2009 | Mazess et al. |
| 2009/0155355 A1 | 6/2009 | Heuer et al. |
| 2009/0176748 A1 | 7/2009 | Tabash et al. |
| 2009/0209501 A1 | 8/2009 | Bishop et al. |
| 2009/0262685 A1 | 10/2009 | Schuringa et al. |
| 2009/0311316 A1 | 12/2009 | Bishop et al. |
| 2010/0120728 A1 | 5/2010 | Petkovich et al. |
| 2010/0144679 A1 | 6/2010 | Lyles |
| 2010/0144684 A1 | 6/2010 | Bishop |
| 2010/0204189 A1 | 8/2010 | Petkovich et al. |
| 2010/0227889 A1 | 9/2010 | Gerspacher et al. |
| 2010/0291191 A1 | 11/2010 | Shoichet et al. |
| 2010/0291197 A1 | 11/2010 | Schwab |
| 2011/0039809 A1 | 2/2011 | Buck et al. |
| 2011/0039810 A1 | 2/2011 | Buck et al. |
| 2011/0039811 A1 | 2/2011 | Buck et al. |
| 2011/0105444 A1 | 5/2011 | Deluca et al. |
| 2011/0118218 A1 | 5/2011 | Buck et al. |
| 2011/0130370 A1 | 6/2011 | Briault et al. |
| 2011/0171298 A1 | 7/2011 | Cao |
| 2011/0182986 A1 | 7/2011 | Speirs et al. |
| 2011/0256230 A1 | 10/2011 | Haeusler et al. |
| 2011/0300210 A1 | 12/2011 | Swanson et al. |
| 2011/0318321 A1 | 12/2011 | Selva et al. |
| 2011/0319503 A1 | 12/2011 | Muller et al. |
| 2012/0015916 A1 | 1/2012 | Tabash et al. |
| 2012/0135103 A1 | 5/2012 | Walsh et al. |
| 2013/0085121 A1 | 4/2013 | Wang et al. |
| 2013/0137663 A1 | 5/2013 | Messner et al. |
| 2013/0178451 A1 | 7/2013 | Bishop et al. |
| 2013/0189522 A1 | 7/2013 | Fujii et al. |
| 2013/0216618 A1 | 8/2013 | Muller et al. |
| 2013/0302309 A1 | 11/2013 | Yang |
| 2014/0088202 A1 | 3/2014 | Cade et al. |
| 2014/0248400 A1 | 9/2014 | Phonchareon et al. |
| 2014/0274977 A1 | 9/2014 | Bishop et al. |
| 2014/0349979 A1 | 11/2014 | White et al. |
| 2014/0357603 A1 | 12/2014 | Bishop et al. |
| 2015/0079165 A1 | 3/2015 | Bishop et al. |
| 2015/0119472 A1 | 4/2015 | Shuai et al. |
| 2015/0119473 A1 | 4/2015 | Shuai et al. |
| 2017/0119677 A1 | 5/2017 | Bishop et al. |
| 2018/0021354 A1 | 1/2018 | Petkovich et al. |

FOREIGN PATENT DOCUMENTS

| | | |
|---|---|---|
| DE | 20321698 U1 | 12/2008 |
| EP | 227836 A1 | 7/1987 |
| EP | 0413828 A1 | 2/1991 |
| EP | 0 508 756 A1 | 10/1992 |
| EP | 0 387 808 B1 | 5/1993 |
| EP | 0629405 A1 | 12/1994 |
| EP | 1080055 A2 | 3/2001 |
| EP | 1208843 A1 | 5/2002 |
| EP | 1165061 B1 | 10/2005 |
| EP | 1980255 A1 | 10/2008 |
| EP | 2148661 B1 | 12/2012 |
| EP | 2591354 A1 | 5/2013 |
| EP | 2037936 B1 | 6/2014 |
| JP | 55-139320 | 10/1980 |
| JP | 57-188520 | 11/1982 |
| JP | 58-032823 | 2/1983 |
| JP | 58206524 A | 12/1983 |
| JP | 64-031722 | 2/1989 |
| JP | 02-229115 | 9/1990 |
| JP | H02229115 A | 9/1990 |
| JP | 04-198129 | 7/1992 |
| JP | 04-208225 | 7/1992 |
| JP | H04288016 A | 10/1992 |
| JP | 07-242550 A | 9/1995 |
| JP | 08-092098 A | 4/1996 |
| JP | 10-158171 A | 6/1998 |
| JP | 11-158074 | 6/1999 |
| JP | 2001-512418 | 8/2001 |
| JP | 2002-302447 A | 10/2002 |
| JP | 2004-175750 A | 6/2004 |
| JP | 2004-531548 A | 10/2004 |
| JP | 2005-505589 A | 2/2005 |
| JP | 2005-513419 A | 5/2005 |
| JP | 2005-528383 A | 9/2005 |
| JP | 2005-531532 A | 10/2005 |
| JP | 2005-535682 A | 11/2005 |
| JP | 2005-538189 A | 12/2005 |
| JP | 2006-517593 A | 7/2006 |
| JP | 2006-523221 A | 10/2006 |
| JP | 2007-525472 A | 9/2007 |
| JP | 2010-506520 A | 2/2010 |
| JP | 2010-525079 A | 7/2010 |
| JP | 2011-512343 A | 4/2011 |
| JP | 2012-515738 A | 7/2012 |
| KR | 10-2012-0005228 A | 1/2012 |
| WO | WO-91/12807 A1 | 9/1991 |
| WO | WO-91/016899 A1 | 11/1991 |
| WO | WO-92/09271 A1 | 6/1992 |
| WO | WO-94/000128 A1 | 1/1994 |
| WO | WO-96/000074 A1 | 1/1996 |
| WO | WO-96/001621 A1 | 1/1996 |
| WO | WO-96/031215 A1 | 10/1996 |
| WO | WO-97/011053 A1 | 3/1997 |
| WO | WO-98/018610 A1 | 5/1998 |
| WO | WO-98/029105 A2 | 7/1998 |
| WO | WO-99/011272 A1 | 3/1999 |
| WO | WO-99/49027 A1 | 9/1999 |
| WO | WO-99/61398 A2 | 12/1999 |
| WO | WO-00/021504 A1 | 4/2000 |
| WO | WO-00/035419 A2 | 6/2000 |
| WO | WO-00/60109 A1 | 10/2000 |
| WO | WO-00/061123 A2 | 10/2000 |
| WO | WO-01/037808 A1 | 5/2001 |
| WO | WO-01/72286 A1 | 10/2001 |
| WO | WO-02/92056 A1 | 11/2002 |
| WO | WO-03/09572 A1 | 1/2003 |
| WO | WO-03/30869 A1 | 4/2003 |
| WO | WO-03/039521 A1 | 5/2003 |
| WO | WO-03/039572 A1 | 5/2003 |
| WO | WO-03/045381 A1 | 6/2003 |
| WO | WO-03/047595 A1 | 6/2003 |
| WO | WO-03/86267 A2 | 10/2003 |
| WO | WO-03/086415 A1 | 10/2003 |
| WO | WO-03/088976 A1 | 10/2003 |
| WO | WO-03/093459 A1 | 11/2003 |
| WO | WO-03/106411 A1 | 12/2003 |
| WO | WO-2004/010981 A1 | 2/2004 |
| WO | WO-2004/028515 A1 | 4/2004 |
| WO | WO-2004/054968 A2 | 7/2004 |
| WO | WO-2004/058235 A2 | 7/2004 |
| WO | WO-2004/071497 A1 | 8/2004 |
| WO | WO-2004/080467 A2 | 9/2004 |
| WO | WO-2004/098617 A2 | 11/2004 |
| WO | WO-2004/101554 A1 | 11/2004 |
| WO | WO-2004/110381 A2 | 12/2004 |
| WO | WO-2004/110391 A2 | 12/2004 |
| WO | WO-2005/000268 A2 | 1/2005 |
| WO | WO-2005/003358 A1 | 1/2005 |
| WO | WO-2005/011652 A2 | 2/2005 |
| WO | WO-2005/123120 A1 | 12/2005 |
| WO | WO-2006/052452 A1 | 5/2006 |
| WO | WO-2006/059180 A2 | 6/2006 |
| WO | WO-2006/113505 A2 | 10/2006 |
| WO | WO-2007/039193 A1 | 4/2007 |
| WO | WO-2007/039569 A2 | 4/2007 |
| WO | WO-2007/047327 A2 | 4/2007 |
| WO | WO-2007/050724 A2 | 5/2007 |
| WO | WO-2007/050975 A2 | 5/2007 |
| WO | WO-2007/053608 A2 | 5/2007 |

(56) References Cited

FOREIGN PATENT DOCUMENTS

| | | |
|---|---|---|
| WO | WO-2007/068287 A1 | 6/2007 |
| WO | WO-2007/092221 A2 | 8/2007 |
| WO | WO-2007/092755 A2 | 8/2007 |
| WO | WO-2007/146004 A1 | 12/2007 |
| WO | WO-2008/008608 A2 | 1/2008 |
| WO | WO-2008/043449 A1 | 4/2008 |
| WO | WO-2008/097646 A1 | 8/2008 |
| WO | WO-2008/116113 | 9/2008 |
| WO | WO-2008/116133 A1 | 9/2008 |
| WO | WO-2008/134512 A1 | 11/2008 |
| WO | WO-2008/134518 A2 | 11/2008 |
| WO | WO-2008/134523 A1 | 11/2008 |
| WO | WO-2009/047644 A2 | 4/2009 |
| WO | WO-2009/092755 A1 | 7/2009 |
| WO | WO-2009/101132 A1 | 8/2009 |
| WO | WO-2009/101135 A1 | 8/2009 |
| WO | WO-2009/101137 A1 | 8/2009 |
| WO | WO-2009/124210 A1 | 10/2009 |
| WO | WO-2010/011906 A1 | 1/2010 |
| WO | WO-2010/034342 A1 | 4/2010 |
| WO | WO-2011/031621 A2 | 3/2011 |
| WO | WO-2011/063952 A1 | 6/2011 |
| WO | WO-2011/095388 A1 | 8/2011 |
| WO | WO-2011/123476 A1 | 10/2011 |
| WO | WO-2012/006475 A1 | 1/2012 |
| WO | WO-2012/018329 A1 | 2/2012 |
| WO | WO-2012/076429 A1 | 6/2012 |
| WO | WO-2012/091569 A1 | 7/2012 |
| WO | WO-2012/117236 A1 | 9/2012 |
| WO | WO-2012/145491 A2 | 10/2012 |
| WO | WO-2014/029953 A1 | 2/2014 |
| WO | WO-2014/143941 A1 | 9/2014 |
| WO | WO-2014/193255 A1 | 12/2014 |
| WO | WO-2014/202754 A1 | 12/2014 |
| WO | WO-2016/020508 A2 | 2/2016 |

OTHER PUBLICATIONS

ACP Formulary and Pocket Guide to Psychopharmacology, Virginia DMHMRSAS, vol. 1, Iss. 1, (2004-2005).
Al-Aly, Z., Changes in Serum 25-Hydroxyvitamin D and Plasma Intact PTH Levels Following Treatment with Ergocalciferol in Patients With CKD, Am. J. Kid. Dis., 50(1):59-68 (2007).
Albertson et al., Quantitative mapping of amplicon structure by array CGH identifies CYP24 as a candidate oncogene, Nat. Genet., 25(2):144-6 (2000).
AlfaD3® 0.25, 0.5 or 1 microgram Capsules (Alfacalcidol, Package Leaflet, Apr. 2010).
Alfarol® Capsules 3ug (Package Leaflet, Mar. 2011).
Alvarez et al., Vitamin D Supplementation in Pre-Dialysis Chronic Kidney Disease, Dermato-Endocrinology, 4(2):118-127 (2012).
Amin, The impact of improved phosphorus control: use of sevelamer hydrochloride in patients with chronic renal failure, Nephrol Dial Transplant, 17:340-345 (2002).
Anderson et al., Expression of VDR and CYP24A1 mRNA in human tumors, Cancer Chemother. Pharmacol., 57(2):234-40 (2006).
Anderson et al., Quantification of mRNA for the vitamin D metabolizing enzymes CYP27B1 and CYP24 and vitamin D receptor in kidney using real-time reverse transcriptase-polymerase chain reaction, 2003. J. Mol. Endoc 31:123-132.
Andress, Vitamin D in chronic kidney disease: A systematic role for selective vitamin D receptor activation, Kidney Int., 69:33-43 (2006).
Arekat et al., Dramatic improvement of BMD following vitamin D therapy in a bone marrow transplant recipient, J. Clin. Densitometry, 5(3):297-71 (2002).
Armas et al., Vitamin $D_2$ is Much Less Effective than Vitamin $D_3$ in Humans, J. Clin. Endocrinol. Metab., 89:5387-5391 (2004).
Ashford, Chapter 20: Bioavailability—physicochemical and dosage form factors, pp. 314-333 IN: Aulton et al. (eds.), Aulton's Pharmaceutics. The Design and Manufacture of Medicines, Fourth Edition, Elsevier Publishing (2013).
Baez et al., Hipocalcemia severa posdenosumab, Nefrologfa (Madrid), 33(4): 614-615 (2013).
Baggiolini et al., Stereocontrolled Total Synthesis of 1 alpha, 25-Dihydroxycholecalciferol 1 and 1 alpha, 25-Dihydroxyergocalciferol, J. Org. Chem. 21: 3098-3108 (1986).
Bagnis et al., Biochemical and Hormonal Short-Term Effects of 25-hydroxyvitamin D3 in Patients on Continuous Peritoneal Dialysis, Ital. J. Mineral Electrolyte Metab., 12:73-76 (1998).
Bailie et al. Comparative Review of the Pharmacokinetics of Vitamin D Analogues, Seminars in Dialysis, 15(5):352-357 (2000).
Baird et al., Steroid Dynamics Under Steady-State Conditions, Recent Prog. Horm. Res., 25:611-664 (1969).
Baker et al., Plasma 25-hydroxy vitamin D concentrations in patients with fractures of the femoral neck, British Medical Journal, 1(6163):589 (1979).
Barger-Lux et al., Vitamin D and Its Major Metabolites: Serum Levels After Graded Oral Dosing In Healthy Men Osteoporosis International, United Kingdom, 8(3):222-230 (1998).
Barreto et al., 25-Hydroxyvitamin $D_3$, the Prohormone of 1,25-Dihydroxyvitamin $D_3$, Inhibits the Proliferation of Primary Prostatic Epithelial Cells, Cancer Epidemiol, Biomarkers & Prevention, 9:265-270 (2000).
Beckman, et al., Up-Regulation of the Intestinal 1, 25-Dihydroxyvitamin D Receptor During Hypervitaminosis D: A Comparison Between Vitamin D2 and Vitamin D3 1, Biochemical and Biophysical Research Communications, vol. 169, No. 3, pp. 910-915 (Jun. 29, 1990).
Beer et al., Pharmacokinetics and Tolerability of a Single Dose of DN-101, a New Formulation of Calcitriol, in Patients with Cancer, Clin. Cancer Res., 11:7794-7799 (2005).
Bell et al., Evidence that 1,25-Dihydroxyvitamin D3 Inhibits the Hepatic Production of 25-Hydroxyvitamin D in Man, J. Clin. Invest., 74:1540-1544 (1984).
Belostotsky et al., A single high dose of ergocalciferol can be used to boost 25-hydroxyvitamin D levels in children with kidney disease, Pediatr Nephrol, 24:625-626 (2009).
Berg et al., 24,25-Dihydroxyvitamin d3 and vitamin D status of community-dwelling black and white Americans, Clin. Chem., 61(6):877-84 (Jun. 2015).
Berruti et al., Prognostic role of serum parathyroid hormone levels in advanced prostate cancer patients undergoing zoledronic acid administration, Oncologist, 17(5):645-52 (2012).
Bertoldo et al., Serum 25-hydroxyvitamin D levels modulate the acute-phase response associated with the first nitrogen-containing bisphosphonate infusion, J. Bone Miner. Res., 25(3):447-54 (Mar. 2010).
Bhatia et al., EB1089 inhibits the parathyroid hormone-related protein-enhanced bone metastasis and xenograft growth of human prostate cancer cells, Mol. Cancer Ther., 8(7):1787-98 (2009).
Bianchi et al., No Difference in Intestinal Strontium Absorption After an Oral or an Intravenous 1,25(OH)2D3 Bolus in Normal Subjects, J. Bone Miner. Res., 14:1789-1795 (1999).
Binkley et al., Laboratory Reporting of 25-Hydroxyvitamin D Results: Potential for Clinical Misinterpretation, Clinical Chemistry, 52(11);2124-2125 (2006).
BioTrends Research Group, TreatmentTrends®: Nephrology (US) Q4 2014 (Dec. 2014).
Bischoff-Ferrari, The 25-hydroxyvitamin D threshold for better health, J. Steroid Biochem. Mol. Biol., 103:614-619 (2007).
Blair et al., Prevalence of vitamin D [25(OH)D] deficiency and effects of supplementation with ergocalciferol (vitamin D2) in stage 5 chronic kidney disease patients. J. Ren Nutr., 18: 375-382 (2008).
Blunt et al., Biological activity of 25-hydroxycholecalciferol, a metabolite of vitamin D3, Proc. Natl. Acad. Sci. USA, 61(4):1503-6 (1968).
Bordier et al., Evolution of renal osteodystrophy: Correlation of bone histomorphometry and serum mineral and immunoreactive parathyroid hormone values before and after treatment with calcium carbonate or 25-hydroxycholecalciferol, Kidney Int Suppl, 2:S102-S112 (1975).

(56) References Cited

OTHER PUBLICATIONS

Boudville et al., Renal Function and 25-Hydroxyvitamin D Concentrations Predict Parathyroid Hormone Levels in Renal Transplant Patients, Nephrol Dial Transplant, 21:2621-2624 (2006).
Bouillon et al., Influence of dialysate calcium concentration and vitamin D on serum parathyroid hormone during repetitive dialysis, Kidney Int., 7:422-432 (1975).
Boxtel et al., Drug Benefits and Risks, International Textbook of Clinical Pharmacology, p. 75-76 (2001).
Briese et al., Arterial and cardiac disease in young adults with childhood-onset end-stage renal disease-impact of calcium and vitamin D therapy, Nephrology Dialysis Transplantation., 21:1906-1914 (2006).
Brodowicz et al., Early identification and intervention matters: A comprehensive review of current evidence and recommendations for the monitoring of bone health in patients with cancer, Cancer Treat Rev., 61:23-34 (2017).
Brossard et al. Influence of Glomerular Filtration Rate on Non-(1-84) Parathyroid Hormone (PTH) Detected by Intact PTH Assays, Clinical Chemistry, 46(5):697-703 (2000).
Brown et al., The Vitamin D Prodrugs $1\alpha(OH)D_2$, $1\alpha(OH)D_3$ and BCI-210 Suppress PTH Secretion by Bovine Parathyroid Cells, Nephrol Dial Transplant, 21:644-650 (2006).
Brown et al., Vitamin D Analogues for Secondary Hyperparathyroidism, Nephrol Dial Transplant, 17[Suppl. 10]:10-19 (2002).
Buccianti et al., Effects of Calcifediol Treatment on the Progression of Renal Osteodystrophy during Continuous Ambulatory Peritoneal Dialysis, Nephron, 56:353-356 (1990).
Budavari (ed.), Merck Index: an Encyclopedia of Chemicals, Drugs, and Biologicals, 11th Edition, Merck & Co., 9927-9930 (1989).
Bulla et al., Renal bone disorders in children: therapy with vitamin D3 or 1,25-dihydroxycholecalciferol, Proc.Eur.Dial. Transplant. Assoc., 16: 644-648 (1979).
Cavalli et al., Biological effects of various regimes of 25-hydroxyvitamin D3 (calcidiol) administration on bone mineral metabolism in postmenopausal women, Clinical Cases in Mineral and Bone Metabolism, 6(2): 169-173 (2009).
Centorrino et al., Multiple versus single antipsychotic agents for hospitalized psychiatric patients: case-control study of risks versus benefits, Am J. Psychiatry, 161(4): 700-06 (2004).
Chandra et al., Cholecalciferol (vitamin D3) therapy and vitamin D insufficiency in patients with chronic kidney disease: a randomized controlled pilot study, Endocr. Pract., 14: 10-17 (2008).
Chapuy et al., Biochemical effects of calcium and vitamin D supplementation in elderly, institutionalized, vitamin D-deficient patients, Rev. Rhum. [Engl. Ed. 63 (2), 135-140), Feb. 1996.
Charnow, Novel Formulation Corrects Vitamin D, Lowers iPTH, Renal & Urology News (2012).
Chen et al., Safety of Denosumab Versus Zoledronic Acid in Patients with Bone Metastases: A Meta-Analysis of Randomized Controlled Trials, Oncol. Res. Treat., 39(7-9):453-9 (2016).
Chonchol et al., 25-Hydroxyvitamin D, insulin resistance, and kidney function in the Third National Health and Nutrition Examination Survey, Kidney Int., 71(2):134-9 (2007).
Claris-Appiani et al., Phosphate-Induced PTH Stimulation and Calcitriol Treatment in Children with Early Chronic Renal Insufficiency, J. Bone Miner. Met., 12:S91-S97 (1994).
Coburn et al., Doxercalciferol Safely Suppresses PTH Levels in Patients with Secondary Hyperparathyroidism Associated with Chronic Kidney Disease Stages 3 and 4, Am. J. Kidney Dis., 43(5):877-890 (2004).
Coburn, An Update on Vitamin D as Related to Nephrology Practice: 2003, Kidney International, vol. 64, Supplement 87, pp. S125-S130 (2003).
Coburn, et al., Use of Active Vitamin D Sterols in Patients with Chronic Kidney Disease, Stages 3 and 5, Kidney International, vol. 63, Supplement 85, pp. S49-S53 (2003).
Coen et al., 1,25(OH)2D3 and 25-OHD3 in the Treatment of Renal Osteodystrophy: Comparison of Combined Versus 1,25(OH)2D3 Administration Alone, Miner. Electrolyte Metab., 9:19-27 (1983).
Coen et al., 25-hydroxycholecalciferol in the treatment of renal osteodystrophy in haemodialysed patients, Int J Artificial Organs, 2(6): 278-281 (1979).
Cohen-Solal et al., Non-Aluminic Adynamic Bone Disease in Non-Dialyzed Uremic Patients: A New Type of Osteopathy Due to Overtreatment? Bone, 13:1-5 (1992).
Collet et al. Modified-Release Peroral Dosage Forms, Aulton (ed.), Pharmaceutics: The Science of Dosage Forms, Churchill Livingston, London, pp. 289-305 (2002).
Colodro et al., Effect of 25-Hydroxy-Vitamin D3 on Intestinal Absorption of Calcium in Normal Man and Patients With Renal Failure, Metabolism, 27(6):745-753 (1978).
Cooke et al., Vitamin D-Binding Protein (Gc-Globulin): Update 1995, Endocrine Rev., 4:125-128 (1995).
Coyne et al., Paricalcitol Capsule for the Treatment of Secondary Hyperparathyroidism in Stages 3 and 4 CKD, American Journal of Kidney Diseases, 47(2):263-276 (2006).
Daisley-Kydd et al., Calcitriol in the Management of Secondary Hyperparathyroidism of Renal Failure, Pharmacotherapy., 16:619-630 (1996).
Database WPI Week 199546 Thomson Scientific, London, GB; An 1995-355178 XP002680886.
Davies et al. The Absorption and Metabolism of Vitamin D3 from Parenteral Injection Sites', Proceedings of the Workshop on Vitamin D, 4th, Vitam. D: Basic Res. Its Clin. Appl. (1979), abstract.
DB-Pharma, Dedrogyl 15 Mg/10ML Calcifediol Oral Drops, Solution, Marketing Authorization No. 317 863.2 (2000).
DeLuca, Treatment of renal osteodystrophy with 25-hydroxycholecalciferol, Arch Intern Med, 126(5):896-899 (1970).
Deroisy et al., Comparison of the Short-Term Effects of Three Oral Calcium-Vitamin D Formulations and Placebo on Calcium Metabolism, Curr. Ther. Res., 59:370-378 (1998).
DeVille et al., Effect of Ergocalciferol Supplementation on Serum Parathyroid Hormone and Serum 25-Hydroxyvitamin D in Chronic Kidney Disease, Nephrology, 11:555-559 (2006).
Dietary Reference Intakes for Calcium, Phosphorus, Magnesium, Vitamin D, and Fluoride, Standing Committee on the Scientific Evaluation of Dietary Reference Intakes, Food and Nutrition Board, Institute of Medicine, National Academy Press, Washington DC, pp. 250-287 (1997).
Dietary Supplement Fact Sheet: Vitamin D, National Institutes of Health, Office of Dietary Supplements (last update: Aug. 5, 2005), retrieved from <URL: http:ods.od.nih.gov/factsheets/vitamind.asp> on Aug. 31, 2007.
Disease and Vitamin D, University of California Riverside, retrieved from Internet, <URL: <http://vitamind.ucr.edu/disease.html>> (last update: May 19, 1999).
Disintegration, chapter 701; Dissolution, chapter 711; Distilling Range, chapter 721; Drug Release, chapter 724; Electrophoresis, chapter 726; pp. 276-292, in: U.S. Pharmacopeia vol. 30.
Dogan et al., Effect of depot oral cholecalciferol treatment on secondary hyperparathyroidism in stage 3 and stage 4 chronic kidney diseases patients, Ren Fail., 30: 407-410 (2008).
Drueke et al., Recurrence of hyperparathyroidism from autografted parathyroid fragments in uremic patients in spite of administration of 25(OH)D3 and 1a(OH)D3. In: Vitamin D. Basic Research and its Clinical Application, (Eds. Norman AW, Schaefer K, Herrath Dv, Grigoleit HG, Coburn JW, DeLuca HF, Mawer EB, and Suda T), pp. 791-794. Willem de Gruyter, New York (1979).
Dusso et al., Metabolic Clearance Rate and Production Rate of Calcitriol in Uremia, Kidney Int., 35 860-864 (1989).
Dusso et al., Extra-renal production of calcitriol in chronic renal failure, Kidney Int., 34:368-375 (1988).
Dusso et al., Extrarenal Production of Calcitrol in Normal and Uremic Humans*, Journal of Clinical Endocrinology and Metabolism, 72(1):157-164 (1991).
E.W. Martin, Drug Interactions, in Hazards of Medication, J.B. Lippincott Co. (1978).
Eastwood et al., Biochemical and histological effects of 1,25 dihydroxycholecalciferol (1,25-DHCC) in the osteomalacia of chronic renal failure, J Urol Nephrol (Paris,) 80(12): 984-985 (1974).

(56) References Cited

OTHER PUBLICATIONS

Eastwood et al., The contrasting effects on bone histology of vitamin D and of calcium carbonate in the osteomalacia of chronic renal failure, Clin Sci Molec Med, 47:23-42 (1974).

Eastwood et al., The Effect of 25-Hydroxy Vitamin D3 in the Osteomalacia of Chronic Renal Failure, Clin. Sci. Molec. Med., 52:499-508 (1977).

El Abdaimi et al., Reversal of hypercalcemia with the vitamin D analogue EB1089 in a human model of squamous cancer, Cancer Res., 59(14):3325-8 (1999).

Ennis et al., Current recommended 25-hydroxyvitamin D targets for chronic kidney disease management may be too low, J. Nephrol., 29(1):63-70 (Feb. 2016).

Epps et al., Vitamin D Metabolism: Implications for Treatment in Oncology, Oncology News, 4:42-44 (2009).

European Patent Office, Intention to Grant Notification, from corresponding European patent application No. EP 07840277.3 (Jan. 9, 2014).

Fernandez et al., Guidelines for Dosing of Intravenous Calcitriol in Dialysis Patients with Hyperparathyroidism, Nephrol. Dial. Transplant., 11:96-101 (1996).

Fliser et al., Fibroblast gowth factor 23 (FGF23) predicts progression of chronic kidney disease: the mild to moderate kidney disease (MMKD) study, J. Am. Soc. Nephrol., 18:2601-8 (2007).

Fournier et al., 1-alpha-Hydroxycholecalciferol and 25-Hydroxycholecalciferol in Renal Bone Disease, Calcified Tissues 1975: Proceedings of the 11th European Symposium on Calcified Tissues, 226-235 (1975).

Fournier et al., 1α Hydroxycholecalciferol and 25 Hydroxycholecalciferol in Renal Bone Disease Proc Eur Dial Transplant Assoc 12:227-236 (1976).

Fournier et al., 1α-hydroxycholecalciferol and 25-hydroxycholecalciferol in Renal Bone Disease Calcif Tissue Res. 21:226-235 (1976).

Fournier et al., Advances in Nephrology from the Necker Hospital Adv. Nephrol Necker Hosp. 21:237-306 (1992).

Fournier et al., Comparison of 1α-hydroxycholecalciferol and 25-hydroxycholecalciferol in the treatment of renal osteodystrophy: Greater effect of 25-hydroxycholecalciferol on bone mineralization Kidney International 15:196-204 (1979).

Fournier et al., Current Status of the Management of Renal Osteodystrophy Proceedings of the European Dialysis and Transplant Association 15:547-568 (1978).

Fournier et al., Impact of calcium and vitamin D therapy on arterial and cardiac disease in young adults with childhood-onset and stage renal disease, Nephrol Dial Transplant , 22:956-957 (2006).

Fournier et al., Importance of Vitamin D Repletion in Uraemia, Nephrol Dial Transplant, 14(4):819-823 (1999).

Fournier et al., Low doses of calcitriol or calcium carbonate for the prevention of hyperparathyroidism in predialysis patients? Nephrol Dial Transplant 11(7):1493-1495 (1996).

Fournier et al., Present-Day Concepts in the Treatment of Chronic Renal Failure Contrib Nephrol. 71:64-80 (1989).

Fournier et al., Preventing Renal Bone Disease in Moderate Renal Failure with CaCO3 and 25(OH) Vitamin D3, Kidney Int., 33:S178-S279 (1988).

Fournier et al., Renal Osteodystrophy in Dialysis Patients: Diagnosis and Treatment, Artificial Organs, 22:530-557 (1998).

Fournier et al., Renal Osteodystrophy: Pathophysiology and Treatment Hormone Res. 20:44-58 (1984).

Fournier et al., The Approach to the Treatment of Secondary Hyperparathyroidism in Early Renal Failure Am. J. Nephrol 8:170-172 (1988).

Fournier et al., Traitement vitaminique D et ostéodystrophies rénales: indications et modalités Nephrologie 16(2):165-190 (1995) [journal in French].

Fournier, Vitamin D: Biochemical, Chemical, and Clinical Aspects Related to Calcium Metabolism, Vitamin D: Proceedings of the Third Workshop on Vitamin D, Asilomar, Pacific Grove, CA, USA 667-669 (1977).

Friedman et al. The Role of Vitamin D in Mild to Moderate Chronic Kidney Disease, Trends in Endocrinology & Metab,. 13(5):189-194 (2002).

Friedrich et al., Analysis of the vitamin D system in cervical carcinomas, breast cancer and ovarian cancer, Recent Results Cancer Res., 164:239-46 (2003).

Fritsche et al., Regulation of 25-Hydroxyvitamin $D_3$-$1\alpha$-Hydroxylase and Production of $1\alpha,25$-Dihydroxyvitamin $D_3$ by Human Dendritic Cells, Blood, 102(9):3314-3316 (2003).

Frohling et al., Serum 25-hydroxyvitamin D in patients with chronic renal failure on long-term treatment with high doses of vitamin D2. Nephron 26: 116-120 (1980).

Frost et al., Histomorphometric Changes in Trabecular Bone of Renal Failure Patients Treated with Calcifediol, Metab. Bone Dis. & Rel. Res., 2:285-295 (1981).

Fukagawa et al., FGF23: its role in renal bone disease, Pediatr. Nephrol., 21:1802-6 (2006).

Fukagawa et al., With or without the kidney: the role of FGF23 in CKD, Nephrol. Dial. Transplant., 20:1295-8 (2005).

Gal-Moscovici et al., Role of vitamin D deficiency in chronic kidney disease, Journal of Bone and Mineral Res. 22:V91-V94 (2007).

Gallagher et al., Comparison of the Histological Effect and Metabolism of 25-(OH)D and 1,25-(OH)2D in Rat Bone, p. 399-401, IN: Norman, Vitamin D: Basic Research and its Clinical Application: Proceedings of the Fourth Workshop on Vitamin D, Berlin, West Germany, Feb. 1979.

Garland et al., Vitamin D for cancer prevention: global perspective, Ann. Epidemiol., 19(7):468-83 (2009).

Ghazali et al., Is low plasma 25-(OH) vitamin D a major risk factor for hyperparathyroidism and Looser's zones independent of calcitriol? Kidney International 55:2169-2177 (1999).

Gibson, ed., Product optimisation. Pharmaceutical Preformulation and Formulation: A Practical Guide from Candidate Drug Selection to Commercial Dosage Form, 295-8 (2004).

Goldzieher, Single-monthly-dose vitamin D supplementation in elderly patients, Endocr Pract., 5(5):229-32 (Sep.-Oct. 1999).

Gomez-Alonso et al., Vitamin D Status and Secondary Hyperparathyroidism: The Importance of 25-Hydroxyvitamin D Cut-Off Levels, Kidney International, 63(Supp. 85):544-548 (2003).

Goodman, Calcimimetic agents and secondary hyperparathyroidism: treatment and prevention, Nephrol Dial Transplant, 2002;17:204-207.

Gopinath et al., Disintegrants—A Brief Review, J. Chem. Pharm. Sci., 5(3):105-12 (Jul.-Sep. 2012).

Gradishar et al., Minimizing cancer's impact on bone with denosumab: current and future perspectives, Community Oncology, 10(8):235-243 (2013).

Granja et al., Studies on the Opening of Dioxanone and Acetal Templates and Application to the Synthesis of $1\alpha,25$-Dihydroxyvitamin $D_2^1$, J. Org. Chem., 58:124-131 (1993).

Guidance for Industry, Nonclinical Safety Evaluation of Drug or Biologic Combinations, U.S. Department of Health and Human Services, Food and Drug Administration (Mar. 2006).

Haddad et al., Acute Administration of 25-Hydroxycholecalciferol in Man, J. Clin. Endocrinol. Metab., 42:284-289 (1976).

Haddad et al., Human Serum Binding Capacity and Affinity for 25-Hydroxyergocalciferol and 25-Hydroxycholecalciferol, J. Clin. Endocrinol. Metab., 43:86-91 (1976).

Haddad et al., Natural and Synthetic Sources of Circulating 25-Hydroxyvitamin D in Man, Nature, 244:515-517 (1973).

Haddad et al., Vitamin D plasma binding protein. Turnover and fate in the rabbit, J. Clin. Invest., 67(5):1550-60 (1981).

Haddad, Plasma Vitamin D-binding Protein (Gc-Globulin): Multiple Tasks, J. Steroid Biochem. Molec. Biol., 53:579-582 (1995).

Haddad, Seasonal Diminution of Vitamin D Stores in the United States: Can Darker Winters Lead to Lighter Bones? Trends Endocrinol. Metab., 7:209-212 (1996).

Haddad, Traffic, Binding and Cellular Access of Vitamin D Sterols, Bone and Mineral Res., Elsevier, 5:281-308 (1987).

Haddad, Vitamin D—Solar Rays, The Milky Way, or Both? NEJM, 326:1213-1215 (1992).

(56) References Cited

OTHER PUBLICATIONS

Haldimann et al., Effect of an Oral Dose of 25-Hydroxyvitamin D3 on Its Blood Levels in Patients with the Nephrotic Syndrome, J Clin Endocrinology and Metabolism, 50(3): 470-474 (1980).
Halloran et al., Plasma Vitamin D Metabolite Concentrations in Chronic Renal Failure: Effect of Oral Administration of 25-Hydroxyvitamin D3, J. Clin. Endocrin. & Metab., 59:1063-1069 (1984).
Hamida et al., Hyperparathyroïdie secondaire àlinsuffisance rénale Annales d'Endocrin-ologie 55:147-158 (1994) [reference in French].
Hannula et al., Constant, But Not Pulsed Calcitriol Suppresses Hemodialysis Patients' Antigen-Induced Lymphocyte Proliferation, Nephron, 86:139-144 (2000).
Hari et al., Vitamin D insufficiency and effect of cholecalciferol in children with chronic kidney disease, Pediatr. Nephrol,. 25: 2483-2488 (2010).
Harris et al., Pharmacokinetics of cinacalcet hydrochloride when administered with ketoconazole, Clinical Pharmacokinetics, Adis International Ltd., Auckland, NZ, vol. 46, No. 6, Jan. 1, 2007 (Jan. 1, 2007), pp. 495-501.
Hay et al., Vitamin D2 in Vertebrate Evolution, Comp. Biochem. Physiol. B, 56:375-380 (1977).
Hectorol® (doxercalciferol) Capsules (Label, FDA, 2010).
Helvig et al., Dysregulation of renal vitamin D metabolism in the uremic rat, Kidney Int., 78(5):463-72 (2010).
Hemodialysis, 2015, 4 pages, Accessed from https://www.kidney.org/atoz/content/hemodialysis on Jun. 19, 2019) (Year: 2015).
Henry et al., Response of chick parathyroid glands to the vitamin D metabolites, 1,25-dihydroxycholecalciferol and 24,25-dihydroxycholecalciferol, J. Nutr., 107(10):1918-26 (1977).
History of Changes for Study: NCT01219855, Safety/Efficacy Study of CTAP101 in Chronic Kidney Disease Subjects With Secondary Hyperparathyroidism (SHPT) (https://clinicaltrials.govict2/show/NCT01219855, published Oct. 6, 2012, accessed Apr. 12, 2019) (Year: 2012).
Hodson et al., Treatment of childhood renal osteodystrophy with calcitriol or ergocalciferol, Clin Nephrology, 24(4): 192-200 (1985).
Holick et al., Vitamin D2 is as effective as vitamin D3 in maintaining circulating concentrations of 25-dydroxyvitamin D, J Clin Endocrinol Metab., 93(3):677-81 (2008).
Holick et al., Evaluation, treatment, and prevention of vitamin D deficiency: an Endocrine Society clinical practice guideline, J. Clin. Endocrinol. Metab., 96(7):1911-30 (Jul. 2011).
Holick, Vitamin D Deficiency in CKD: Why Should We Care? Am. J. Kidney Dis., 45:1119-1121 (2005).
Holick, Vitamin D Status: Measurement, Interpretation and Clinical Application, Ann Epidemiol, 19(2):73-78 (2009).
Holick, Vitamin D for health and in chronic kidney disease, Semin. Dial., 18(4):266-75 (2005).
Holick, Vitamin D: A millenium perspective, J. Cell Biochem . . . 88:296-307 (2003).
Hollis, Circulating 25-Hydroxyvitamin D Levels Indicative of Vitamin D Sufficiency: Implications for Establishing a New Effective Dietary Intake Recommendation for Vitamin D, J. Nutr. 135: 317-322 (2005).
Holmberg et al., Absorption of a pharmacological dose of vitamin D3 from two different lipid vehicles in man: comparison of peanut oil and a medium chain triglyceride, Biopharm. Drug Dispos., 11(9):807-15 (1990).
Horst et al., A Sensitive Competitive Protein Binding Assay for Vitamin D in Plasma, Steroids, 37:581-592 (1981).
Horst et al., Discrimination in the Metabolism of Orally Dosed Ergocalciferol and Cholecalciferol by the Pig, Rat and Chick, Biochem. J., 204:185-189 (1982).
Horst et al., Rat cytochrome P450C24 (CYP24) does not metabolize 1,25-dihydroxyvitamin D2 to calcitroic acid, J. Cell Biochem., 88:282-285 (2003).
Hottelart et al., Ostéodystrophie rénale (2): son traitement chez l'insuffisant rénal avant la dialyse Nephrologie 21(6):275-282 (2000) [reference in French].

Houghton et al., The Case Against Ergocalciferol (Vitamin D2) as a Vitamin Supplement, Am. J. Clin. Nutr., 84:694-697 (2006).
Hunt, et al., A Comparison of the Toxicity of Ergocalciferol and Cholecalciferol in Rhesus Monkeys (*Macaca mulatta*), J. Nutrition, 102:975-986 (1972).
Hussar, New Drugs of 1999, J. Am. Pharmacist. Assoc. 40(2):181-229 (2000).
Ibrahim et al., Serum fibroblast growth factor-23 levels in chronic haemodialysis patients, Int. Urol. Nephrol., 41:163-9 (2009).
Inoue et al., Role of the vitamin D receptor in FGF23 action on phosphate metabolism, Biochem. J., 399:325-31 (2005).
International Application No. PCT/EP2017/057282, International Preliminary Report on Patentability, dated Oct. 2, 2018.
International Application No. PCT/EP2017/057282, International Search Report and Written Opinion, mailed Sep. 8, 2017.
International Preliminary Report on Patentability for Corresponding International Application No. PCT/EP17/57282, dated Oct. 11, 2018, 7 pages.
International Preliminary Report on Patentability for Corresponding International Application No. PCT/US09/39355, dated Oct. 14, 2010, 8 pages.
International Search Report and Written Opinion, International Application No. PCT/EP2015/068219, mailed Jan. 29, 2016.
International Search Report and Written Opinion, International Application No. PCT/EP2016/052866, mailed Jun. 9, 2016.
International Search Report for Application No. PCT/US2007/061521, dated Jul. 17, 2007.
International Search Report of counterpart PCT/US2008/061579 dated Aug. 21, 2008 (5 pages).
International Search Report of PCT/US2008/061579 dated Aug. 21, 2008 (5 pages).
Ishimura et al., Serum Levels of 1,25-Dihydroxyvitamin D, 24,25-Dihydroxyvitamin D, and 25-Hydroxyvitamin D in Nondialyzed Patients with Chronic Renal Failure, Kidney Int., 55:1019-1027 (1999).
Japanese Office Action for Application No. 2008-553520, dated Jul. 24, 2013.
Japanese Patent Application No. 2017-506724, Office Action, dated May 27, 2019.
Jara et al., Effect of Calcitriol Treatment and Withdrawal on Hyperparathyroidism in Haemodialysis Patients with Hypocalcaemia, Nephrol. Dial. Transplant., 16:1009-1016 (2001).
Jean et al., Daily Oral 25-Hydroxycholecalciferol Supplementation for Vitamin D Deficiency in Haemodialysis Patients: Effects on Mineral Metabolism and Bone Markers, Nephrol. Dial. Transplant, 23:3670-3676 (2008).
Jean et al., Evidence for Persistent Vitamin D 1-Alpha-Hydroxylation in Hemodialysis Patients: Evolution of Serum 1,25-Dihydroxycholecalciferol after 6 Months of 25-Hydroxycholecalciferol Treatment Nephron. Clin. Pract. 110:c58-c65 (2008).
Jean et al., Monthly cholecalciferol administration in heamodialysis patients: a simple and efficient strategy for vitamin D supplementation Nephrol. Dial. Transplant 24(12):3799-3805 (2009).
Jones et al., Cytochrome P450-mediated metabolism of vitamin D, J. Lipid Res., 55(1):13-31 (2014).
Jones, Pharmacokinetics of vitamin D toxicity, Am. J. Clin. Nutr. 88(suppl): 582S-6S (2008).
Jones, Why dialysis patients need combination therapy with both cholecalciferol and a calcitriol analogs, Seminars in Dialysis, pp. 1-5 (2010).
Jones., Expanding the Role for Vitamin D in Chronic Kidney Disease: Importance of Blood 25-OH-D Levels and Extra-Renal 1α-Hydroxyase in the Classical and Nonclassical Actions of 1α, 25-Dihydroxyvitamin D3, Seminars in Dialysis, 20(4):316-324 (2007).
Joy et al: Outcomes of Secondary Hyperparathyroidism in Chronic Kidney Disease and the Direct Costs of Treatment, Journal of Managed Care Pharmacy, Academy of, Managed Care Pharmacy, Alexandria, VA, vol. 13, No. 5, Jan. 1, 2007 (Jan. 1, 2007), pp. 397-411.
Kajihara et al., Novel Method to Control Release of Lipophilic Drugs with High Potency from Silicone, Chem. Pharm. Bull., 51:11-14 (2003).

(56) References Cited

OTHER PUBLICATIONS

Kalantar-Zadeh et al., Clinical Outcomes with Active versus Nutritional Vitamin D Compounds in Chronic Kidney Disease Clin J Am Soc Nephrol. 4(9):1529-1539 (2009).
Kanis et al., Rate of Reversal of Hypercalcaemia and Hypercalciuria Induced by Vitamin D and Its 1-alpha-Hydroxylated Derivatives, BMJ, 1:78-81 (1977).
Kaufmann et al., Clinical utility of simultaneous quantitation of 25-hydroxyvitamin D and 24,25-dihydroxyvitamin D by LC-MS/MS involving derivatization with DMEQ-TAD, J. Clin. Endocrinol. Metab., 99(7):2567-74 (Jul. 2014).
Kazama et al., Role of circulating fibroblast growth factor 23 in the development of secondary hyperparathyroidism, Ther. Apher. Dial., 9:328-30 (2005).
KDOQI Clinical practice guidelines 2004. National Kidney Foundation).
Khachane et al., Novel Suatained Release Drug Delivery System: Review, IJPRD, 3(12):1-14 (2012).
Kidney Disease Improving Global Outcomes (KDIGO) 2017 Clinical Practice Guideline Update for the Diagnosis, Evaluation, Prevention, and Treatment of Chronic Kidney Disease-Mineral and Bone Disorder (CKD-MBD). Kidney Int Suppl. 2017;7(1):1-59.
Kidney Disease Improving Global Outcomes (KDIGO) Clinical Practice Guidelines for Diagnosis, Evaluation, Prevention, and Treatment of Chronic Kidney Disease-Mineral and Bone Disorder (CKD-MBD), Kidney International Supplement, 113:S1-130 (2009).
Kim, Advanced Pharmaceutics: Physicochemical Principles, pp. 362-392, Boca Raton, Fla: CRC Press (2004).
Kinoshita et al., 1,25-Dihydroxyvitamin D Suppresses Circulating Levels of Parathyroid Hormone in a Patient with Primary Hyperparathyroidism and Coexistent Sarcoidosis, J. Clin. Endo. & Metabol., 90(12):6727-6731 (2005).
Kleinman et al., Effects of Calcifediol on Calcified Tissue in Uremia, Arch Intern Med, 138: 864-865 (1978).
Kobayashi et al., 2β-(3-Hydroxyproxy)-α,25-Dihydroxyvitamin $D_3$ (ED-71), Preventive and Therapeutic Effects on Bone Mineral Loss in Ovariectomized Rats, Bioorganic & Medicinal Chemistry Letters, 3(9):1815-1819 (1993).
Kobayashi et al., Variation of 25-Hydroxyvitamin D3 and 25-Hydroxyvitamin D2 Levels in Human Plasma Obtained from 758 Japanese Healthy Subjects, J. Nutr. Sci. Vitaminol (Tokyo), 29(3):271-281 (1983). Abstract Only.
Kooienga et al., The effect of combined calcium and vitamin D3 supplementation on serum intact parathyroid hormone in moderate CKD, Am.J.Kidney Dis,. 53: 408-416 (2009).
Koshikawa, et al., Clinical Effect of Intravenous Calcitriol Administration on Secondary Hyperparathyroidism, Nephron; 90:413-423 (2002).
Kovesdy et al., Association of activated vitamin D treatment and mortality in chronic kidney disease, Arch. Intern. Med., 168(4):397-403 (Feb. 2008).
Krishnan et al., The role of vitamin D in cancer prevention and treatment, Rheum. Dis. Clin. North Am., 38(1):161-78 (2012).
Kuro-O, Klotho in chronic kidney disease—what's new?, Nephrol. Dial. Transplant., 4 pp. (2009).
LaClair et al., Prevalence of Calcidiol Deficiency in CKD: A Cross-Sectional Study Across Latitudes in the United States, Am. J. Kidney Dis., 45:1026-1033 (2005).
Lafage et al., Ketodiet, Physiological Calcium Intake and Native Vitamin D Improve Renal Osteodystrophy, Kidney Int., 42:1217-1225 (1992).
Lambert et al., Evidence for Extranrenal Production of 1-alpha, 25-Dihydroxyvitamin D in Man, J. Clin. Invest., 69:722-725 (1982).
Lambrey et al., 24, 25 Dihydroxycalciferol: Assay in Non-Anephric Patients on Chronic Haemodialysis and Assessment of it's Possible Pathophysiological Role in Renal Osteodystrophy Proc Eur Dial Transplant Assoc. 17:548-556 (1980).
Lambrey, Possible Link Between Changes in Plasma 24,25-Dihydroxyvitamin D and Healing of Bone Resorption in Dialysis Osteodrstrophy Metab. Bone Dis. & Rel. Res. 4:25-30 (1982).

Langman et al., 25-Hydroxyvitamin D3 (Calcifediol) Therapy of Juvenile Renal Osteodystrophy: Beneficial Effect on Linear Growth Velocity, J. Pediatrics, 100:815-820 (1982).
Larrosa M. et al., Long-Term Treatment of Hypovitaminosis D. Calcidol or Cholecalciferol? Annals of The Rheumatic Diseases, vol. 64, No. Suppl. 3, Jul. 2005, p. 366.
Lau et al., Vitamin D Therapy of Osteoporosis: Plain Vitamin D Therapy Versus Active Vitamin D Analog (D-Hormone) Therapy, Calcif. Tissue Int., 65:295-306 (1999).
Lee et al., Comparison between calcitriol and calcitriol plus low-dose cinacalcet for the treatment of moderate to severe secondary hyperparathyroidism in chronic dialysis patients, Nutrients, 5(4):1336-48 (2013).
Lehmann et al., Coating of Tablets and Small Particles with Acrylic Resins by Fluid Bed Technology, Int. J. Pharm. Tech. & Prod. Mfr., 2:31-43 (1981).
Lehmann et al., Coating of tablets and small particles with acrylic resins by fluid bed technology, Int. J. Pharm. Technol. Prod. Manuf., 2(4):31-43 (1981).
Letteri et al., Effects of 25-Hydroxycholecalciferol on Calcium Metabolism in Chronic Renal Failure Adv. Exp. Med. Biol. 81:591-601 (1977).
Lips et al., A Global Study of Vitamin D Status and Parathyroid Function in Postmenopausal Women with Osteoporosis: Baseline Data from the Multiple Outcomes of Raloxifene Evaluation Clinical Trial, The Jour. of Clin. Endo. & Meta., 86(3):1212-1221 (2001).
Lo et al., Vitamin D absorption in healthy subjects and in patients with intestinal malabsorption syndromes, Am. J. Clin. Nutr., 42(4):644-9 (1985).
Lomonte et al., Are Low Plasma Levels of 25-(OH) Vitamin D a Major Risk Factor for Hyperparathyroidism Independent of Calcitriol in Renal Transplant Patients? J. Nephrol., 18:96-101 (2005).
Lund et al., Serum 1,25-Dihydroxycholecalciferol in Anephric. Haemodialyzed and Kidney-transplanted Patients, Nephron, 25:30-33 (1980).
Luo et al., 24-Hydroxylase in cancer: impact on vitamin D-based anticancer therapeutics, J. Steroid Biochem. Mol. Biol., 136:252-7 (2013).
Larrosa et al. (Abstract FR10365, Long term treatment of Hypovitaminisis, clacidiol or cholecalcidiol).
Maierhofer et al., Synthesis and Metabolic Clearance of 1,25-Dihydroxyvitamin D as Determinants of Serum Concentrations: a Comparison of Two Methods Journal of Clinical Endocrinology and Metabolism 53:472-475 (1981).
Manni et al., Oral Calcitriol: Comparison Between the Same Weekly Dose Administered as a Single vs. Two Divided Pulsed Doses in Secondary Hyperparathyroidism of Chronic Renal Failure, Ital. J Mineral Electrolyte Metab., 11:61-64 (1997).
Martin et al., 19-Nor-1-α-25-Dihydroxyvitamin $D_2$ (Paricalcitol) Safely and Effectively Reduces the Levels of Intact Parathyroid Hormone in Patients on Hemodialysis, J. Am. Soc. Nephrol., 9:1427-1432 (1998).
Martin-Baez et al., Severe hypocalcaemia post-denosumab, Nefrologia, 33(4):614-5 (2013).
Matsushita et al., Clinical effects of 25-hydroxycholecalciferol in patients with chronic renal failure, J Nutr Sci Vitaminol, 23:257-261 (1977).
Mazouz et al., Risk factors of renal failure progression two years prior to dialysisis Clinical Nephroloby 51(6):355-366 (1999).
Mazur, Effects of 25-OHD3 on Renal Function in Pediatric Patients with Chronic Renal Failure, Mineral Electrolyte Metab. 10:351-358 (1984).
Memmos et al., Response of uremic osteoid to vitamin D, Kidney Int, 21 (Suppl. 11): S50-S54 (1982).
Menon et al., Vitamin D insufficiency and hyperparathyroidism in children with chronic kidney disease, Pedaitr Nephrol, 23:1831-1836 (2008).
Messa et al., Direct In Vivo Assessment of Parathyroid Hormone-Calcium Relationship Curve in Renal Patients, Kidney Int., 46:1713-1720 (1994).
Mimori et al., Clinical significance of the overexpression of the candidate oncogene CYP24 in esophageal cancer, Ann. Oncol., 15(2):236-41 (2004).

(56) References Cited

OTHER PUBLICATIONS

Modem Pharmaceutics 4th ed., Marcel Dekker, Inc., New York, NY, p. 16-21 (2002).
Moe et al., A randomized trial of cholecalciferol versus doxercalciferol for lowering parathyroid hormone in chronic kidney disease, Clin. J.Am.Soc.Nephrol. 5: 299-306 (2010).
Moe et al., Safety and Efficacy of Pulse and Daily Calcitriol in Patients on CAPD: A Randomized Trial, Nephrol. Dial. Transplant., 13:1234-1241 (1998).
Morris, Cats Discriminate Between Cholecalciferol and Ergocalciferol, J. Anim. Physiol. a. Anim. Nutr., 86:229-238 (2002).
Morris, Vitamin D: A Hormone for All Seasons—How Much is Enough? Clin. Biochem. Rev., 26:21-32 (2005).
Motellon et al., Parathyroid hormone-related protein, parathyroid hormone, and vitamin D in hypercalcemia of malignancy, Clin. Chim. Acta, 290(2):189-97 (2000).
Muindi et al., Phamacokinetics of Liquid Calcitriol Formulation in Advanced Solid Tumor Patients: Comparison with Caplet Formulation, Cancer Chemother. Pharmacol., 56:492-496 (2005).
Naik et al., Effects of Vitamin D Metabolites and Analogues on Renal Function, Nephron, 28:17-25 (1981).
Nakanishi et al., The Roles of Vitamin D in Secondary Hyperparathyroidism, [journal in Japanese] 52:1107-1112 (2004).
National Kidney Foundation Guidelines, NKF, Am. J. Kidney Dis., 42(4, Suppl 3):S1-S202 (2003).
NewsWire (https://www.newswire.ca/news-releases/cytochroma-announces-data-presentations-at-american-society-of-hephrologys43rd-annual-meeting-and-scientific-exposition-546289852.html, published Nov. 18, 2010) (Year: 2010).
Norman et al. (eds.), Vitamin D—Gene Regulation, Structure-Function Analysis and Clinical Application: Proceedings of the Eighth Workshop on Vitamin d Paris, France, pp. 765-766, New York: Walter De Gruyter Inc. (1991).
Notice of allowance issued Jul. 10, 2012, in counterpart EPO application 08746908.6.
Office Action (with English translation), Japanese patent application No. 2014-031369, dated Mar. 9, 2015.
Oksa et al., Effects of long-term cholecalciferol supplementation on mineral metabolism and calciotropic hormones in chronic kidney disease, Kidney Blood Press Res., 31: 322-329 (2008).
Olmos et al., Effects of 25-hydroxyvitamin D3 therapy on bone turnover markers and PTH levels in postmenopausal osteoporotic women treated with alendronate, J. Clin. Endocrinol. Metab., 97(12):4491-7 (2012).
Opko Health Inc., Safety/Efficacy Study of CTAP101 in Chronic Kidney Disease Subjects With Secondary Hyperparathyroidism (SHPT), <https://clinicaltrials.govict2/show/NCT01219855> Oct. 13, 2010.
Package insert for Hectorol (doxercalcitol capsules), Genzyme (2011).
Package insert for Zemplar (paricalcitol) Capsules, Abbott (2011).
Pak et al., Treatment of Vitamin D-Resistant Rickets With 25-Hydroxycholecalciferol, Arch Intern Med, 129:894-899 (1972).
Parfitt et al., Calcitriol but no Other Metabolite of Vitamin D is Essential for NormalBone Growth and Development in the Rat, J. Clin. Invest., 73:576-586 (1984).
Patel et al., Glomerular Filtration Rate is a Major Determinant of the Relationship Between 25-Hydroxyvitamin D and Parathyroid Hormone, Calcif. Tissue Int., 80:221-226 (2007).
Peacock et al., Effect of Calcium or 25OH Vitamin D3 Dietary Supplementation on Bone Loss at the Hip in Men and Women over the Age of 60 The Journal of Clinical Endocrinology & Metabolism, 85(9):3011-3019 (2007).
Perrie, Pharmaceutics: Drug Delivery and Targeting, Second Edition, Chapter 1 (2012).
Petkovich et al., CYP24A1 and Kidney Disease, Current Opin. in Nephrology and Hypertension, 20:337-344 (2011).
Phadnis et al., Direct, Rapid Effects of 25-Hydroxyvitamin D3 on Isolated Intestinal Cells, J. Cell. Biochem., 90:287-293 (2003).
Posner et al., Vitamin D Analogues Targeting CYP24 in Chronic Kidney Disease, J. Steroid Biochem and Mol. Biol., 121:13-19 (2010).
Pourgholami et al., 1, 25-Dihydroxyvitamin D3 Dissolved in Lipiodol Produces a Sustained Antiproliferative Effect in the Human Hepatoblastoma Cell Line HepG2, Anticancer Res., 20:723-728 (2000).
Pourgholami et al., In Vitro Antiproliferative Activity of a Medium-Chain Triglyceride Solution of 1, 25-Dihydroxyvitamin $D_3$ in HepG2 Cells, Anticancer Res., 20:4257-4260 (2000).
Prescribing Information for Calderol® calcifediol capsules (1988).
Prescribing Information for Hectorol® (doxercalciferol capsules), Genzyme (2011).
Prescribing information for Zemplar® (paricalcitol) Capsules, Abbott (2011).
Querfeld et al., Vitamin D deficiency and toxicity in chronic kidney disease: in search of the therapeutic window, Pediatr. Nephrol., 25(12):2413-30 (Dec. 2010).
Rabbani, Molecular mechanism of action of parathyroid hormone related peptide in hypercalcemia of malignancy: therapeutic strategies (review), Int. J. Oncol., 16(1):197-206 (2000).
Rambeck et al., Biological Activity of 1α,25-Dihydroxyergocalciferol in Rachitic Chicks and in Rats, Izviak, 54(2/3):135-139 (1984).
Rapuri, P.B. et al., Effect of Vitamins D2 and D3 Supplement Use on Serum 25-OHD Concentration in Elderly Women in Summer and Winter, Calcified Tissue International, 74(2):150-156 (2004).
Ravani et al., Vitamin D levels and patient outcome in chronic kidney disease, Kidney Int., 75(1):88-95 (Jan. 2009).
Recker et al., The Efficacy of Calcifediol in Renal Osteodystrophy, Arch. Intern. Med., 138:857-863 (1978).
Reddy et al., Abstracts Sixth Annual Scientific Meeting of the American Society for Bone and Mineral Research, 36:524 (1984).
Reichel et al., Calcium Metabolism in Early Chronic Renal Failure: Implications for the Pathogenesis of Hyperparathyroidism, Nephrol. Dial. Transplant., 6:162-169 (1991).
Reichel et al., Intermittent Versus Continuous Administration of 1,25-dihydroxyvitamin D3 in experimental renal hyperparathyroidism, Kidney Int., 44:1259-1265 (1993).
Reichel, Current treatment options in secondary renal hyperparathyroidism, Nephrol Dial Transplant 21:23-28 (2006).
Richard et al., PTHrP gene expression in cancer: do all paths lead to Ets?, Crit. Rev. Eukaryot. Gene Expr., 15(2):115-32 (2005).
Ritter et al., 25-Hydroxyvitamin D3 suppresses PTH synthesis and secretion by bovine parathyroid cells, Kidney Int., 70:654-659 (2006).
Rix et al., Effect of 18 Months of Treatment with Alfacalcidol on Bone in Patients with Mild to Moderate Chronic Renal Failure, Nephrol Dial Transplant, 19:870-876 (2004).
Rocaltrol (Registered) Complete Product Information, Roche, Jul. 27, 2004.
Rotuba marketing phthalate-free cellulosic, Plastic News, Nov. 26, 2007.
Rucker et al., Vitamin D insufficiency and treatment with oral vitamin D3 in northern-dwelling patients with chronic kidney disease, J.Nephrol. 22: 75-82 (2009).
Russell et al., Therapeutic Effects of 25-Hydroxyvitamin D3 on Renal Osteodystrophy, Mineral Electrolyte Metab., 1:129-138 (1978).
Rutherford et al., Effect of 25-Hydroxycholecalciferol on Calcium Absorption in Chronic Renal Disease, Kidney International, 8:320-324 (1975).
Saab et al., Prevalence of Vitamin D Deficiency and the Safety and Effectiveness of Monthly Ergocalciferol in Hemodialysis Patients, Nephron Clin. Pract., 105:c132-c138 (2007).
Sanchez, Prevention and Treatment of Renal Osteodystrophy in Children With Chronic Renal Insufficiency and End-Stage Renal Disease, Seminars in Nephrology, 21:441-450 (2001).
Saseen et al., Dual calcium-channel blocker therapy in the treatment of hypertension, Ann Pharmacother., 30(7-8): 802-10 (1996).
Sato et al., Increased 1,25-(OH)2D2 concentration in a patient with malignancy-associated hypercalcemia receiving intravenous hyperalimentation inadvertently supplemented with vitamin D2, Intern. Med., 32(11):886-90 (1993).

(56) References Cited

OTHER PUBLICATIONS

Schmidt, Measurement of 25-Hydroxyvitamin D Revisited, Clinical Chemistry, 52(12):2304-2305 (2006).
Schwartz et al., Extended-release calcifediol (ERC) effectively increased serum 25-hydroxyvitamin D levels in breast and prostate cancer patients without significant impact on serum calcium or phosphorus, Opko Renal (2018).
Sebert et al. Comparative effects of equal doses of vitamin D2 and vitamin D3 for the correction of vitamin D deficiency in the elderly in Norman et al. (eds.), Vitamin D—Gene Regulation, Structure-Function Analysis and Clinical Application: Proceedings of the Eighth Workshop on Vitamin d Paris, France, pp. 765-766, New York: Walter De Gruyter Inc. (1991).
Sebert et al., Effets A Long Terme D'Une Association De 25-Hydroxycholécalciférol et de 1-Alpha-Hydroxycholécalciférol Sur L'Ostéodystrophie Des Hémodialysés Chroniques Rev. Rhum Mal Osteoartic 48(7-9):535-541 (1981).
Sebert et al., Limit by Hyperphosphatemia of the Usefulness of Vitamin D Metabolites (1 alpha-Hydroxycholecalciferol and 25-Hydroxycholecalciferol) in the Treatment of Renal Osteodystrophy, Metab. Bone Dis. & Rel. Res., 2:217-222 (1980).
Segersten et al., Potentiating effects of nonactive/active vitamin D analogues and ketoconazole in parathyroid cells, Clin. Endocrinol., vol. 66, No. 3, Mar. 1, 2007 (Mar. 1, 2007), pp. 399-404.
Sekkarie, The Impact of Over-the-counter Vitamin D Supplementals on Vitamin D and Parathyroid Hormone Levels in Chronic Kidney Disease, Clin. Nephrology, 65:91-96 (2006).
Sensipar (cinacalcet) prescriptioninformation, revised Aug. 2011.
Sensipar package insert (Year: 2004).
Shah et al., Prevalence and correction of 25(OH) vitamin D deficiency in peritoneal dialysis patients, Peritoneal Dialysis Int., 25:362-366 ( 2005).
Shi et al., Preparation of Chitosan/Ethylcellulose Complex Microcapsule and its Application in Controlled Release of Vitamin $D_2$, Biomaterials, 23:4469-4473 (2002).
Sicinski et al., Synthesis of 1 alpha, 25-Dihydroxyvitamin D2, Its 24 Epimer and Related Isomers, and Their Binding Affinity for the 1, 25-Dihydroxyvitamin D3 Receptor, Bioorganic Chemistry, 13: 158-169 (1985).
Singh et al., C-3 Epimers Can Account for a Significant Proportion of Total Circulating 25-Hydroxyvitamin D in Infants, Complicating Accurate Measurement and interpretation of Vitamin D Status, J. Clin. Endo. & Metabol., 91(8):3055-3061 (2006).
Sirvent et al., Extreme hypocalcaemia and hyperparathyroidism following denosumab. Is this drug safe in chronic kidney disease?, Nefrologfa (Madrid), 34(4): 542-544 (2014).
Sitrin et al., Comparison of vitamin D and 25-hydroxyvitamin D absorption in the rat, Am. J. Physiol., 242(4):G326-32 (1982).
Sjoden, et al., 1α-Hydroxyvitamin D2 is Less Toxic than 1α-Hydroxyvitamin D3 in the Rat, Society for Experimental Biology and Medicine, 179: 432-436 (1985).
Skelly et al., In vitro and in vivo testing an correlation for oral controlled/modified-release dosage forms. Pharm. Res., 7(9):975-82 (1990).
Skugor et al., Evolution and current state of assays for parathyriod hormone, Biochemia Medica, vol. 20, No. 2, 2010, pp. 221-228.
Slatopolsky et al., Differential Effects of 19-nor-1,25-$(OH)_2D_2$ and 1α-Hydroxyvitamin $D_2$ on Calcium and Phosphorus in Normal and Uremic Rats, Kidney International, 62:1277-1284 (2002).
Somerville et al., Resistance to Parathyroid Hormone in Renal Failure: Role of Vitamin D Metabolites, Kidney Int., 14:245-254 (1978).
Sommerfeldt et al., Metabolism of Orally Administered [3H]Ergocalciferol and [3H]Cholecalciferol by Dairy Calves, J. Nutr., 113:2595-2600 (1983).
Sosa et al., The Effect of 25-dihydroxyvitamin D on the Bone Mineral Metabolism of Elderly Women with Hip Fracture, Rheumatology, 39:1263-1268 (2000).
Soyfoo et al., Non-malignant causes of hypercalcemia in cancer patients: a frequent and neglected occurrence, Support Care Cancer, 21(5):1415-9 (2013).
Sprague et al., Modified-release calcifediol effectively controls secondary hyperparathyroidism associated with vitamin D insufficiency in chronic kidney disease, Am. J. Nephrol., 40(6):535-45 (2015).
Sprague et al., Use of Extended-Release Calcifediol to Treat Secondary Hyperparathyroidism in Stages 3 and 4 Chronic Kidney Disease, Am. J. Nephrol., 44(4):316-25 (2016).
Stamp et al., Comparison of Oral 25-Hydroxycholecalciferol, Vitamin D, and Ultraviolet Light as Determinants of Circulating 25-Hydroxyvitamin D, The Lancet, 1341-1343 (Jun. 25, 1977).
Stamp, Intestinal Absorption of 25-hydroxycholecalciferol, The Lancet, 121-123 (1974).
Stavroulopoulos et al., Relationship between vitamin D status, parathyroid hormone levels and bone mineral density in patients with chronic kidney disease stages 3 and 4, Nephrology (Carlton), 13(1):63-7 (Feb. 2008).
Stein et al., An Update on the Therapeutic Potential of Vitamin D Analogues, Expert Opin. Investig. Drugs, 12:825-840 (2003).
Stubbs et al., Cholecalciferol supplementation alters calcitriol-responsive monocyte proteins and decreases inflammatory cytokines in ESRD, J.Am.Soc. Nephrol., 21: 353-361 (2010).
Stumpf, The Dose Makes the Medicine, Drug Discovery Today, 11:550-555 (2006).
Supplementary European Search Report for Application No. 09729007.6, dated Apr. 18, 2011.
Szycher, Szycher's Dictionary of Biomaterials and Medical Devices, pp. 20, 48, 127, Lancaster, Penn: Technomic Publishing Co., Inc. (1992).
Somjen et al., Nonhypercalcemic Analogs of Vitamin D Stimulate Creatine Kinase B Activity in Osteoblast-Like ROS 17/2.8 Cells and Up-Regulate Their Responsiveness to Estrogens, Steroids, 63:340-343 (1998).
Tamez et al., Vitamin D reduces left atrial volume in patients with left ventricular hypertrophy and chronic kidney disease, Am. Heart J., 164(6):902-9.e2 (Dec. 2012).
Taylor et al., Interrelationship of Serum 25-Hydroxyvitamin D3 and 1,25-Dihydroxyvitamin D in Juvenile Renal Osteodystrophy after Therapy with 25-Hydroxyvitamin D3, Metab. Bone Dis. & Rel. Res., 4:255-261 (1982).
Taylor et al., The absence of 24,25-dihydroxycholecalciferol in anephric patients, Clin.Sci.Mol.Med.Suppl., 55: 541-547 (1978).
Taylor, CM, 24,25-Dihydroxyvitamin D in Human Serum. In: Vitamin D. Basic Research and Clinical Applications, pp. 197-203. Walter de Gruyter, New York (1979).
Tebben et al., Elevated fibroblast growth factor 23 in women with malignant ovarian tumors, Mayo Clin. Proc., 80:745-51 (2005).
Teitelbaum et al., Calcifediol in Chronic Renal Insufficiency JAMA, 235(2):164-167 (1976).
Teitelbaum et al., Tetracycline fluorescence in uremic and primary hyperparathyroid bone, Kidney Int., 12:366-372 (1977).
Terrie, Monitoring Combination Drug Therapy, Pharmacy Times, published Jan. 18, 2010., Jan. 19, 2010.
Thomas et al., Hypovitaminosis D in Medical Inpatients, NEJM, 338:777-783 (1998).
Thombre, Assessment of the feasibility of oral controlled release in an exploratory development setting, Drug Discovery Today, 10(17): 1159-1166 (2005).
Tokmak et al., High-dose cholecalciferol to correct vitamin D deficiency in haemodialysis patients, Nephrol.Dial. Transplant., 23: 4016-4020 (2008).
Tomida et al., Serum 25-hydroxyvitamin D as an independent determinant of 1-84 PTH and bone mineral density in non-diabetic predialysis CKD patients, Bone, 44(4):678-83 (Apr. 2009).
Trakarnvanich et al., Effect of high dose ergocalciferol in chronic kidney disease patients with 25-hydroxyvitamin D deficiency, J.Med. Assoc. Thai. 93: 885-891 (2010).
Tsuji, et al. A New and Convenient Synthesis of 1α,25-Dihydroxyvitamin D2 and It 24R-Epimer, Bull. Chem. Soc. Jpn., 62:10 pp. 3132-3137 (1989).

(56) References Cited

OTHER PUBLICATIONS

Tuohimaa et al., Both high and low levels of blood vitamin D are associated with a higher prostate cancer risk: a longitudinal, nested case-control study in the Nordic countries, Int. J. Cancer, 108(1):104-8 (2004).
U.S. Appl. No. 12/597,230, Nonfinal Office Action, mailed Dec. 13, 2019.
U.S. Appl. No. 15/918,620, Notice of Allowance, dated Nov. 29, 2019.
U.S. Appl. No. 15/918,620, Notice of Allowance, Jan. 27, 2020.
U.S. Appl. No. 16/171,100, Nonfinal Office Action, dated Dec. 30, 2019.
US FDA Clinical Review and Evaluation of NDA for Calderol® calcifediol capsules (believed to be available circa 1983).
US FDA Summary of Basis of Approval for Calderol® calcifediol capsules (believed to be available circa 1980).
Van Weelden et al., Apoptotic Regression of MCF-7 Xenografts in Nude Mice Treated with the Vitamin $D_3$ Analog, EB1089, Endocrinology, 139:2102-2110 (1998).
Verberckmoes et al., Osteodystrophy of Dialysed Patients Treated with Vitamin D, Proc Eur Dial Transplant Assoc., 10(0): 217-226 (1973).
Vieth, Vitamin D Supplementation, 25-Hydroxyvitamin D Concentrations, and Safety, Am. J. Clin. Nutr., 69:842-856 (1999).
Vieth, What is the optimal vitamin D status for health? Prog. Biophys. Mol. Biol., 92:26-32 (2006).
Wagner et al., The ratio of serum 24,25-dihydroxyvitamin D(3) to 25-hydroxyvitamin D(3) is predictive of 25-hydroxyvitamin D(3) response to vitamin D(3) supplementation, J. Steriod Biochem. Mal. Biol., 126(3-5):72-7 (Sep. 2011).
Wang-Gillam et al., Evaluation of vitamin D deficiency in breast cancer patients on bisphosphonates, Jul. 1, 2008, Oncologist, 821-7, 13(7).
Wise (ed.), Handbook of Pharmaceutical Controlled Release Technology, An Overview of Controlled Release Systems, Chapter 22, pp. 431-445, 461-463; Research and Development Aspects of Oral Controlled-Release Dosage Forms, Chapter 23, pp. 465-473, New York: Marcel Dekker, Inc. 3 (2000).
Witmer et al., Effects of 25-hydroxycholecalciferol on bone lesions of children with terminal renal failure Kidney International 10:395-408 (1976).
Wootton, Improving the Measurement of 25-Hydroxyvitamin D, Clin Biochem Rev, 26:33-36 (2005).
Written Opinion for Application No. PCT/IB2008/003480, dated Mar. 31, 2009.
Written Opinion for Application No. PCT/US2007/061521, dated Jul. 17, 2007.
Written Opinion for Application No. PCT/US2014/28132, dated Jun. 17, 2014.
Written Opinion of the International Searching Authority for corresponding international application No. PCT/US2007/071791 (Feb. 5, 2008).
Yanoff et al., The Prevalence of Hypovitaminosis D and Secondary Hyperparathyroidism in Obese Black Americans, Clin. Endocrinol. (Oxf), 64(5):523-529 (2006).
Yudianti et al., Effect of water soluble polymer on structure and mechanical properties of bacterial cellulose composites, J. Appl. Sci., 8(1):177-180 (2008).
Yueh-Ting et al: Comparison between Calcitriol and Caltiriol Plus Low-Dose Cinacalcet for the Treatment of Moderate to Severe Secondary Hyperparathyroidism in Nutrients, vol. 5, No. 4, Apr. 19, 2013 (Apr. 19, 2013), pp. 1336-1348.
Zemplar (Registered) (paricalcitol) Capsules, Final Agreed Upon Label (FDA, May 5, 2009).
Zerwekh et al., Extra-Renal Production of 24,25-Dihydroxyvitamin D in Chronic Renal Failure During 25 Hydroxyvitamin D3 Therapy, Kidney Int., 23:401-406 (1983).
Zerwekh, Blood biomarkers of vitamin D status, The American Journal of Clinical Nutrition, vol. 87Suppl., 2008, pp. 1087S-1091S.
Zisman et al., Impact of Ergocalciferol Treatment of Vitamin D Deficiency on Serum Parathyroid Hormone Concentrations in Chronic Kidney Disease, Am. J. Nephrol., 27:36-43 (2007).
Zucchelli et al., Therapeutic effects of 25-hydroxycholecalciferol and sodium etidronate on renal osteodystrophy, Mineral. Electrolyte Metab. 7: 86-96 (1982).
Zuradelli et al., High incidence of hypocalcemia and serum creatinine increase in patients with bone metastases treated with zoledronic acid, Oncologist, 14(5):548-56 (2009).

* cited by examiner

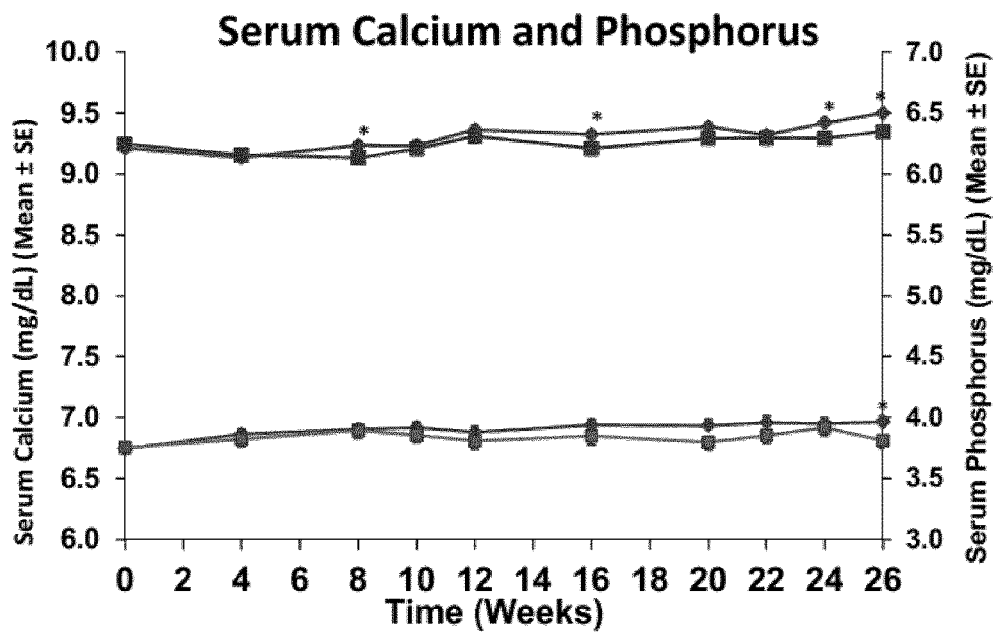
FIGURE 6A
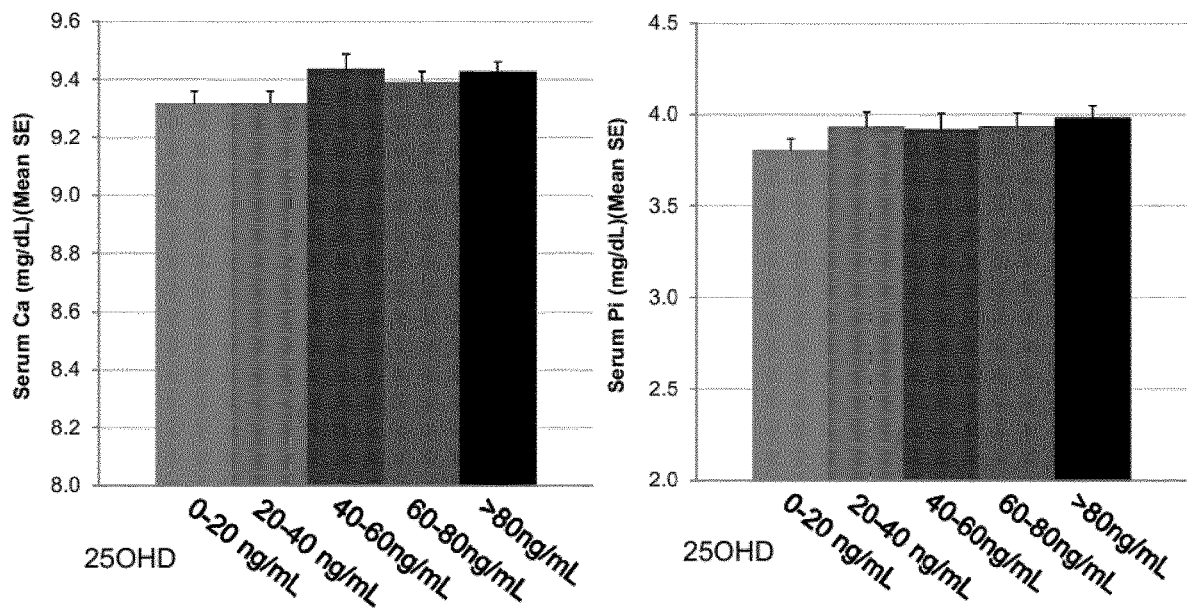
FIGURE 6B
FIGURE 6C

METHODS OF VITAMIN D TREATMENT

CROSS-REFERENCE TO RELATED APPLICATION

This is a Continuation of U.S. application Ser. No. 16/089,235, filed Sep. 27, 2018, which is a U.S. National Phase of International Application No. PCT/EP2017/57282, filed Mar. 28, 2019, which claims the benefit under 35 U.S.C. § 119 (e) of U.S. Provisional Patent Application No. 62/314,359 filed Mar. 28, 2016, which are hereby claimed, and the disclosures thereof are incorporated herein by reference.

BACKGROUND

The Vitamin D metabolites known as 25-hydroxyvitamin $D_2$ and 25-hydroxyvitamin $D_3$ (collectively referred to as "25-hydroxyvitamin D") are fat-soluble steroid prohormones that contribute to the maintenance of adequate levels of Vitamin D hormones, calcium and phosphorus in the bloodstream. The prohormone 25-hydroxyvitamin $D_2$ is produced from Vitamin $D_2$ (ergocalciferol), and 25-hydroxyvitamin $D_3$ (calcifediol) is produced from Vitamin $D_3$ (cholecalciferol), primarily by one or more enzymes located in the liver. The two prohormones also can be produced outside of the liver from Vitamin $D_2$ and Vitamin $D_3$ (collectively referred to as "Vitamin D") in certain cells, such as enterocytes, which contain enzymes identical or similar to those found in the liver.

The Vitamin D prohormones are further metabolized in the kidneys by the 1α-hydroxylase enzyme CYP27B1 into potent hormones. The prohormone 25-hydroxyvitamin $D_2$ is metabolized into a hormone known as 1α,25-dihydroxyvitamin $D_2$ (ercalcitriol); likewise, 25-hydroxyvitamin $D_3$ is metabolized into 1α,25-dihydroxyvitamin $D_3$ (calcitriol). Production of these hormones from the prohormones also can occur outside of the kidney in cells which contain the required enzyme(s). Rapidly rising or excessive intracellular levels of Vitamin D hormones stimulate the expression of the 24-hydroxylase enzyme CYP24A1 in cells which contain the Vitamin D receptor (VDR). CYP24A1 catabolizes 25-hydroxyvitamin D to form 24,25-dihydroxyvitamin D as the major catabolite.

The Vitamin D hormones have essential roles in human health which are mediated by intracellular Vitamin D receptors (VDRs). The Vitamin D hormones participate in the regulation of cellular differentiation and growth, parathyroid hormone (PTH) secretion by the parathyroid glands, and normal bone formation and metabolism. In particular, the Vitamin D hormones regulate blood calcium levels by controlling the absorption of dietary calcium and phosphorus by the small intestine and the reabsorption of calcium by the kidneys. Under normal conditions, actions of Vitamin D on stimulating intestinal calcium absorption predominate, such that dietary calcium is the main source of serum calcium. However, if dietary calcium or Vitamin D is insufficient, the parathyroid gland increases secretion of PTH to enhance calcium mobilization from bone to maintain serum calcium levels. Excessive Vitamin D hormone levels, whether transient or prolonged, can lead to side effects including abnormally elevated urine calcium (hypercalciuria), blood calcium (hypercalcemia), blood phosphorus (hyperphosphatemia), and adynamic bone disease. Vitamin D hormones are also required for the normal functioning of the musculoskeletal, immune and renin-angiotensin systems. Numerous other roles for Vitamin D hormones are being postulated and elucidated, based on the documented presence of intracellular VDRs in nearly every human tissue.

Left untreated, inadequate Vitamin D supply can cause serious bone disorders, including rickets and osteomalacia, and may contribute to the development of many other disorders including osteoporosis, non-traumatic fractures of the spine and hip, obesity, diabetes, muscle weakness, immune deficiencies, hypertension, psoriasis, and various cancers.

The Institute of Medicine (IOM) of the National Academy of Sciences has concluded that an Adequate Intake (AI) of Vitamin D for a healthy individual ranges from 200 to 600 IU per day, depending on the individual's age and sex (Standing Committee on the Scientific Evaluation of Dietary Reference Intakes, *Dietary reference intakes: calcium, phosphorus, magnesium, vitamin D, and fluoride*. Washington, D.C.: National Academy Press (1997), incorporated by reference). The AI for Vitamin D was defined primarily on the basis of a serum 25-hydroxyvitamin D level sufficient to prevent Vitamin D deficiency rickets or osteomalacia (or greater than or equal to 11 ng/mL). The IOM also established a Tolerable Upper Intake Level (UL) for Vitamin D of 2,000 IU per day, based on evidence that higher doses are associated with an increased risk of hypercalciuria, hypercalcemia and related sequelae, including cardiac arrhythmias, seizures, and generalized vascular and other soft-tissue calcification. An accepted upper limit for serum 25-hydroxyvitamin D in healthy subjects is about 100 ng/mL or 250 nmol/L (see, e.g., Jones, G, *Am. J. Clin. Nutr.* 88(suppl): 582S-6S, 2008; Holick, M F, *Ann. Epidemiol.* 19(2): 73-78, 2009).

However, the definition of Vitamin D insufficiency (VDI) in general, and specifically in subjects having Chronic Kidney Disease (CKD), is controversial. The IOM has defined VDI as total 25-hydroxyvitamin D below 20 ng/mL, whereas the Kidney Disease Outcomes Quality Initiative (KDOQI), Kidney Disease Improving Global Outcomes, (KDIGO) and Endocrinology clinical practice guidelines have defined VDI as 25-hydroxyvitamin D below 30 ng/mL (National Kidney Foundation KDOQI Guidelines, 2003; National Kidney Foundation KDIGO Guidelines, 2009; Holick et al., *J Clin Endocrinol Metab* 96(7):1911-30, 2011). The appearance of the 25-hydroxyvitamin D (25(OH) $D_3$) catabolite, 24,25-dihydroxyvitamin D (24,25(OH)$_2$D), may be a useful measure of sufficiency, with VDI defined by a ratio of 25(OH)$D_3$:24,25(OH)$_2D_3$ of greater than 20 (Kaufmann et al., *J Clin Endocrinol Metab* 99(7):2567-2574, 2014). Serum levels of 25-hydroxyvitamin D and 24,25-dihydroxyvitamin D are strongly correlated, with the catabolism of 25-hydroxyvitamin D to 24,25-dihydroxyvitamin D increasing as serum 25-hydroxyvitamin D rises in normal (i.e., non-CKD) populations (Berg et al., *Clin Chem* 61(6):877-884, 2015; Wagner at al., *J Ster Biochem Mol Bio* 126:72-22, 2011). While CYP24 is typically decreased in normal subjects having VDI, in subjects with CKD, elevated levels of CYP24 have been observed (Helvig et al., *Kidney Int* 78(5):463-72, 2010; International Patent Application No. PCT/US2009/39355).

Regardless of how VDI is defined, conventional oral Vitamin D supplements are far from ideal for achieving and maintaining optimal blood 25-hydroxyvitamin D levels. These preparations typically contain 400 IU to 5,000 IU of Vitamin $D_3$ or 50,000 IU of Vitamin $D_2$ and are formulated for quick or immediate release in the gastrointestinal tract. When administered at chronically high doses, as is often required for Vitamin D repletion in CKD, these products have significant, and often severe, limitations. Additionally, prior uses of immediate-release formulations of calcifediol have not been demonstrated to be effective for suppressing elevated PTH in clinical studies conducted with patients with CKD Stage 3 or Stage 4.

Controlled release oral formulations and gradually administered parenteral (e.g., slow push IV) formulations of 25-hydroxyvitamin $D_2$ and/or 25-hydroxyvitamin $D_3$ can be administered to treat 25-hydroxyvitamin D insufficiency and deficiency without supraphysiological surges in intraluminal, intracellular and blood levels of 25-hydroxyvitamin D and their consequences; without causing substantially increased catabolism of the administered 25-hydroxyvitamin D; and, without causing serious side effects associated with Vitamin D supplementation. The controlled release and gradually administered formulations effectively lower PTH levels without undesirable increases in serum calcium and serum phosphorus and are therefore useful for treating secondary hyperparathyroidism, for example in CKD patients. See International Patent Application Nos. PCT/US2007/061521, PCT/US2008/061579, PCT/US2014/028132, and PCT/EP2015/068219, incorporated herein by reference.

The controlled released compositions provide substantially increased absorption of 25-hydroxyvitamin D via transport on Vitamin D binding protein (DBP) and decreased absorption via transport in chylomicrons. The compositions also provide maintenance of substantially constant blood levels of 25-hydroxyvitamin D during a 24-hour post-dosing period. By providing a gradual, sustained and direct release of 25-hydroxyvitamin $D_2$/25-hydroxyvitamin $D_3$ and absorption preferentially to circulating DBP (rather than to chylomicrons), blood, intraluminal and intracellular 25-hydroxyvitamin D concentration spikes, i.e., supraphysiologic levels and related unwanted catabolism can be mitigated or eliminated. Furthermore, by providing a gradual and sustained release, serum levels of 25-hydroxyvitamin D can be increased and maintained more predictably than by administration of immediate release formulations, allowing for a consistent dosage and reducing or eliminating the need for frequent patient monitoring.

SUMMARY

The present disclosure relates to methods of treating vitamin D-responsive diseases by raising 25-hydroxyvitamin D (e.g., as serum total 25-hydroxyvitamin D, or calcifediol) to high levels, and concomitantly raising 1,25-dihydroxyvitamin D (e.g., as serum total 1,25-dihydroxyvitamin D, or calcitriol) to high levels, without inducing hypercalcemia.

The present disclosure also relates to methods of treating vitamin D insufficiency and secondary hyperparathyroidism in patients having CKD. In one aspect, a method of treating secondary hyperparathyroidism in a patient having CKD comprises administering to the patient repeat doses of 25-hydroxyvitamin D effective to raise the patient's serum 25-hydroxyvitamin D level to greater than 90 ng/ml. In another aspect, a method of treating vitamin D insufficiency in a patient having CKD comprises administering to the patient repeat doses of 25-hydroxyvitamin D effective to control the patient's serum ratio of 25-hydroxyvitamin D to 24,25-dihydroxyvitamin D to less than 20. In still another aspect, a method of treating secondary hyperparathyroidism in a patient having CKD comprises administering to the patient repeat doses of 25-hydroxyvitamin D effective to raise the patient's serum 25-hydroxyvitamin D level to greater than 90 ng/ml and to control the patient's serum ratio of 25-hydroxyvitamin D to 24,25-dihydroxyvitamin D to less than 20.

The present disclosure also relates to methods of administering an extended release dosage form of 25-hydroxyvitamin D, optionally including a waxy controlled release agent, an emulsifier, an absorption enhancer, an oily vehicle, and a stabilizing agent; to a patient in need thereof, comprising administering repeat doses of the extended release oral dosage form to the subject effective to achieve one or more of the following: (1) a baseline-adjusted Cmax for 25-hydroxyvitamin $D_3$ of about 5 ng/mL to about 150 ng/mL; (2) a baseline-adjusted Tmax for 25-hydroxyvitamin $D_3$ of about 5 days to about 60 days; (3) a baseline-adjusted $AUC_{0\text{-}6 \ weeks}$ for 25-hydroxyvitamin $D_3$ of about 100 ng·d/mL to about 3300 ng·d/mL; (4) a baseline-adjusted Cmax for 1,25-dihydroxyvitamin D of about 0.1 pg/mL to about 50 pg/mL; (5) a baseline-adjusted Tmax for 1,25-dihydroxyvitamin D of about 1 days to about 44 days; (6) a baseline-adjusted $AUC_{0\text{-}6 \ weeks}$ for 1,25-dihydroxyvitamin D of about 1 g·d/mL to about 1300 g·d/mL; (7) an increase in mean serum 25-hydroxyvitamin D of about 1 ng/mL/week to about 7 ng/mL/week; (8) an increase in mean serum 1,25-dihydroxyvitamin D of about 1 to about 10 pg/mL/week; (9) a mean steady state serum 25-hydroxyvitamin D level of about 50 ng/mL to about 55 ng/mL; (10) a reduction in plasma intact PTH from baseline of about 30 pg/mL to about 80 pg/mL; (12) a steady state serum 25-hydroxyvitamin D level of greater than about 50 ng/mL to about 100 ng/mL; (13) an increase in serum 1,25-dihydroxyvitamin D from baseline of at least about 10 pg/mL; (14) an increase in serum calcium from baseline of 0 to about 0.3 mg/dL; (15) an increase in serum phosphorous from baseline of 0 to about 0.3 mg/dL; (16) a decrease in serum BSAP from baseline of at least about 10 U/L; (17) a decrease in serum CTX-1 from baseline of at least about 100 pg/mL; (18) a decrease in serum P1NP from baseline of at least about 30 ng/mL; and (19) a decrease in plasma iPTH from baseline of about 15% to about 40%.

In any of the methods described herein, the patient optionally has CKD Stage 1, 2, 3, 4, or 5. In various embodiments, the method comprises administering repeat doses of 25-hydroxyvitamin D in an amount effective to increase the patient's serum 25-hydroxyvitamin D level to greater than 100 ng/mL, greater than 125 ng/mL, greater than 150 ng/mL, greater than 175 ng/mL, or greater than 200 ng/mL, without causing hypercalcemia, hyperphosphatemia, and/or hypercalciuria. The method can include repeat dosing to achieve a serum 25-D level in a range of about 120 ng/mL to about 200 ng/mL, or about 120 ng/mL to about 160 ng/mL, or about 150 ng/mL to about 200 ng/mL, e.g. in Stage 5 CKD patients on dialysis. Optionally, a method of the disclosure comprises administering repeat doses of 25-hydroxyvitamin D in an amount effective to control the patient's serum ratio of 25-hydroxyvitamin D to 24,25-dihydroxyvitamin D to less than 20, less than 19, less than 18, less than 17, less than 16, less than 15, less than 14, less than 13, less than 12, less than 11, or less than 10.

For the methods described herein, optional features, including but not limited to components, compositional ranges thereof, substituents, conditions, and steps, are contemplated to be selected from the various aspects, embodiments, and examples provided herein. Further aspects and advantages will be apparent to those of ordinary skill in the art from a review of the following detailed description, taken in conjunction with the drawings. While the methods are susceptible of embodiments in various forms, the description hereafter includes specific embodiments with the understanding that the disclosure is illustrative and is not intended to limit the invention to the specific embodiments described herein.

BRIEF DESCRIPTION OF THE DRAWINGS

FIG. 6A shows the mean (±SE) serum calcium (target <9.8 mg/dL) and serum phosphorus (target <5.5 mg/dL) in subjects administered a placebo (squares) or an extended release formulation of 25-hydroxyvitamin $D_3$ (diamonds) for 26 weeks. FIG. 6B shows the mean (±SE) serum calcium (mg/dL), and FIG. 6C shows the mean (±SE) serum phosphorus, compared to the serum total 25-hydroxyvitamin D level.

DETAILED DESCRIPTION

Figure 1A:
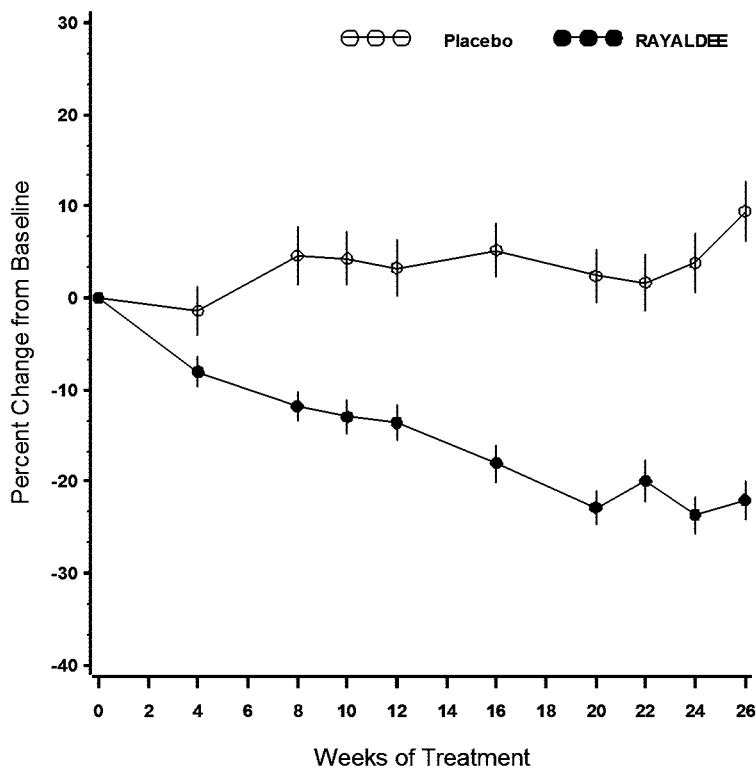
FIG. 1A shows the mean (±SE) change from baseline in plasma iPTH in subjects administered a placebo (open circles) or an extended release formulation of 25-hydroxyvitamin $D_3$ (closed circles) for 26 weeks.

The present disclosure relates to methods of administering vitamin D compounds, and methods of treating vitamin-D responsive diseases.

The present disclosure also relates to methods of treating Vitamin D insufficiency and secondary hyperparathyroidism in patients having Chronic Kidney Disease (CKD). In various embodiments, the methods are used to treat patients having CKD Stage 1, Stage 2, Stage 3, Stage 4, or Stage 5, or a mixed patient population having a combination of any of the foregoing. In one aspect, a method of the disclosure is used to treat a patient having CKD Stage 3 or Stage 4. In another aspect, a method of the disclosure is used to treat a patient having CKD Stage 5, e.g., a hemodialysis patient. Optionally, the patient having CKD has a serum total 25-hydroxyvitamin D concentration of less than 30 ng/mL.

The following definitions may be useful in aiding the skilled practitioner in understanding the disclosure. Unless otherwise defined herein, scientific and technical terms used in the present disclosure shall have the meanings that are commonly understood by those of ordinary skill in the art.

As used herein, the term "comprising" indicates the potential inclusion of other agents, elements, steps, or features, in addition to those specified.

As used herein, the term "25-hydroxyvitamin D" refers to one or more of 25-hydroxyvitamin $D_2$, 25-hydroxyvitamin $D_3$ (also known as calcifediol, calcidiol, and 25-hydroxycholecalciferol), 25-hydroxyvitamin $D_4$, 25-hydroxyvitamin $D_5$, 25-hydroxyvitamin $D_7$, analogs of the foregoing, and combinations thereof. It is specifically contemplated that in any embodiment described herein, 25-hydroxyvitamin D can include 25-hydroxyvitamin $D_3$, 25-hydroxyvitamin $D_2$, or a combination of 25-hydroxyvitamin $D_3$ and 25-hydroxyvitamin $D_2$. For example, it is specifically contemplated that in any embodiment described herein, 25-hydroxyvitamin D can include 25-hydroxyvitamin $D_3$. Serum 25-hydroxyvitamin D and serum total 25-hydroxyvitamin D refer to the total of 25-hydroxyvitamin $D_2$ and 25-hydroxyvitamin $D_3$ measured in serum by a laboratory assay, unless a reference is made to a particular 25-hydroxyvitamin D form, e.g., 25-hydroxyvitamin $D_3$.

As used herein, the term "1,25-dihydroxyvitamin D" refers to one or more of 1,25-dihydroxyvitamin $D_2$, 1,25-dihydroxyvitamin $D_3$, 1,25-dihydroxyvitamin $D_4$, 1,25-dihydroxyvitamin $D_5$, 1,25-dihydroxyvitamin $D_7$, analogs of the foregoing, and combinations thereof. For example, 1,25-dihydroxyvitamin D can include 1,25-dihydroxyvitamin $D_2$, 1,25-dihydroxyvitamin $D_3$, or a combination of 1,25-dihydroxyvitamin $D_2$ and 1,25-dihydroxyvitamin $D_3$. Serum 1,25-dihydroxyvitamin D and serum total 1,25-dihydroxyvitamin D will be understood to refer to the total of 1,25-dihydroxyvitamin $D_2$ and 1,25-dihydroxyvitamin $D_3$ measured in serum by a laboratory assay, unless a reference is made to a particular 1,25-dihydroxyvitamin D form.

As used herein, the term "Vitamin D repletion therapy" refers to the administration to a patient of one or more of a Vitamin D prehormone (e.g., cholecalciferol or ergocalciferol) or an analog thereof, or a Vitamin D prohormone (e.g., 25-hydroxyvitamin $D_2$ or 25-hydroxyvitamin $D_3$) or analog thereof. Examples of compounds suitable for use in Vitamin D repletion therapy include ergocalciferol, cholecalciferol, 25-hydroxyvitamin $D_2$, and 25-hydroxyvitamin $D_3$.

As used herein, the term "Vitamin D hormone replacement therapy" refers to the administration to a patient of an effective amount of one or more of active vitamin D hormones, which include active Vitamin D hormone metabolites, and active Vitamin D hormone analogs, including 1α-hydroxylated Vitamin D compounds. Examples of compounds suitable for use in Vitamin D hormone replacement therapy include the Vitamin D hormones 1,25-dihydroxyvitamin $D_2$, 1,25-dihydroxyvitamin $D_3$, 1,25-dihydroxyvitamin $D_4$, and analogs thereof, including doxercalciferol and paricalcitol.

As used herein, "co-administration" refers to the administration of two or more compounds, e.g., more than one compound for Vitamin D repletion therapy, or a compound for Vitamin D repletion therapy and a compound for Vitamin D hormone replacement therapy, to the same patient. For example, co-administration encompasses (a) simultaneous administration of a first and second compound and (b) administration of a first compound, followed by administration of a second compound. For example, the first and second compounds can be administered within 24 hours, 8 hours, 4 hours, 2 hours, or 1 hour of each other. In other embodiments, different time periods of between administration of first and second compounds may be applicable.

As used herein, the terms "controlled release," "modified release," "sustained release," and "extended release" refer to the release of the administered 25-hydroxyvitamin D compound from a composition in a way that deviates from immediate release. For example, an oral extended release formulation makes the 25-hydroxyvitamin D compound available over an extended period of time following ingestion via the extended release formulation design (see USP 24 <1151>). The foregoing terms optionally include delayed release characteristics, wherein the release of 25-hydroxyvitamin D from an oral formulation is delayed until the capsule has passed through the stomach (see USP 24 <1151>).

As used herein, the term "hypercalcemia" refers to a condition in a patient wherein the patient has two consecutive serum calcium measurements in a course of treatment (e.g., within one month or two weeks apart) above about 10.3 mg/dL.

As used herein, the term "hyperphosphatemia" refers to a condition wherein a patient has two consecutive serum phosphorus measurements in a course of treatment (e.g., within one month or two weeks apart) above about 5.5 mg/dL.

As used herein, the term "hypercalciuria" refers to a condition wherein a patient has a ratio of urine calcium to urine creatinine (Ca/Cr) of >0.2.

As used herein, the term "bioequivalent" refers to a formulation having in vivo biological equivalence to a formulation described herein, if the 90% confidence intervals (90% CI) of the ratios of the Cmax and $AUC_{(0-inf)}$ between the bioequivalent formulation and the reference formulation are both in the range of 80% to 125% (0.8-1.25), when tested with equivalent methods (including an equivalent dose and fasted conditions).

It is specifically understood that any numerical value recited herein includes all values from the lower value to the upper value, i.e., all possible combinations of numerical values between the lowest value and the highest value enumerated are to be considered to be expressly stated in this application. For example, if a concentration range or a beneficial effect range is stated as 1% to 50%, it is intended that values such as 2% to 40%, 10% to 30%, or 1% to 3%, etc., are expressly enumerated in this specification. As another example, a stated concentration of about 20% is intended to include values from 19.5% up to 20.5%. These are only examples of what is specifically intended.

In jurisdictions that forbid the patenting of methods that are practiced on the human body, the meaning of "administering" a composition to a human subject shall be restricted to prescribing a controlled substance that a human subject will self-administer by any technique (e.g., orally, inhalation, topical application, injection, insertion, etc.) and to the manufacture of a medicament for use in the methods described herein. The broadest reasonable interpretation that is consistent with laws or regulations defining patentable subject matter is intended. In jurisdictions that do not forbid the patenting of methods that are practiced on the human body, "administering" compositions includes both methods practiced on the human body and also the foregoing activities.

The compositions and methods of the invention are useful for prophylactic or therapeutic treatment of vitamin D-responsive diseases, i.e., diseases where vitamin D, 25-hydroxyvitamin D or active vitamin D (e.g., 1,25-dihydroxyvitamin D) prevents onset or progression of disease, or reduces signs or symptoms of disease. Such vitamin D-responsive diseases include cancer (e.g., breast, lung, skin, melanoma, colon, colorectal, rectal, prostate and bone cancer). 1,25-dihydroxyvitamin D has been observed to induce cell differentiation and/or inhibit cell proliferation in vitro for a number of cells. Vitamin D-responsive diseases also include autoimmune diseases, for example, type I diabetes, multiple sclerosis, rheumatoid arthritis, polymyositis, dermatomyositis, scleroderma, fibrosis, Grave's disease, Hashimoto's disease, acute or chronic transplant rejection, acute or chronic graft versus host disease, inflammatory bowel disease, Crohn's disease, systemic lupus erythematosis, Sjogren's Syndrome, eczema and psoriasis, dermatitis, including atopic dermatitis, contact dermatitis, allergic dermatitis and/or chronic dermatitis. Vitamin D-responsive diseases also include other inflammatory diseases, for example, asthma, chronic obstructive pulmonary disease, polycystic kidney disease, polycystic ovary syndrome, pancreatitis, nephritis, hepatitis, and/or infection. Vitamin D-responsive diseases have also been reported to include hypertension and cardiovascular diseases. Thus, the invention contemplates prophylactic or therapeutic treatment of subjects at risk of or suffering from cardiovascular diseases, for example, subjects with atherosclerosis, arteriosclerosis, coronary artery disease, cerebrovascular disease, peripheral vascular disease, myocardial infarction, myocardial ischemia, cerebral ischemia, stroke, congestive heart failure, cardiomyopathy, obesity or other weight disorders, lipid disorders (e.g. hyperlipidemia, dyslipidemia including associated diabetic dyslipidemia and mixed dyslipidemia hypoalphalipoproteinemia, hypertriglyceridemia, hypercholesterolemia, and low HDL (high density lipoprotein)), metabolic disorders (e.g. Metabolic Syndrome, Type II diabetes mellitus, Type I diabetes mellitus, hyperinsulinemia, impaired glucose tolerance, insulin resistance, diabetic complication including neuropathy, nephropathy, retinopathy, diabetic foot ulcer and cataracts), and/or thrombosis.

Diseases which can benefit from a modulation in the levels of vitamin D compounds, include, but are not limited to: (i) in the parathyroid—hypoparathyroidism, Pseudo-hypo-parathyroidism, secondary hyperparathyroidism; (ii) in the pancreas—diabetes; (iii) in the thyroid—medullary carcinoma; (iv) in the skin—psoriasis; wound healing; (v) in the lung—sarcoidosis and tuberculosis; (vi) in the kidney—chronic kidney disease, hypophosphatemic VDRR, vitamin D dependent rickets; (vii) in the bone—anticonvulsant treatment, fibrogenisis imperfecta ossium, osteitis fibrosa cystica, osteomalacia, osteoporosis, osteopenia, osteosclerosis, renal osteodytrophy, rickets; (viii) in the intestine—glucocorticoid antagonism, idopathic hypercalcemia, malabsorption syndrome, steatorrhea, tropical sprue; and (ix) autoimmune disorders.

In embodiments of the invention, the disease that benefits from a modulation in the levels of vitamin D compounds are selected from cancer, dermatological disorders (for example psoriasis), parathyroid disorders (for example hyperparathyroidism and secondary hyperparathyroidism), bone disorders (for example osteoporosis) and autoimmune disorders.

In one type of embodiment, the patient has osteoporosis. The patient can suffer from postmenopausal osteoporosis. The patient can suffer from senile ostoporosis.

In one type of embodiment, the patient is one who has previously been treated with a bisphosphonate. For example, the bisphosphonate can be etidronate, pamidronate, alendronate, risedronate, zolendronate, or ibandronate. The bisphosphonate can be one having a long half-life in bone, e.g. at least 3 years, or at least 5 years.

In one aspect, the disclosure provides a method of treating a vitamin-D responsive disease by raising the patient's serum 25-hydroxyvitamin D level as described herein, and concomitantly raising the patient's serum 1,25-dihydroxyvitamin D level to a high level described herein, without causing hypercalcemia. For example, the patient's serum 25-hydroxyvitamin D level can be raised using an extended release, oral dosage form containing 25-hydroxyvitamin $D_3$, 25-hydroxyvitamin $D_2$, or a combination of 25-hydroxyvitamin $D_3$ and 25-hydroxyvitamin $D_2$.

Repeat doses of 25-hydroxyvitamin D can be given, for example, daily, every other day, two or three times per week, weekly, every other week, or monthly. Optionally, the repeat doses of 25-hydroxyvitamin D are administered for an extended period, for example, at least one week, at least two weeks, at least three weeks, one month, at least two months, at least three months, at least four months, at least five months, at least six months, at least seven months, at least eight months, at least nine months, at least ten months, at least eleven months, at least one year, or longer. It is contemplated that an escalating dosing schedule can be implemented wherein repeat doses are administered on a first schedule for a first period of time, and then at a higher dose on the same schedule for a second period of time. For example, the dose can be an initial dose daily for one month, then an increased dose daily for a second month, then a further increased dose daily for the third month. In another embodiment the dose can be an initial dose 3 times per week for one month, then an increased dose 3 times week for a second month, and then a further increased dose 3 times per week for a third month.

In one type of embodiment, the 25-hydroxyvitamin D (e.g. calcifediol) can be administered in the fasted state. In one type of embodiment, the 25-hydroxyvitamin D (e.g. calcifediol) is administered at bedtime.

In one aspect the 25-hydroxyvitamin D can be administered while controlling the patient's total dietary calcium intake (from both food sources and supplements combined) to 1000 mg/day, or less than 1000 mg/day, or less than 900 mg/day, or less than 800 mg/day, or less than 700 mg/day, or less than 600 mg/day, or less than 500 mg/day, for example in a range of 400-1000 mg/day, or 400-900 mg/day, or 400-800 mg/day, or 400-700 mg/day, or 400-600 mg/day, or 500-700 mg/day.

The methods of the disclosure are effective to raise the patient's serum 25-hydroxyvitamin D to levels previously considered unsafe, but without causing one or more side effects associated with Vitamin D toxicity. Recent data suggest a treatment target for serum 25-hydroxyvitamin D in CKD patients of 40 to 50 ng/mL to lower PTH levels (Ennis et al., *J Nephrol* 29(1):63-70, 2015). While a serum 25-hydroxyvitamin D level of 100 ng/mL has been considered an acceptable upper limit of normal, the methods of the disclosure can be used to raise serum 25-hydroxyvitamin D to significantly higher levels, without causing, for example, one or more of hypercalcemia, hyperphosphatemia, hypercalciuria, and adynamic bone disease. In one aspect, the method is effective to raise the patient's serum 25-hydroxyvitamin D level to greater than about 100 ng/mL, for example, greater than about 110 ng/mL, greater than about 120 ng/mL, greater than about 130 ng/mL, greater than about 140 ng/mL, greater than about 150 ng/mL, greater than about 160 ng/mL, greater than about 170 ng/mL, greater than about 180 ng/mL, greater than about 190 ng/mL, greater than about 200 ng/mL, greater than about 210 ng/mL, greater than about 220 ng/mL, greater than about 230 ng/mL, greater than about 240 ng/mL, greater than about 250 ng/mL, greater than about 300 ng/mL, or greater than about 350 ng/mL. In another aspect, the method is effective to raise the patient's serum 25-hydroxyvitamin D level to up to 500 ng/mL, up to 450 ng/mL, up to 400 ng/mL, up to 350 ng/mL, up to 300 ng/mL, up to 250 ng/mL, or up to 240 ng/mL, or up to 230 ng/mL, or up to 220 ng/mL, or up to 210 ng/mL, or up to 200 ng/mL, or up to 190 ng/mL, or up to 180 ng/mL, for example. Optionally, the patient's serum 25-hydroxyvitamin D level is raised to a value in a range of about 90 ng/mL to about 120 ng/mL, or in a range of about 100 ng/mL to about 150 ng/mL, or in a range of about 120 ng/mL to about 160 ng/mL, or in a range of about 140 ng/mL to about 180 ng/mL, or in a range of about 150 ng/mL to about 200 ng/mL, or in a range of about 180 ng/mL to about 200 ng/mL, or in a range of about 190 ng/mL to about 220 ng/mL, or in a range of about 150 ng/mL to about 350 ng/mL or in a range of about 200 ng/mL to about 300 ng/mL, or in a range of about 250 ng/mL to about 300 ng/mL, or in a range of about 150 ng/mL to about 300 ng/mL.

The Vitamin D prohormones 25-hydroxyvitamin $D_3$ and 25-hydroxyvitamin $D_2$ are metabolized primarily in the kidneys by the 1α-hydroxylase enzyme CYP27B1 into the potent, active hormones (25-hydroxyvitamin $D_2$ is metabolized into 1α,25-dihydroxyvitamin $D_2$ and 25-hydroxyvitamin $D_3$ is metabolized into 1α,25-dihydroxyvitamin $D_3$). It was observed that with repeat dosing of extended release oral 25-hydroxyvitamin $D_3$ in stage 3 and 4 CKD patients, a dose of 30 mcg/day raised serum 1,25-dihydroxyvitamin D, but a dose of 60 mcg/day provided levels of serum 1,25-dihydroxyvitamin D approximately equal to the 30 mcg/day dose; yet, a dose of 90 mcg/day did further raise serum 1,25-dihydroxyvitamin D. It is believed that at a lower dose, 1,25-dihydroxyvitamin D resulted primarily from renal 1-hydroxylase, but that as serum 1,25-dihydroxyvitamin D levels rose, renal 1-hydroxylase was suppressed. With increased dosing of the extended release oral 25-hydroxyvitamin $D_3$ (e.g. 90 mcg/day) it is believed that extrarenal production of 1,25-dihydroxyvitamin D was contributing to serum 1,25-dihydroxyvitamin D levels to a more significant extent.

It has also been observed that with increasing, repeat doses of extended release oral 25-hydroxyvitamin $D_3$, serum 1,25-dihydroxyvitamin D levels can be raised to very high levels, without inducing hypercalcemia. It is believed that the gradual rise in serum 25-hydroxyvitamin D, and the gradual rise in serum 1,25-dihydroxyvitamin D, allow for a physiological adaptation under which intestinal calcium absorption is not induced or is induced to a significantly lesser extent, compared to methods which raise serum 25-hydroxyvitamin D and/serum 1,25-dihydroxyvitamin D more rapidly.

In another aspect, the disclosure provides a method of treating secondary hyperparathyroidism in a patient having CKD, comprising administering to the patient repeat doses of 25-hydroxyvitamin D effective to raise the patient's serum 25-hydroxyvitamin D level to greater than 90 ng/ml. In another aspect, the disclosure provides a method of treating secondary hyperparathyroidism in a patient having CKD, comprising administering to the patient repeat doses of 25-hydroxyvitamin D effective to raise the patient's serum 25-hydroxyvitamin D level to greater than 90 ng/ml and to control the patient's serum ratio of 25-hydroxyvitamin D to 24,25-dihydroxyvitamin D to less than 20, or less than 15.

Figure 3A:
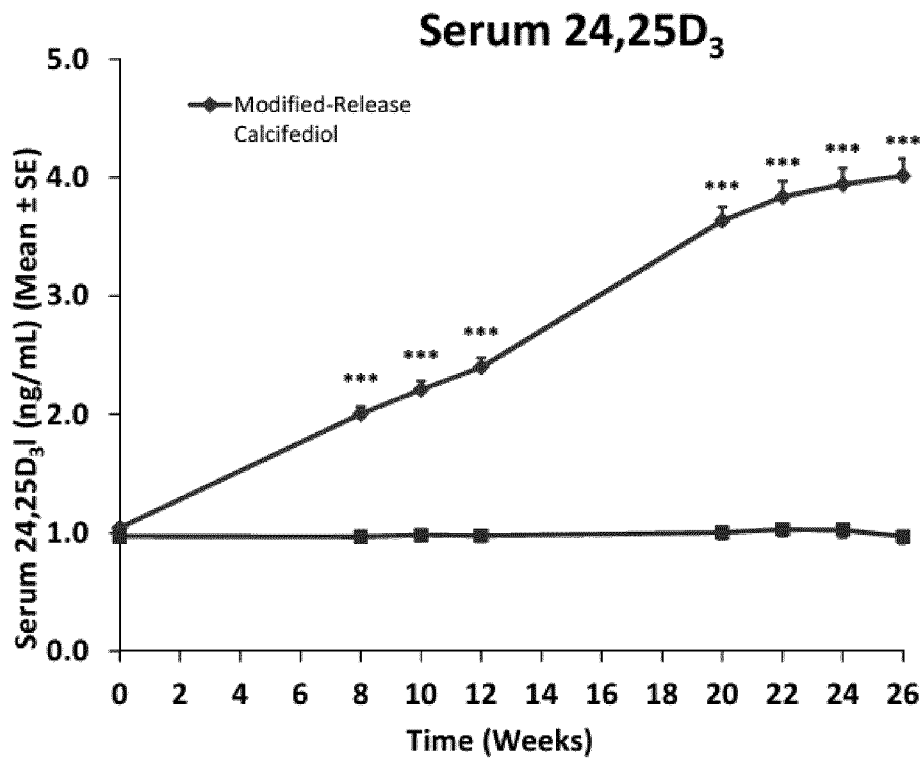
FIG. 3A shows mean (±SE) serum 24,25-dihydroxyvitamin $D_3$ (ng/mL) in subjects administered a placebo (squares) or an extended release formulation of 25-hydroxyvitamin $D_3$ (diamonds) for 26 weeks. Triple asterisks (***) denote a significant difference from placebo, $p<0.0001$.
Figure 3B:
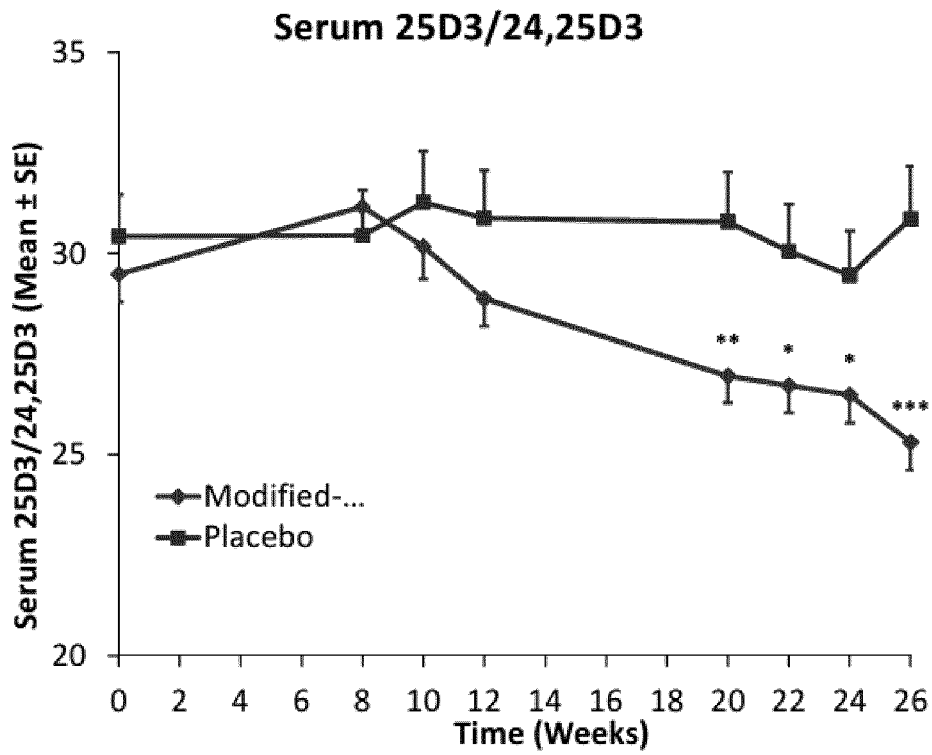
FIG. 3B shows the ratio of serum calcifediol (25-hydroxvitamin $D_3$) to serum 24,25-dihydroxyvitamin $D_3$ in subjects administered a placebo (squares) or an extended release formulation of 25-hydroxyvitamin $D_3$ (diamonds) for 26 weeks. Asterisks denote a significant difference from placebo (*=$p<0.05$, =$p<0.001$,*=$p<0.0001$).
Figure 3C:
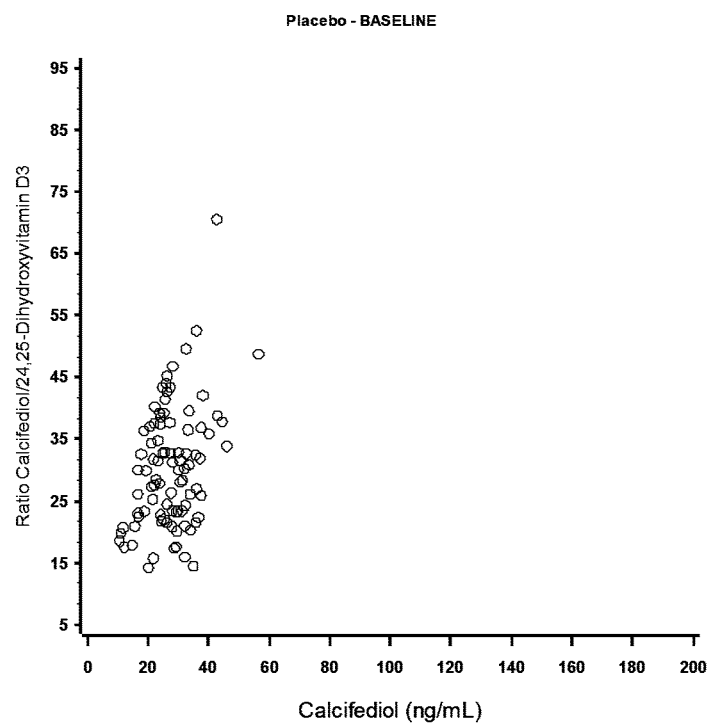
FIG. 3C and FIG. 3D show the ratio of calcifediol to 24,25-dihydroxyvitamin $D_3$ compared to serum calcifediol at baseline (FIG. 3C) and at the end of the efficacy assessment period (EAP) (FIG. 3D) for CKD Stage 3 and Stage 4 patients administered a placebo for 26 weeks.
Figure 3D:
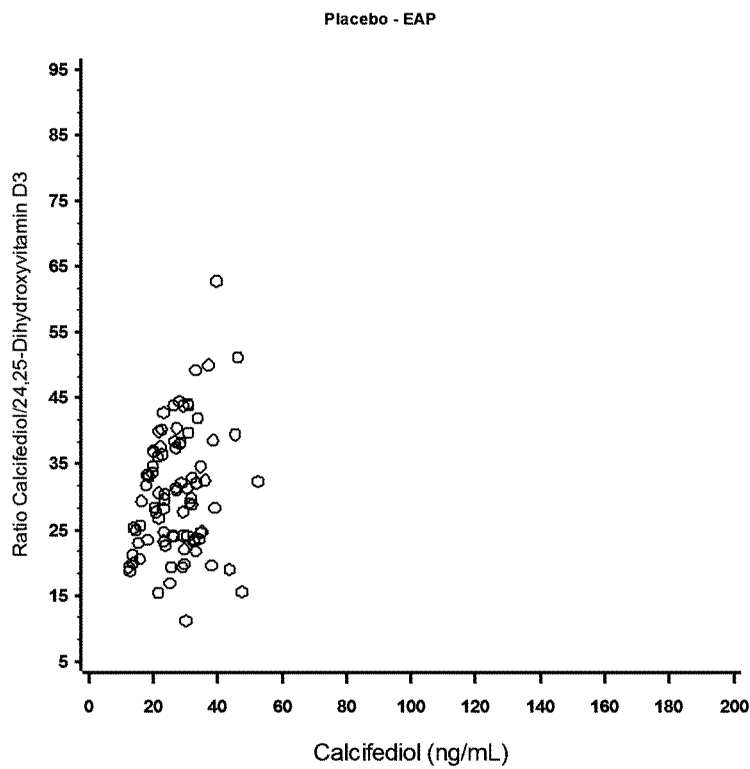
Figure 3E:
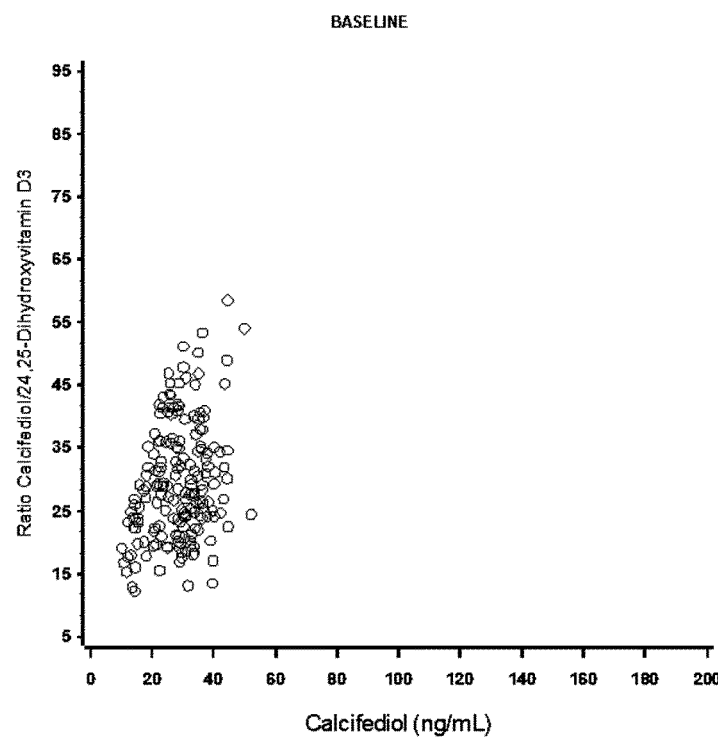
FIG. 3E and FIG. 3F show the ratio of calcifediol to 24,25-dihydroxyvitamin $D_3$ compared to serum calcifediol at baseline (FIG. 3E) and at the end of the efficacy assessment period (EAP) (FIG. 3F) for CKD Stage 3 and Stage 4 patients administered an extended release formulation of 25-hydroxyvitamin $D_3$ for 26 weeks.
Figure 3F:
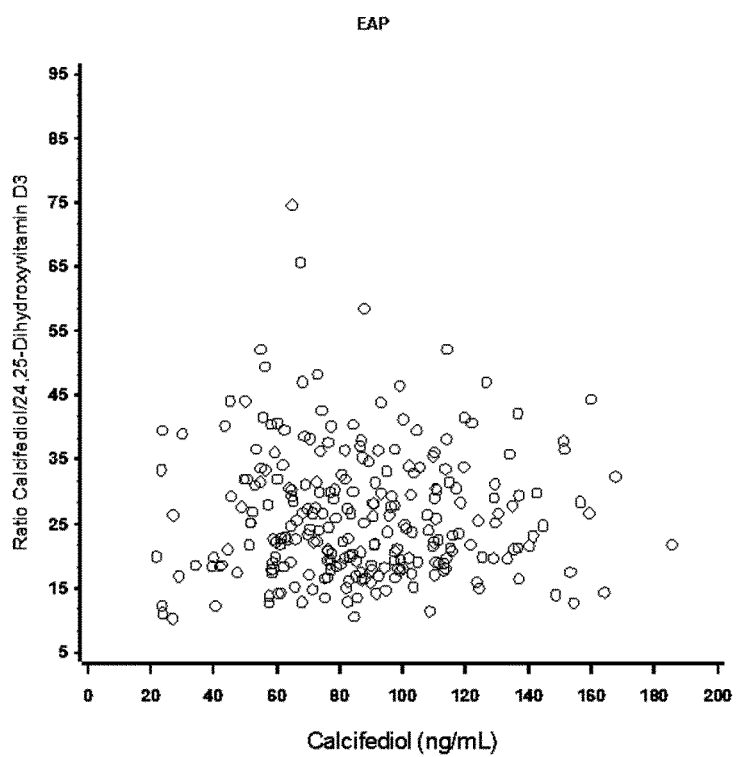
Figure 4A:
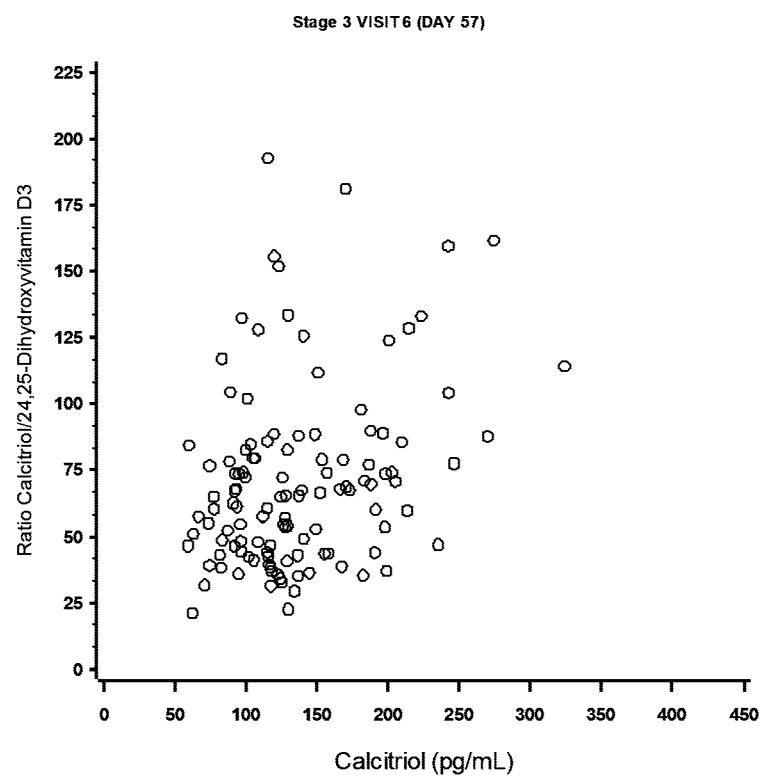
FIG. 4A to FIG. 4C show the ratio of calcifediol to 24,25-dihydroxyvitamin $D_3$ compared to serum calcifediol at Visit 6/Day 57 (FIG. 4A), Visit 10/Day 141 (FIG. 4B) and Visit 13/Day 183 (FIG. 4C) for CKD Stage 3 patients administered an extended release formulation of 25-hydroxyvitamin $D_3$ for 26 weeks.
Figure 4B:
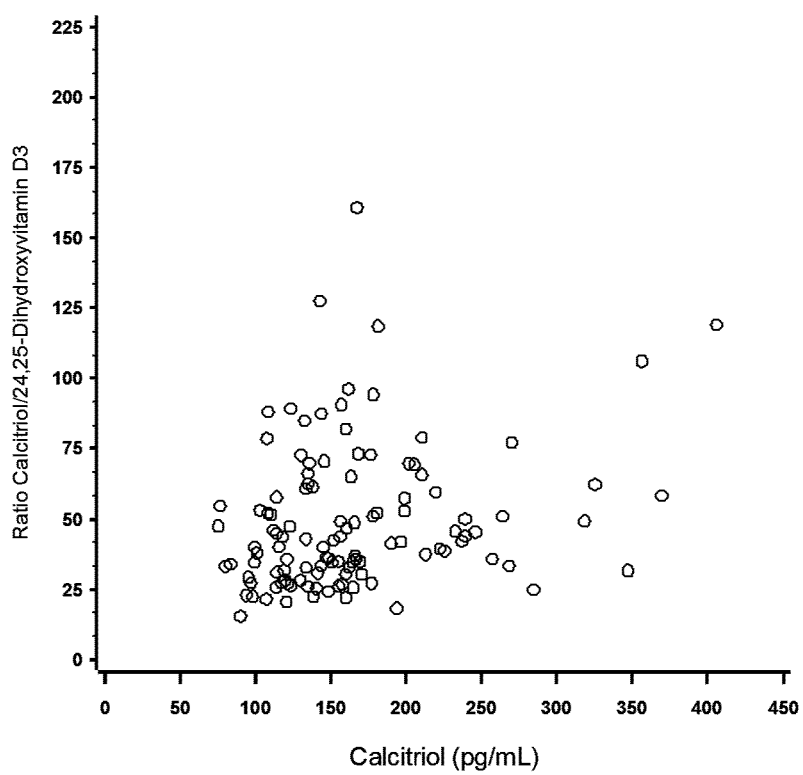
Figure 4C:
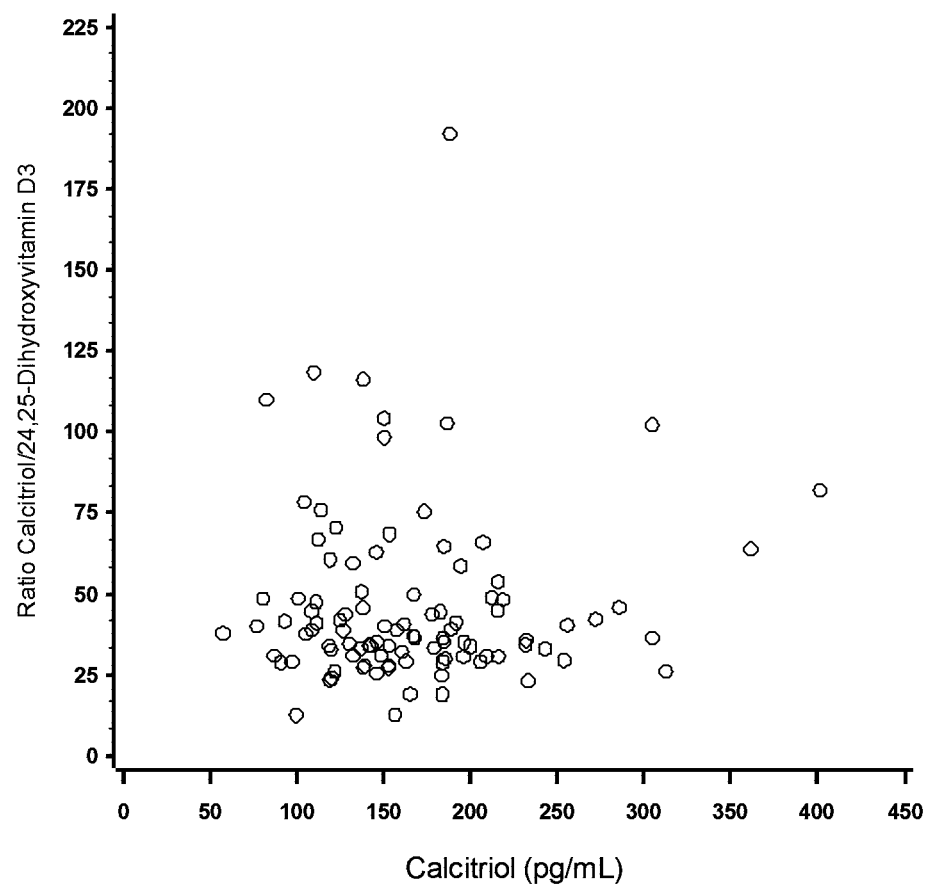
Figure 5A:
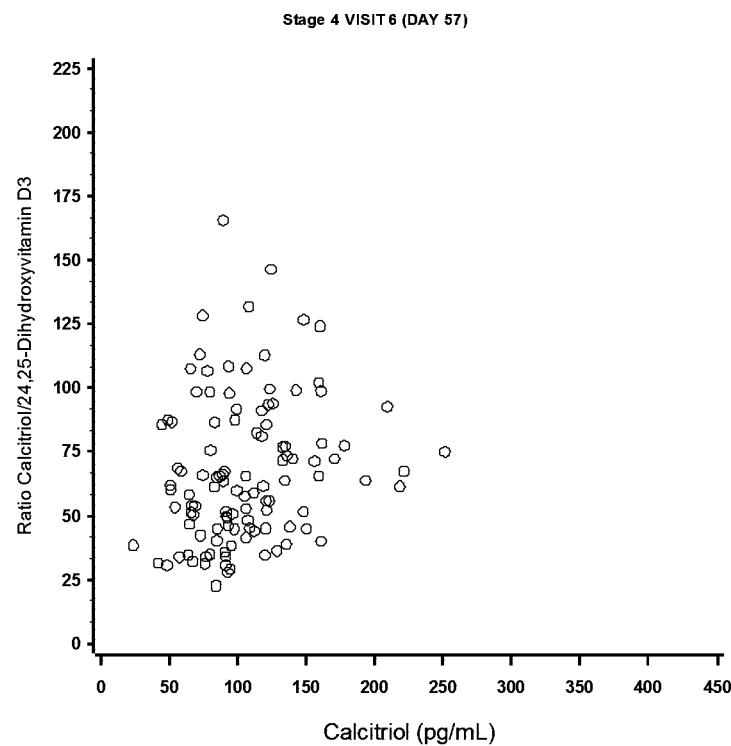
FIG. 5A to FIG. 5C show the ratio of calcifediol to 24,25-dihydroxyvitamin $D_3$ compared to serum calcifediol at Visit 6/Day 57 (FIG. 5A), Visit 10/Day 141 (FIG. 5B) and Visit 13/Day 183 (FIG. 5C) for CKD Stage 4 patients administered an extended release formulation of 25-hydroxyvitamin $D_3$ for 26 weeks.
Figure 5B:
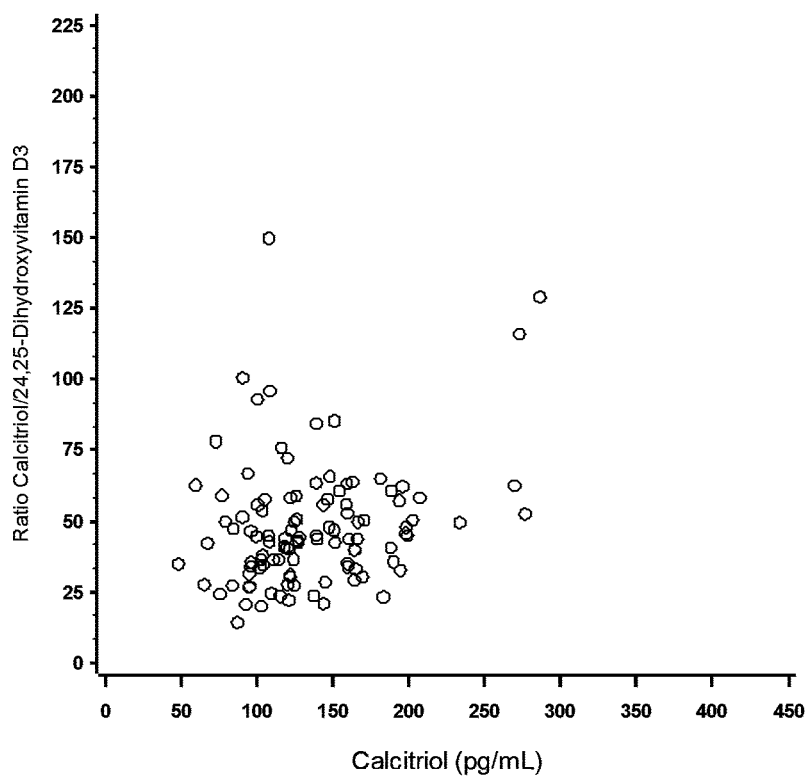
Figure 5C:
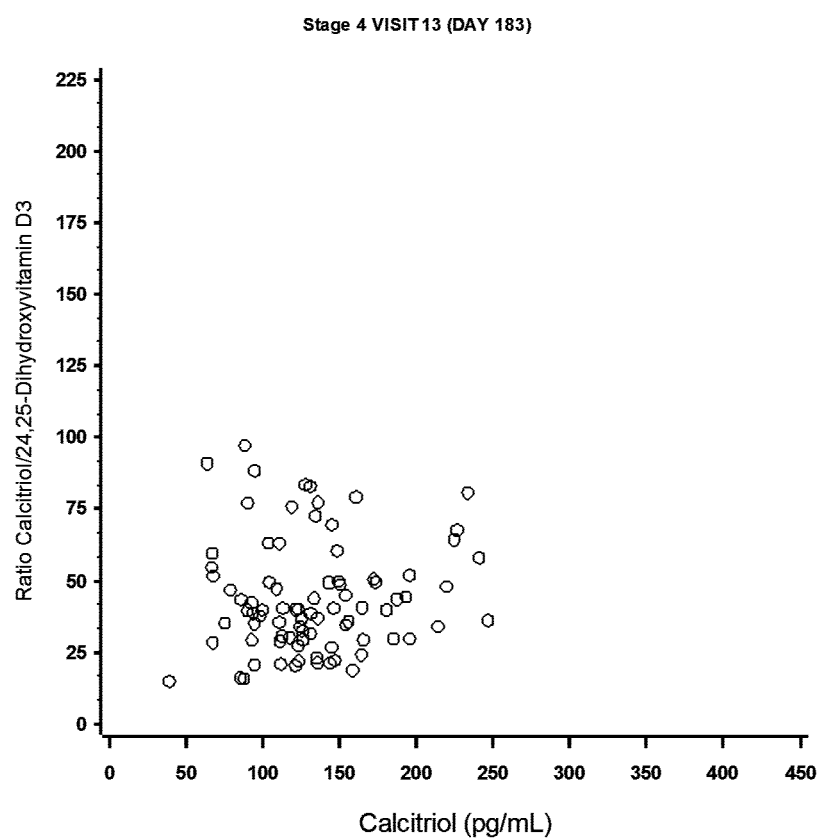

In another aspect, a method of the disclosure comprises administering repeat doses of a compound for Vitamin D repletion therapy, for example, 25-hydroxyvitamin D and/or ergocalciferol or cholecalciferol, in an amount effective to control the patient's serum ratio of 25-hydroxyvitamin D to 24,25-dihydroxyvitamin D to less than 20, or less than 18, or less than 16, or less than 15, or less than 14, or less than 12, or less than 10. For example, in one aspect, the disclosure provides a method of treating vitamin D insufficiency in a patient having CKD, comprising administering to the patient repeat doses of 25-hydroxyvitamin D effective to control the patient's serum ratio of 25-hydroxyvitamin D to 24,25-dihydroxyvitamin D to less than 20. In another aspect, the disclosure provides a method of treating vitamin D insufficiency in a patient having CKD, comprising administering to the patient repeat doses of a compound for Vitamin D repletion therapy, for example, 25-hydroxyvitamin D and/or ergocalciferol or cholecalciferol, in an amount effective to increase the patient's serum 25-hydroxyvitamin D level to greater than about 100 ng/mL and to control the patient's serum ratio of 25-hydroxyvitamin D to 24,25-dihydroxyvitamin D to less than 20. In normal subjects, a plot of the serum ratio of 25-hydroxyvitamin D to 24,25-dihydroxyvitamin D (25(OH)D3:24,25(OH)2D3) versus serum 25-hydroxyvitamin D (25(OH)D3) reached a plateau when 25(OH)D3:24,25(OH)2D3 was less than 20, indicating Vitamin D sufficiency (Kaufmann et al., supra). In CKD patients, a ratio of 25(OH)D3:24,25(OH)2D3 of less than 25 was not achieved even as serum 25-hydroxyvitamin D values approached and exceeded 100 ng/mL (FIG. 3F), indicating that the ratio of 25(OH)D3:24,25(OH)2D3 corresponding to Vitamin D sufficiency in CKD patients would be achieved at a much higher concentration of serum 25-hydroxyvitamin D for defining Vitamin D sufficiency in CKD patients could be significantly less than 20. Optionally, the patient's serum ratio of 25-hydroxyvitamin D to 24,25-dihydroxyvitamin D is lowered to or maintained at a ratio of less than 20, less than 15, or less than 10, for example, the ratio of 25-hydroxyvitamin D to 24,25-dihydroxyvitamin D is about 25, about 24, about 23, about 22, about 21, about 20, about 19, about 18, about 17, about 16, about 15, about 14, about 13, about 12, about 11, about 10, about 9, about 8, about 7, about 6, or about 5. Quantification of 25-hydroxyvitamin D and 24,25-dihydroxyvitamin D can be performed using a suitable assay. Suitable assays are known in the art, for example, radioimmunoassay, mass spectrometry, HPLC, and LC-MS/MS, e.g., as described in Kaufmann et al., supra, Wagner et al., supra, and Berg et al., supra.

Administration of a compound for Vitamin D hormone replacement therapy alone can reduce serum 25-hydroxyvitamin D while increasing catabolism by CYP24A, thereby increasing serum 24,25-dihydroxyvitamin D and resulting in a decrease in the serum ratio of 25-hydroxyvitamin D to 24,25-dihydroxyvitamin D, but without achieving Vitamin D sufficiency. It may be possible that administration of a compound for Vitamin D hormone replacement therapy alone could result in the serum ratio of 25-hydroxyvitamin D to 24,25-dihydroxyvitamin D to 20 or less. Accordingly, it is contemplated that in one category of embodiments of the methods described herein, patients will and will be treated to control the patient's ratio of 25-hydroxyvitamin D to 24,25-dihydroxyvitamin D to less than 20 and simultaneously will have a serum level of 25-hydroxyvitamin D of at least 30 ng/ml. In another category of embodiments of the methods described herein, patients will be treated to control the patient's ratio of 25-hydroxyvitamin D to 24,25-dihydroxyvitamin D to less than 20 and will receive vitamin D repletion therapy. Optionally, the patients can be treated in the absence of administration of a compound for Vitamin D hormone replacement therapy. In one type of embodiment, a method of treating secondary hyperparathyroidism and Vitamin D insufficiency in a patient having Chronic Kidney Disease comprises administering to the patient repeat doses of a compound for Vitamin D repletion therapy effective to raise the patient's serum 25-hydroxyvitamin D level to greater than 90 ng/ml and to control the patient's serum ratio of 25-hydroxyvitamin D to 24,25-dihydroxyvitamin D to less than 20, wherein the patient is not receiving Vitamin D hormone replacement therapy. In another type of embodiment, a method of treating secondary hyperparathyroidism and Vitamin D insufficiency in a patient having Chronic Kidney Disease comprises co-administering to the patient repeat doses of a compound for Vitamin D repletion therapy and a compound for Vitamin D hormone replacement therapy effective to raise the patient's serum 25-hydroxyvitamin D level to greater than 30 ng/ml and to control the patient's serum ratio of 25-hydroxyvitamin D to 24,25-dihydroxyvitamin D to less than 20.

In another aspect, the disclosure provides a method of treating vitamin D insufficiency in a patient having CKD, comprising administering to the patient repeat doses of 25-hydroxyvitamin D effective to increase the patient's serum 1,25-dihydroxyvitamin D level to greater than about 40 pg/mL, optionally to also control the patient's serum ratio of 25-hydroxyvitamin D to 24,25-dihydroxyvitamin D to less than 20. Optionally, the patient's serum 1,25-dihydroxyvitamin D level is increased to greater than 40 pg/mL, greater than 45 pg/mL, greater than 50 pg/mL, greater than 55 pg/mL, greater than 60 pg/mL, greater than 65 pg/mL, greater than 70 pg/mL, greater than 75 pg/mL, greater than 80 pg/mL, greater than 90 pg/mL, greater than 100 pg/mL, greater than 110 pg/mL, greater than 120 pg/mL, greater than 130 pg/mL, greater than 140 pg/mL, greater than 150 pg/mL, greater than 160 pg/mL, greater than 170 pg/mL, greater than 180 pg/mL, greater than 190 pg/mL, greater than 200 pg/mL, greater than 210 pg/mL, greater than 220 pg/mL, greater than 230 pg/mL, greater than 240 pg/mL, greater than 250 pg/mL, greater than 260 pg/mL, greater than 270 pg/mL, greater than 280 pg/mL, greater than 290 pg/mL, or greater than 300 pg/mL. Optionally, the patient's serum 1,25-dihydroxyvitamin D level is increased to a value within a range of 150 pg/mL to 350 pg/mL, or 150 pg/mL to 300 pg/mL, or 200 pg/mL to 300 pg/mL, for example. Optionally, the patient's serum 1,25-dihydroxyvitamin D level is increased from baseline by at least 25 pg/mL, at least 50 pg/mL, at least 75 pg/mL, at least 100 pg/mL, at least 125 pg/mL, at least 150 pg/mL, at least 175 pg/mL, or at least 200 pg/mL.

In any of the methods of the disclosure, repeat doses of 25-hydroxyvitamin D are optionally administered to the subject in an amount effective to have one or more effects including to (a) lower PTH, (b) increase serum 25-hydroxyvitamin D, (c) increase serum 1,25-dihydroxyvitamin D, or (d) control the ratio of 25-hydroxyvitamin D to 24,25-dihydroxyvitamin D as described herein. The dosing can also be performed to avoid one or more negative effects, including (a) without increasing serum calcium, (b) without increasing serum phosphorus, (c) without increasing a marker of bone turnover, (d) without inducing hypercalcemia, or (e) without inducing hyperphosphatemia. In one aspect, repeat doses of 25-hydroxyvitamin D are optionally administered to the subject in an amount effective to lower the patient's blood PTH level (e.g., plasma intact PTH) by at least about 15%, for example, at least about 15%, at least about 20%, at least about 25%, at least about 30%, at least about 35%, at least about 40%, at least about 45%, or at least about 50%, compared to its pre-treatment level. In another aspect, repeat doses of 25-hydroxyvitamin D are optionally administered to a patient population in an amount effective to lower the mean plasma intact PTH level of the patient population by at least about 15%, for example, at least about 15%, at least about 20%, at least about 25%, at least about 30%, at least about 35%, at least about 40%, at least about 45%, or at least about 50%, compared to its pre-treatment level.

In one aspect, repeat doses of 25-hydroxyvitamin D are administered in an amount effective to maintain serum calcium in a range of about 9.0 mg/dL to about 10.0 mg/dL, for example in a range of about 9.0 mg/dL to about 9.5 mg/dL, in a range of about 9.2 mg/dL to about 9.6 mg/dL, or in a range of about 9.3 mg/dL to about 9.8 mg/dL. In another aspect, repeat doses of 25-hydroxyvitamin D are administered in an amount effective to increase serum calcium in an amount in the range of 0 to about 0.3 mg/dL. In one aspect, repeat doses of 25-hydroxyvitamin D are administered in an amount effective to maintain serum phosphorous in a range of about 3.5 mg/dL to about 4.5 mg/dL, for example in a range of about 3.5 mg/dL to about 4.0 mg/dL, in a range of about 3.6 mg/dL to about 4.2 mg/dL, or in a range of about 3.7 mg/dL to about 4.1 mg/dL. In another aspect, repeat doses of 25-hydroxyvitamin D are administered in an amount effective to increase serum phosphorous in an amount in the range of 0 to about 0.3 mg/dL. In one aspect, repeat doses of 25-hydroxyvitamin D are administered in an amount effective to maintain or decrease a marker of bone turnover selected from urine Ca/Cr, urine TRP, serum BSAP, serum CTX-1, serum P1NP, and combinations thereof.

In any of the methods of the disclosure, 25-hydroxyvitamin D is optionally administered in a modified release composition, for example, an extended-release oral dosage form comprising 25-hydroxyvitamin $D_3$. In one type of embodiment, modified release compositions intended for oral administration in accordance with the present invention are designed to contain a concentration of 25-hydroxyvitamin D (e.g. 25-hydroxyvitamin $D_3$, or a combination of 25-hydroxyvitamin $D_2$ and 25-hydroxyvitamin $D_3$) of 1 to 1000 mcg per unit dose, or 1 to 500 mcg per unit dose or 1 to 100 mcg per dose, or 1 to 50 mcg per dose, or 10 to 40 mcg per dose, for example 30 mcg per dose, 60 mcg per dose, 90 mcg per dose, 150 mcg per dose, 300 mcg per dose, 450 mcg per dose, 600 mcg per dose, 750 mcg per dose, or 900 mcg per dose, and are prepared in such a manner as to effect controlled or substantially constant release of the 25-hydroxyvitamin D into the gastrointestinal tract of a subject over an extended period of time. In one embodiment, the 25-hydroxyvitamin D is 25-hydroxyvitamin $D_3$. In another embodiment, the 25-hydroxyvitamin D is a combination of 25-hydroxyvitamin $D_3$ and 25-hydroxy vitamin $D_2$ and are useful in supporting both the Vitamin $D_3$ and Vitamin $D_2$ endocrine systems. Currently available oral Vitamin D supplements and the previously marketed oral formulation of 25-hydroxyvitamin $D_3$ have supported just one or the other system. In one type of embodiment, the release can be in the ileum or later, for example in the colon. In another type embodiment, the composition can result in a substantially increased absorption of 25-hydroxyvitamin D via transport on DBP and decreased absorption via transport in chylomicrons. Examples of modified release compositions of 25-hydroxyvitamin D are described in U.S. Pat. Nos. 8,207,149; 8,361,488; 8,426,391; 8,778,373; and 8,906,410; and U.S. patent application Ser. No. 14/213,285, incorporated herein by reference.

In one type of embodiment, the 25-hydroxyvitamin D is administered orally. For example, the 25-hydroxyvitamin D can be administered in an oral modified release formulation. In the alternative, the 25-hydroxyvitamin D can be administered in an oral immediate release formulation in multiple daily doses in order to produce a pharmacokinetic profile of serum 25-hydroxyvitamin D that is similar to that achieved by an oral modified or sustained release formulation.

The preparation of a modified release form of 25-hydroxyvitamin D suitable for oral administration can be carried out according to many different techniques. For example, one or more 25-hydroxyvitamin D compounds can be dispersed within a matrix, i.e., a mixture of rate controlling constituents and excipients in carefully selected ratios within the matrix, and optionally encased with a coating material. In another alternative, various coating techniques can be utilized to control the rate and/or the site of the release of the 25-hydroxyvitamin D from the pharmaceutical formulation. For example, the dissolution of the coating may be triggered by the pH of the surrounding media, and the resulting gradual dissolution of the coating over time exposes the matrix to the fluid of the local environment. In one type of embodiment, after the coating becomes permeable, 25-hydroxyvitamin D diffuses from the outer surface of the matrix. When this surface becomes exhausted or depleted of 25-hydroxyvitamin D, the underlying stores begin to be depleted by diffusion through the disintegrating matrix to the external solution. In another type of embodiment, release of 25-hydroxyvitamin D is by gradual disintegration or erosion of the matrix, e.g., via solubility of one or more components of the matrix and/or by lack of physical integrity.

In one aspect, a formulation in accordance with the disclosure provides one or more 25-hydroxyvitamin D compounds within a matrix that releasably binds the ingredients for extended release, e.g., when exposed to the contents of the ileum and/or colon.

Optionally, the 25-hydroxyvitamin D-containing dosage form or matrix can be suitably covered with a coating that is resistant to disintegration in gastric juices. The coated modified release formulation of 25-hydroxyvitamin D is then administered orally to subjects, e.g., animals or human patients. As the formulation travels through the proximal portion of the small intestine, the enteric coating becomes progressively more permeable but, in a suitable embodiment, it provides a persisting structural framework around the 25-hydroxyvitamin D-containing matrix. The 25-hydroxyvitamin D-containing matrix becomes significantly exposed to intestinal fluids in the ileum through the permeable overcoating, and the 25-hydroxyvitamin D is then gradually released by simple diffusion and/or slow disintegration of the matrix.

Once released into the lumen of the ileum, the 25-hydroxyvitamin D is absorbed into the lymphatic system or into the portal bloodstream, where it is bound to and transported by the DBP. In a delayed release embodiment, the 25-hydroxyvitamin D is primarily absorbed at a point beyond the duodenum and jejunum. These proximal portions of the small intestine can respond to high intralumenal levels of 25-hydroxyvitamin D and in the process, can catabolize significant quantities of the 25-hydroxyvitamin D. By substantially delaying 25-hydroxyvitamin D release until the ileum and/or colon, the pharmaceutical composition described herein can virtually eliminate these potential first-pass effects in the proximal intestine and reduces unwanted catabolism. Significant catabolism of administered 25-hydroxyvitamin D prior to absorption into the bloodstream significantly lowers its bioavailability. Elimination of first-pass effects reduces the risk of Vitamin D toxicity. Substantially delayed release of 25-hydroxyvitamin D (i.e., beyond the duodenum and jejunum) markedly decreases the amount of 25-hydroxyvitamin D that is incorporated and absorbed from the small intestine via chylomicrons (since chylomicron formation and absorption occurs primarily in the jejunum) and correspondingly increases the amount of 25-hydroxyvitamin D that is absorbed directly through the intestinal wall and onto DBP circulating in lymph or portal blood.

In one embodiment of the invention, a controlled release oral formulation of 25-hydroxyvitamin D is prepared generally according to the following procedure. A sufficient quantity of 25-hydroxyvitamin D is completely dissolved in a minimal volume of USP-grade absolute ethanol (or other suitable solvent) and mixed with appropriate amounts and types of pharmaceutical-grade excipients to form a matrix which is solid or semi-solid at both room temperature and at the normal temperature of the human body. The matrix is completely or almost entirely resistant to digestion in the stomach and upper small intestine, and it gradually disintegrates in the lower small intestine and/or colon.

In a suitable formulation, the matrix binds the 25-hydroxyvitamin D compound(s) and permits a slow, relatively steady, e.g. substantially constant, release of 25-hydroxyvitamin D over a period of four to eight hours or more, by simple diffusion and/or gradual disintegration, into the contents of the lumen of the lower small intestine and/or colon. The formulation optionally further has an enteric coating that partially dissolves in aqueous solutions having a pH of about 7.0 to 8.0, or simply dissolves slowly enough that significant release of 25-hydroxyvitamin D is delayed until after the formulation passes through the duodenum and jejunum.

The means for providing the controlled release of 25-hydroxyvitamin D may be selected from any suitable controlled release delivery system, including any of the known controlled release delivery systems of an active ingredient, including the wax matrix system, and the EUDRAGIT RS/RL system (Rohm Pharma, GmbH, Weiterstadt, Germany).

The wax matrix system provides a lipophilic matrix. The wax matrix system may utilize, for example, natural or synthetic waxes, digestible or non-digestible waxes, e.g. beeswax, white wax, cachalot wax or similar compositions, or mixtures of waxes. In one type of embodiment the wax is a non-digestible wax. The active ingredient(s) are dispersed in the wax binder which slowly disintegrates in intestinal fluids to gradually release the active ingredient(s). The wax binder that is impregnated with 25-hydroxyvitamin D can be loaded into capsules, e.g. softgel capsules. A softgel capsule may comprise one or more gel-forming agents, e.g., gelatin, starch, carrageenan, and/or other pharmaceutically acceptable polymers. In one embodiment, partially crosslinked soft gelatin capsules are used. As another option, vegetable-based capsules can be used. The wax matrix system disperses the active ingredient(s) in a wax binder which softens at body temperature and slowly disintegrates in intestinal fluids to gradually release the active ingredient(s). The system suitably can include a mixture of waxes, with the optional addition of oils, to achieve a melting point which is higher than body temperature, but lower than the melting temperature of the selected formulations used to create the shell of a soft or hard capsule, or vegetable capsule shell, or other formulation used to create a shell casing or other coating.

In one type of embodiment, the wax matrix comprises a controlled release agent, an emulsifier, and an absorption enhancer. Examples of controlled release agents suitable for use include, but are not limited to, waxes, including synthetic waxes, microcrystalline wax, paraffin wax, carnauba wax, and beeswax; polyethoxylated castor oil derivatives, hydrogenated vegetable oils, glyceryl mono-, di- or tribehenates; long-chain alcohols, such as stearyl alcohol, cetyl alcohol, and polyethylene glycol; and mixtures of any of the foregoing. Non-digestible waxy substances, e.g. hard paraffin wax, are particularly contemplated. The controlled release agent can be present in an amount of at least 5 wt % of the formulation, or greater than about 5 wt % of the formulation. For example, depending on the controlled release agent used, the controlled release agent can comprise at least 5 wt % of the formulation or at least 10 wt % of the formulation, or at least 15 wt % of the formulation, or at least 20 wt % of the formulation, or at least 25 wt % of the formulation, or greater than 5 wt % of the formulation, or greater than 10 wt % of the formulation, or greater than 15 wt % of the formulation, or greater than 20 wt % of the formulation, and or greater than 25 wt % of the formulation. The controlled release agent can be present in an amount 50 wt % or less, 40 wt % or less, 35 wt % or less, or 30 wt % or less. Suitable ranges include 5 wt % to 40 wt %, 10 wt % to 30 wt % and 15 wt % to 25 wt %. Examples include about 15 wt %, about 16 wt %, about 17 wt %, about 18 wt %, about 19 wt %, about 20 wt %, about 21 wt %, about 22 wt %, about 23 wt %, about 24 wt %, and about 25 wt %.

Examples of emulsifiers suitable for use in the formulation include, but are not limited to, lipophilic agents having an HLB of less than 7, such as mixed fatty acid monoglycerides; mixed fatty acid diglycerides; mixtures of fatty acid mono- and diglycerides; lipophilic polyglycerol esters; glycerol esters including glyceryl monooleate, glyceryl dioleate, glyceryl monostearate, glyceryl distearate, glyceryl monopalmitate, and glyceryl dipalmitate; glyceryl-lacto esters of fatty acids; propylene glycol esters including propylene glycol monopalmitate, propylene glycol monostearate, and propylene glycol monooleate; sorbitan esters including sorbitan monostearate, sorbitan sesquioleate; fatty acids and their soaps including stearic acid, palmitic acid, and oleic acid; and mixtures thereof glyceryl monooleate, glyceryl dioleate, glyceryl monostearate, glyceryl distearate, glyceryl monopalmitate, and glyceryl dipalmitate; glyceryl-lacto esters of fatty acids; propylene glycol esters including propylene glycol monopalmitate, propylene glycol monostearate, and propylene glycol monooleate; sorbitan esters including sorbitan monostearate, sorbitan sesquioleate; fatty acids and their soaps including stearic acid, palmitic acid, and oleic acid; and mixtures thereof.

One type of lipophilic agent is selected from glycerides and derivatives thereof. Glycerides are selected from the group consisting of medium or long chain glycerides, caprylocaproyl macrogolglycerides, and mixtures thereof, for example. Medium chain glycerides can include, but are not limited to, medium chain monoglycerides, medium chain diglycerides, caprylic/capric triglyceride, glyceryl monolaurate, glyceryl mono stearate, caprylic/capric glycerides, glycerylmonocaprylate, glyceryl monodicaprylate, caprylic/capric linoleic triglyceride, and caprylic/capric/succinic triglyceride. Monoglycerides having a low melting point are specifically contemplated for making the formulation. Monoglycerides can include, but are not limited to, glyceryl monostearate, glyceryl monopalmitate, glyceryl monooleate, glyceryl monocaprylate, glyceryl monocaprate, glyceryl monolaurate, etc. Glycerol monostearate (GMS) is specifically contemplated. GMS is a natural emulsifying agent. It is oil soluble, but poorly soluble in water. GMS has an HLB value of 3.8. The lipophilic emulsifier can be present in an amount in a range of about 10 wt % to about 40 wt %, or about 20 wt % to about 25 wt %, for example. Other examples include about 20 wt %, about 21 wt %, about 22 wt %, about 23 wt %, about 24 wt %, and about 25 wt %.

Examples of suitable absorption enhancers include, but are not limited to, caprylocaproyl macrogolglycerides such as polyethylene glycosylated glycerides, also known as polyglycolized glycerides or PEGylated glycerides. PEGylated glycerides which may be employed in the composition include, but are not limited to, mixtures of monoglycerides, diglycerides, and triglycerides and monoesters and diesters of polyethylene glycol, polyethylene glycosylated almond glycerides, polyethylene glycosylated corn glycerides, and polyethylene glycosylated caprylic/capric triglyceride. The absorption enhancer can have an HLB value from 13 to 18, or from 13 to 15. One class of absorption enhancers is known under the trade name GELUCIRE (Gattefosse Corporation, Paramus, N.J., USA). GELUCIRE is a well-known excipient which is a family of fatty acid esters of glycerol and PEG esters, also known as polyglycolized glycerides. GELUCIRE is used in various applications including preparing sustained release pharmaceutical compositions. GELUCIRE compounds are inert, semi-solid waxy materials which are amphiphilic and are available with varying physical characteristics such as melting point, HLB, and solubilities in various solvents. They are surface active in nature and disperse or solubilize in aqueous media forming micelles, microscopic globules or vesicles. They are identified by their melting point/HLB value. The melting point is expressed in degrees Celsius. One or a mixture of different grades of GELUCIRE excipient may be chosen to achieve the desired characteristics of melting point and/or HLB value. GELUCIRE 44/14 (lauroyl macrogolglycerides/lauroyl polyoxylglycerides) has a melting point of 44° C. and a HLB of 14, and is particularly contemplated. The absorption enhancer can be present in an amount of about 5 wt % to about 20 wt %, or about 8 wt % to about 15 wt %, for example. Other examples include about 8 wt %, about 9 wt %, about 10 wt %, about 11, wt % about 12 wt %, about 13 wt %, about 14 wt %, and about 15 wt %.

Examples of other lipid matrices suitable for use with the methods of the invention include one or more of glycerides, fatty acids and alcohols, and fatty acid esters.

In one embodiment, a formulation may comprise an oily vehicle for the 25-hydroxyvitamin D compound. Any pharmaceutically-acceptable oil can be used. Examples include animal (e.g., fish), vegetable (e.g., soybean), and mineral oils. An oil can be selected to readily dissolve the 25-hydroxyvitamin D compound used. Oily vehicles can include non-digestible oils, such as mineral oils, particularly liquid paraffins, and squalene. The ratio between the wax matrix and the oily vehicle can be optimized in order to achieve the desired rate of release of the 25-hydroxyvitamin D compound. Thus, if a heavier oil component is used, relatively less of the wax matrix can be used, and if a lighter oil component is used, then relatively more wax matrix can be used. In one embodiment, the particular choice of oily vehicle provides a controlled release so that absorption of 25-hydroxyvitamin D is delayed until the formulation reaches the ileum and/or colon.

In one embodiment, a formulation may comprise a stabilizing agent such as a cellulose compound. Examples of cellulose compounds and stabilizing agents include, but are not limited to, celluloronic acid, carboxy methyl cellulose, ethyl cellulose, hydroxyl ethyl cellulose, hydroxyl propyl cellulose, hydroxyl propyl methyl cellulose (hypromellose), methylcellulose, polyanionic cellulose, and combinations thereof. Also contemplated are one or more of poloxamers (e.g., poloxamer 407), poly (ethylene oxide) polymers (e.g., Dow's POLYOX polymers), povidones, and fumed silicas (e.g., AEROSIL 200, Evonik Industries AG, Essen, Germany). The stabilizing agent, e.g., a cellulosic compound, can be present in an amount of at least about 5% of the formulation, based on the total weight of the formulation excluding any additional coatings or shells (wt %), for example. For example, the cellulosic compound can be present in an amount of at least 5 wt % of the formulation, or at least 10 wt % of the formulation, or at least 15 wt % of the formulation, or greater than 5 wt % of the formulation, or greater than 10 wt % of the formulation, or greater than 15 wt % of the formulation. Suitable ranges include 5 wt % to 30 wt %, 10 wt % to 20 wt %, 10 wt % to 15 wt %, 5 wt % to 15 wt %, and 7.5 wt % to 12.5 wt. %. Examples include about 5 wt %, about 6 wt %, about 7 wt %, about 8 wt %, about 9 wt %, about 10 wt %, about 11 wt %, about 12 wt %, about 13 wt %, about 14 wt %, and about 15 wt %. It will be understood that the stabilizing agent referred to herein is an agent that stabilizes the dissolution release profile (and thus also the in vivo release profile) against substantial change over time during storage conditions, e.g., typical shelf storage conditions. Other agents which are known in the art as preservatives for preventing degradation of the active component itself are not intended to be encompassed within the terms "stabilizing agent" and "stabilizer" although such preservatives are also contemplated for use in the formulations of the disclosure.

Specifically, in one suitable type of embodiment, the waxes selected for the matrix are melted and thoroughly mixed, optionally at a temperature of about 80° C. The desired quantity of oil(s), lauroyl polyoxylglycerides, mono- and di-glycerides, butylated hydroxytolulene, and hypromellose, are subsequently added, followed by sufficient mixing for homogenization. The waxy mixture is then gradually cooled to a temperature just above its melting point, optionally to a temperature in the range of about 50° C. to about 62° C. The mixing steps are optionally performed under vacuum. The desired amount of 25-hydroxyvitamin D, dissolved in ethanol, is uniformly distributed into the molten matrix, optionally under vacuum and/or at a temperature in a range of about 59° C. to about 62° C. The matrix is loaded into capsules, for example vegetable-based or gelatin-based capsules, optionally under vacuum and/or at a temperature in a range of about 63° C. to about 70° C.

The filled capsules optionally are treated for appropriate periods of time with a solution containing an aldehyde, such as acetaldehyde, to partially crosslink a polymer, e.g., gelatin, in the capsule shell, when used. The capsule shell becomes increasingly crosslinked, over a period of several weeks and, thereby, more resistant to dissolution in the contents of stomach and upper intestine. When properly constructed, this gelatin shell will gradually dissolve after oral administration and become sufficiently porous (without fully disintegrating) by the time it reaches the ileum to allow the 25-hydroxyvitamin D to diffuse slowly from the wax matrix into the contents of the lower small intestine and/or colon.

Another suitable controlled-release oral drug delivery system is the EUDRAGIT RL/RS system in which the active 25-hydroxyvitamin D ingredient is formed into granules having a dimension of 25/30 mesh. The granules are then uniformly coated with a thin polymeric lacquer, which is water-insoluble but slowly water-permeable. The coated granules can be mixed with optional additives including one or more of antioxidants, stabilizers, binders, lubricants, processing aids and the like. The mixture may be compacted into a tablet which, prior to use, is hard and dry and can be further coated, or it may be poured into a capsule. After the tablet or capsule is swallowed and comes into contact with the aqueous intestinal fluids, the thin lacquer begins to swell and slowly allows permeation by intestinal fluids. As the intestinal fluid slowly permeates the lacquer coating, the contained 25-hydroxyvitamin D is slowly released. By the time the tablet or capsule has passed through the small intestine, about four to eight hours or more later, the 25-hydroxyvitamin D will have been slowly, but completely, released. Accordingly, the ingested tablet will release a stream of 25-hydroxyvitamin D, as well as any other active ingredient.

The EUDRAGIT system is comprised of high permeability lacquers (RL) and low permeability lacquers (RS). RS is a water-insoluble film former based on neutral swellable methacrylic acids esters with a small proportion of trimethylammonioethyl methacrylate chlorides; the molar ratio of the quaternary ammonium groups to the neutral ester group is about 1:40. RL is also a water insoluble swellable film former based on neutral methacrylic acid esters with a small portion of trimethylammonioethyl methacrylate chloride, the molar ratio of quaternary ammonium groups to neutral ester groups is about 1:20. The permeability of the coating and thus the time course of drug release can be titrated by varying the proportion of RS to RL coating material. For further details of the Eudragit RL/RS system, reference is made to technical publications available from Rohm Tech, Inc. 195 Canal Street, Maiden, Mass., 02146 and Lehmann et al., *Int. J. Pharm. Tech. & Prod. Mfr.* 2(r), 31-43, 1981, incorporated herein by reference.

Other examples of insoluble polymers include polyvinyl esters, polyvinyl acetals, polyacrylic acid esters, butadiene styrene copolymers and the like.

In one embodiment, once the coated granules are either formed into a tablet or put into a capsule, and the tablet or capsule is coated with an enteric-coating material which dissolves at a pH of 7.0 to 8.0. One such pH-dependent enteric-coating material is EUDRAGIT L/S which dissolves in intestinal fluid, but not in the gastric juices. Other enteric-coating materials may be used such as cellulose acetate phthalate (CAP), which is resistant to dissolution by gastric juices, but readily disintegrates due to the hydrolytic effect of the intestinal esterases.

In one embodiment, the particular choice of enteric-coating material and controlled release coating material provides a controlled and substantially constant release over a period of 4 to 8 hours or more so that substantial release is delayed until the formulation reaches the ileum. Optionally, a controlled release composition in accordance with the present disclosure, when administered once a day, can suitably provide substantially constant intralumenal, intracellular and blood 25-hydroxyvitamin D levels compared to an equal dose of an immediate release composition of 25-hydroxyvitamin D administered once a day.

The dosage forms may also contain adjuvants, such as preserving adjuvants. Formulations according to the invention may also contain other therapeutically valuable substances or may contain more than one of the compounds specified herein and in the claims in admixture.

As an alternative to oral 25-hydroxyvitamin D, intravenous administration of 25-hydroxyvitamin D is also contemplated. In one embodiment, the 25-hydroxyvitamin D is administered as a sterile intravenous injection, optionally a bolus injection of a composition that results in a sustained release profile. In another embodiment, the 25-hydroxyvitamin D is administered via gradual injection/infusion, e.g., over a period of 1 to 5 hours, to effect controlled or substantially constant release of the 25-hydroxyvitamin D directly to DBP in the blood of the patient. For example, the composition may be injected or infused over a course of at least about 1 hour, at least about 2 hours, at least about 3 hours, at least about 4 hours, at least about 5 hours, or at least about 6 hours, and up to 24 hours, for example. In one embodiment, the composition intended for intravenous administration in accordance with disclosure is designed to contain a concentration of the 25-hydroxyvitamin D compound(s) of 1 to 100 mcg per unit dose. Sterile, isotonic formulations of 25-hydroxyvitamin D may be prepared by dissolving 25-hydroxyvitamin D in absolute ethanol, propylene glycol or another suitable solvent, and combining the resulting solution with one or more surfactants, salts and preservatives in appropriate volumes of water for injection. Such formulations can be administered slowly from syringes, for example, via heparin locks, or by addition to larger volumes of sterile solutions (e.g., saline solution) being steadily infused over time.

A particular formulation of 25-hydroxyvitamin $D_3$ for use in the methods of the disclosure is an extended release oral formulation comprising 25-hydroxyvitamin D (e.g., about 30 mcg, about 60 mcg, about 90 mcg, about 150 mcg, about 300 mcg, about 450 mcg, about 600 mcg, about 750 mcg, or about 900 mcg 25-hydroxyvitamin $D_3$), about 2 wt % (e.g., 2.32 wt %) anhydrous/dehydrated ethanol, about 10 wt % (e.g., 9.75 wt %) lauroyl polyoxylglycerides (e.g., GELUCIRE 44/14), about 20 wt % (e.g., 20.00 wt. %) hard paraffin, about 23 wt % (e.g., 22.56 wt %) mono- and di-glycerides (e.g., GMS), about 35 wt % (e.g., 35.34 wt %) liquid paraffin or mineral oil, about 10 wt % hypromellose, and optionally a small amount of preservative (e.g., 0.02 wt % BHT). The formulation is optionally encased in a soft capsule shell, for example, a capsule shell comprising modified starch, carrageenan (e.g., iota and/or kappa), sodium phosphate, dibasic, sorbitol sorbitan solution, dye (e.g., FD&C Blue #1), titanium dioxide and purified water. In one aspect, the 90% confidence interval (90% CI) of the ratio of the mean Cmax between a test formulation and a formulation of the disclosure is in the range of 80% to 125% (0.8-1.25). In another aspect, the 90% confidence interval (90% CI) of the ratio of the mean $AUC_{(0-inf)}$ between a test formulation and a formulation of the disclosure is in the range of 80% to 125% (0.8-1.25). Optionally, the 90% confidence interval (90% CI) of the ratio of the Tmax between a test formulation and a formulation of the disclosure is in the range of 80% to 125% (0.8-1.25). A formulation which is bioequivalent to a formulation described herein is also specifically contemplated for use in the methods of the disclosure.

In one aspect, the disclosure provides a method of treating secondary hyperparathyroidism in a patient with Chronic Kidney Disease Stage 3 or Stage 4 and serum total 25-hydroxyvitamin D levels less than 30 ng/mL comprising administering an oral extended release formulation of calcifediol. Optionally, the patient has a serum calcium level less than 9.8 mg/dL and/or a serum phosphorus level less than 5.5 mg/dL. Optionally, the method comprises administering an oral extended release formulation of 25-hydroxyvitamin $D_3$ comprising 30 mcg calcifediol once daily, for example, at bedtime. In one embodiment, the method comprises administering 60 mcg calcifediol to raise serum total 25-hydroxyvitamin D into the range of 30 ng/mL to 100 ng/mL and to lower plasma intact parathyroid hormone (iPTH) to the iPTH treatment goal provided that serum calcium is within the normal reference range. In various embodiments, the method comprises administering from about 30 mcg to about 60 mcg calcifediol daily. In some embodiments, the method comprises administering 25-hydroxyvitamin D in a range of about 300 mcg to about 900 mcg per week, e.g. 600 mcg per week, optionally divided into two or three doses per week, e.g. three times per week at dialysis treatment.

In one embodiment, calcifediol is synthetically manufactured as calcifediol monohydrate. Calcifediol monohydrate is a white crystalline powder, has a calculated molecular weight of 418.65 and is soluble in alcohol and fatty oils but practically insoluble in water. Chemically, calcifediol monohydrate is (3β,5Z,7E)-9,10-secocholesta-5,7,10(19)-triene-3,25-diol monohydrate and its structural formula is:

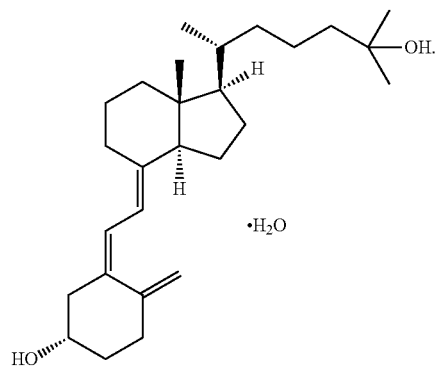 [SMILES: C=C1CC[C@H](O)C/C1=C/C=C1\CCC[C@]2(C)[C@@H]([C@H](C)CCCC(C)(C)O)CC[C@@H]12 ; O]

The present invention is further explained by the following examples which should not be construed by way of limiting the scope of the present invention.

Example 1

Phase III Clinical Trial of Extended Release 25-Hydroxyvitamin $D_3$ in Patients with CKD Stage 3 or 4

The efficacy and safety of an extended release formulation of 25-hydroxyvitamin $D_3$ (RAYALDEE, Opko Ireland Global Holdings Ltd.) were evaluated in two identical multicenter, randomized, placebo-controlled, double-blind studies involving patients with secondary hyperparathyroidism (iPTH>85 pg/mL), stage 3 or 4 chronic kidney disease and associated serum total 25-hydroxyvitamin D levels ≥10 ng/mL and ≤30 ng/mL. Subjects were stratified by disease stage and randomized in a 2:1 ratio to receive a once daily 30 mcg oral dose of RAYALDEE (or matching placebo) at bedtime for 12 weeks followed by an additional 14 weeks of treatment with a once daily oral dose of either 30 or 60 mcg of RAYALDEE (or placebo) at bedtime. Each capsule contained the following excipients: mineral oil, monoglycerides and diglycerides, paraffin, hypromellose, lauroyl polyoxylglycerides, dehydrated alcohol and butylated hydroxytoluene. The capsule shells contained modified starch, carrageenan, sodium phosphate, dibasic, sorbitol sorbitan solution, FD&C Blue #1, titanium dioxide and purified water. Medium chain triglyceride (fractionated coconut) oil was used as a lubricant during manufacture, and trace amounts may have been present in the final formulation.

A total of 213 subjects were randomized in one study (72 received placebo and 141 received RAYALDEE), and 216 subjects were randomized in the other (72 received placebo and 144 received RAYALDEE). The subjects' mean age was 66 years (range 25-85), 50% were male, 65% White, 32% African-American or Black and 3% Other. At baseline, subjects had secondary hyperparathyroidism, Stage 3 (52%) or Stage 4 (48%) CKD without macroalbuminuria and serum total 25-hydroxyvitamin D levels less than 30 ng/mL. The most common causes of CKD were diabetes and hypertension and the mean estimated GFR at baseline was 31 mL/min/1.73 m². At baseline, mean serum intact PTH was 148 pg/mL, mean serum calcium was 9.2 mg/dL, mean serum phosphorus was 3.7 mg/dL and mean serum 25-hydroxyvitamin D was 20 ng/mL. Mean baseline iPTH was 130 pg/mL for subjects with Stage 3 disease (n=222) and 166 pg/mL for subjects with Stage 4 disease (n=207). Of the 429 subjects, 354 (83%) completed the studies and 298 (69%) elected to continue treatment for an additional 6 months with RAYALDEE during an open-label extension study. All subjects started on a dose of 30 mcg, administered once daily at bedtime, and most (210, 74%) increased to 60 mcg after 12 weeks if the plasma intact PTH level was greater than 70 pg/mL, the serum 25-hydroxyvitamin D level was less than 65 ng/mL and the serum calcium level was less than 9.8 mg/dL.

The primary analysis compared the proportion of individuals who experienced an at least 30% reduction in plasma intact PTH from baseline to end of trial (average of weeks 20, 22, 24 and 26). A larger proportion of patients randomized to RAYALDEE experienced an at least 30% reduction in plasma intact PTH from baseline compared to placebo in both trials (33% versus 8% in the first trial (P<0.001) and 34% versus 7% in the second trial (P<0.001)).

Figure 1B:
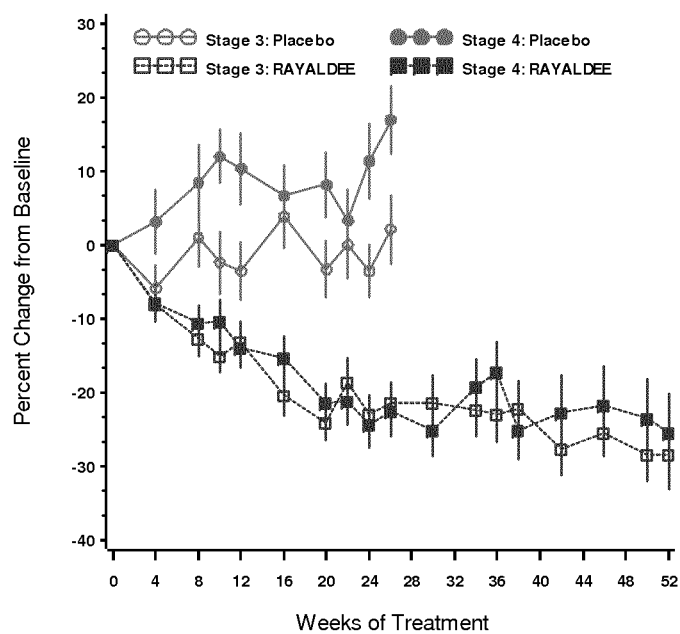
FIG. 1B shows the mean (±SE) change from baseline in plasma iPTH in CKD Stage 3 subjects administered a placebo (open circles), CKD Stage 3 subjects administered an extended release formulation of 25-hydroxyvitamin $D_3$ (open squares), CKD Stage 4 subjects administered a placebo (closed circles), and CKD Stage 4 subjects administered an extended release formulation of 25-hydroxyvitamin $D_3$ (closed squares) for up to 62 weeks.
Figure 1C:
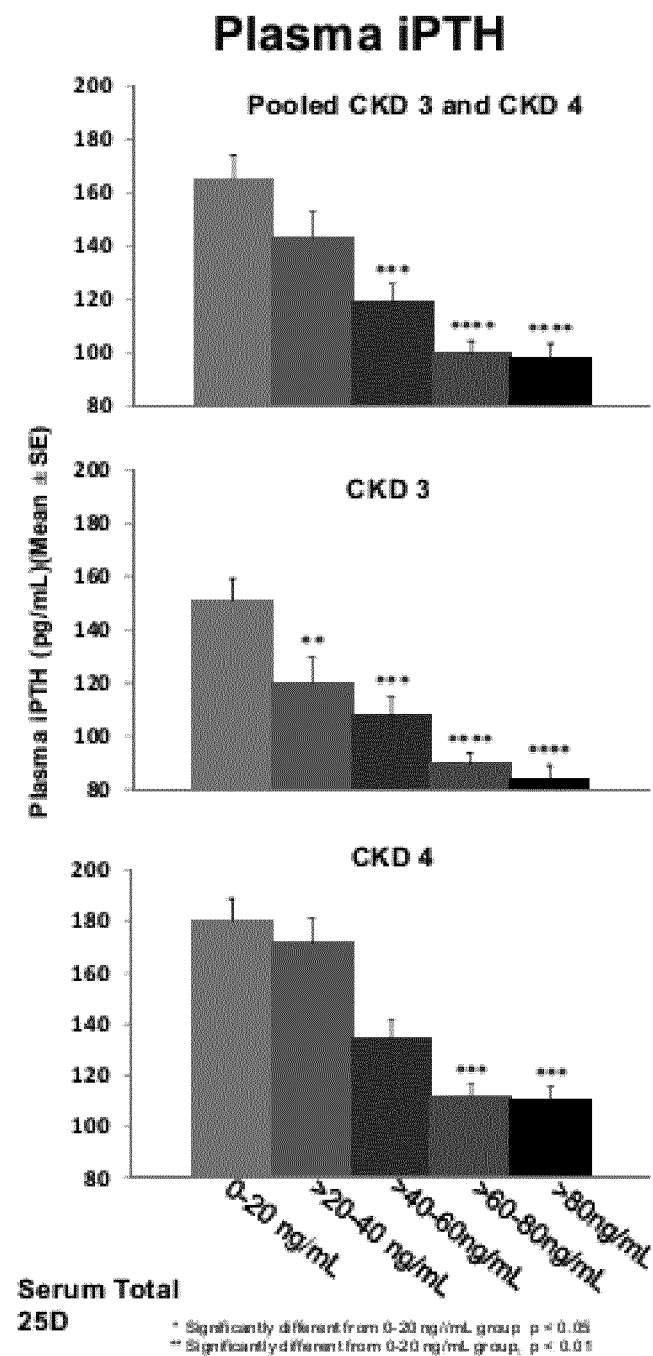
FIG. 1C shows the mean (±SE) plasma iPTH level (pg/mL) compared to the serum total 25-hydroxyvitamin D level (ng/mL) in subjects having CKD Stage 3 or Stage 4 (top graph), CKD Stage 3 (middle graph) or CKD Stage 4 (bottom graph). Asterisks denote statistical significance from the group having serum total 25-hydroxyvitamin D of 0-20 ng/mL.

Mean plasma iPTH gradually declined to near normal levels over 1 year of treatment with RAYALDEE, regardless of CKD stage, but increased with placebo treatment. At the end of 26 weeks of treatment, mean pooled plasma iPTH had declined by 22±32% with RAYALDEE treatment, but increased by 9±36% with placebo treatment (FIG. 1A), with comparable efficacy in CKD Stage 3 and Stage 4 (FIG. 1B). iPTH suppression was directly proportional to elevation of serum total 25-hydroxyvitamin D (FIG. 1C) and was sustained during the 6-month extension study.

Figure 2A:
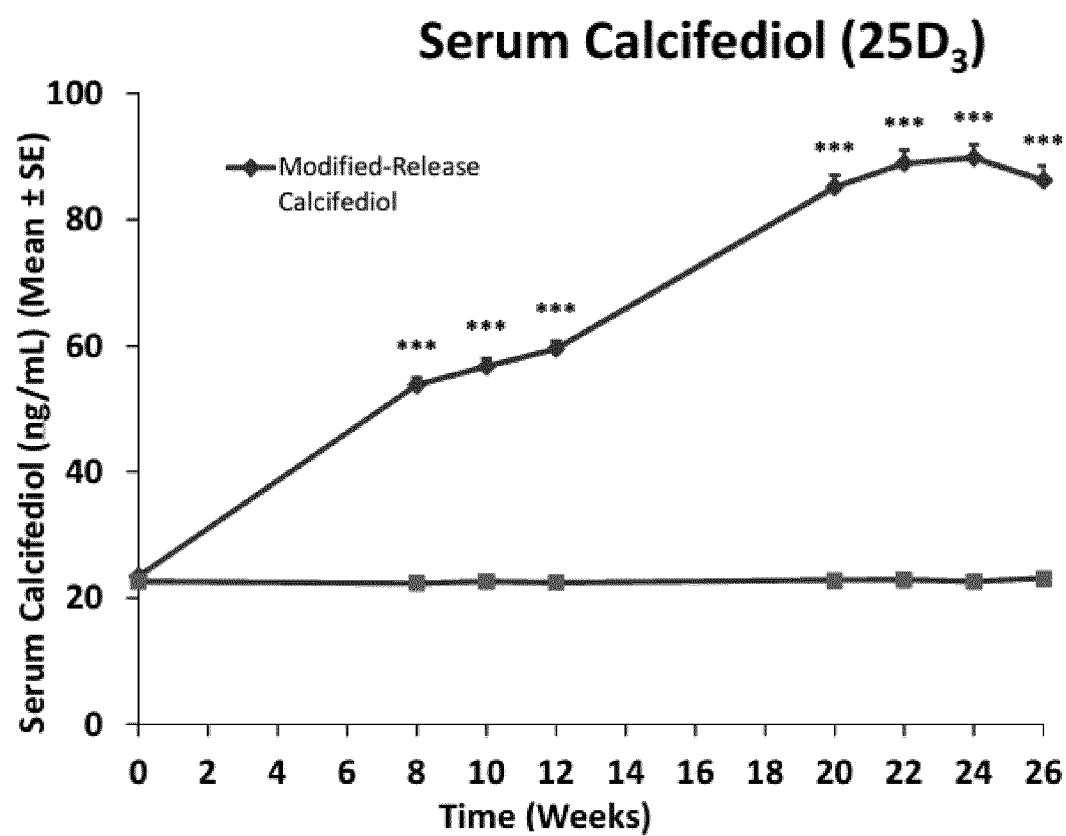
FIG. 2A shows the mean (±SE) serum calcifediol (ng/mL) in subjects administered a placebo (squares) or an extended release formulation of 25-hydroxyvitamin $D_3$ (diamonds) for 26 weeks. Triple asterisks (***) denote a significant difference from placebo, $p<0.0001$.

Serum total 25-hydroxyvitamin D levels gradually increased to ≥30 ng/mL in 80% and 83% of subjects treated with RAYALDEE versus 3% and 7% of subjects treated with placebo (p<0.001) in the two studies. Average steady-state levels were 50±20 and 56±19 ng/mL for subjects receiving 30 mcg daily, and 69±22 and 67±21 ng/mL for subjects receiving 60 mcg daily, in the first and second studies, respectively (FIG. 2A). Serum 25-hydroxyvitamin D levels as high as about 185 ng/mL were achieved without any adverse reactions. The results were comparable to a prior repeat-dose clinical study, wherein 30 mcg daily doses of RAYALDEE produced incremental increases in mean serum 25-hydroxyvitamin D of up to a total of 5.8±1.2 (SE) ng/mL/week and a corresponding increase in mean serum 1,25-dihydroxyvitamin D of up to a total of 6.7±3.1 pg/mL/week. Reductions in circulating plasma intact PTH were observed within the first two weeks of RAYALDEE treatment.

Figure 2B:
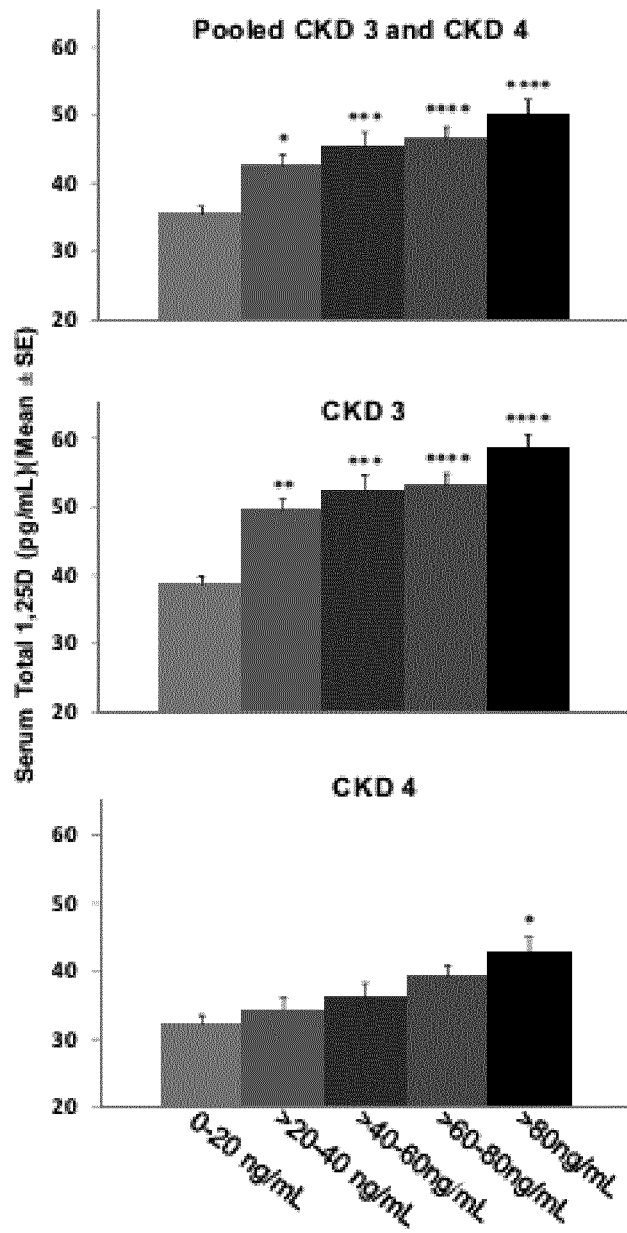
FIG. 2B shows the mean (±SE) serum total 1,25-dihydroxyvitamin D level (pg/mL) compared to the serum total 25-hydroxyvitamin D level (ng/mL) in subjects having CKD Stage 3 or Stage 4 (top graph), CKD Stage 3 (middle graph) or CKD Stage 4 (bottom graph). Asterisks denote statistical significance from the group having serum total 25-hydroxyvitamin D of 0-20 ng/mL.

Plasma iPTH and serum total 25-hydroxyvitamin D response rates were similar in Stages 3 and Stage 4 CKD, as were increases in serum total 25-hydroxyvitamin D and 1,25 dihydroxyvitamin D. Mean serum total 1,25D significantly increased by the end of the treatment period, regardless of CKD stage (FIG. 2B).

Of the 285 subjects treated with RAYALDEE, 179 had $24,25(OH)_2D_3$ levels at baseline that were above LOQ (<0.51 ng/mL). Over 26 weeks of RAYALDEE treatment, mean 25(OH)D3 and 24,25(OH)2D3 increased significantly (p<0.0001 vs. placebo) from baseline of 29 to 87 ng/mL and 1.0 to 4.1 ng/mL (FIG. 3A), respectively; mean iPTH decreased significantly (p<0.0001) from 147 to 111 pg/mL compared to a mean increase in placebo subjects. The 25(OH)D3:24,25(OH)2D3 ratios were variable (RSD~30%), but decreased with RAYALDEE treatment from a mean of 30 to 25 (FIG. 3B), and after 26 weeks were significantly lower than with placebo (p<0.0001). The results indicated that the ratio of $25(OH)D_3:24,25(OH)_2D_3$ is useful for diagnosing VDI in CKD patients. The data further indicated that reducing this ratio to <20 would require $25(OH)D_3$ levels higher than 85 ng/mL, demonstrating that the target for 25(OH)D is higher than expected in CKD patients compared to normal subjects.

No differences in urine calcium or phosphorus were observed between treatment groups. Mean serum Ca and P levels in subjects treated with extended release calcifediol were generally similar to placebo-treated subjects (FIG. 6A); slight elevations were noted at several time points. Mean±SD serum calcium corrected for albumin increased in pooled data from a baseline of 9.2±0.3 mg/dL by 0.2±0.3 mg/dL with RAYALDEE compared to 0.1±0.3 mg/dL with placebo treatment. Serum phosphorus increased with RAYALDEE by 0.2±0.5 mg/dL from a baseline of 3.7±0.6 mg/dL with RAYALDEE compared to 0.1±0.4 mg/dL from a baseline of 3.8±0.5 with placebo treatment. No exposure-response relationship was observed for serum calcium (FIG. 6B) or serum phosphorus (FIG. 6C) based on the amount of 25-hydroxyvitamin $D_3$ administered. A total of 6 subjects (2%) in the RAYALDEE treatment group required dose reductions after meeting the protocol-defined criterion of albumin-corrected hypercalcemia (two consecutive serum calcium values ≥10.3 mg/dL), compared to no subjects in the placebo group. Five of these subjects had a history of serum calcium ≥9.8 mg/dL prior to treatment, and the sixth subject had received concomitant thiazide therapy. A total of 4.2% of RAYALDEE subjects and 2.1% of placebo subjects experienced ≥1 elevation in serum calcium above the upper limit of normal (10.5 mg/dL). Adverse events of "blood calcium increased" or "hypercalcemia" were reported in 0.7% of subjects in the RAYALDEE and 1.4% in the placebo treatment groups. One subject (0.4%) in the RAYALDEE treatment group met the protocol-defined criterion of hyperphosphatemia (two consecutive serum phosphorus values ≥5.5 mg/dL deemed to be study drug related) and required dose reduction, compared to no subjects in the placebo group. A total of 45.6% of RAYALDEE subjects and 44.4% of placebo subjects experienced ≥1 elevation in serum phosphorus above the upper limit of normal (4.4 mg/dL). Adverse events of "blood phosphorus increased" or "hyperphosphatemia" were reported in 1.8% of subjects in the RAYALDEE and 2.8% in the placebo treatment groups.

Figures 6D, 6E:
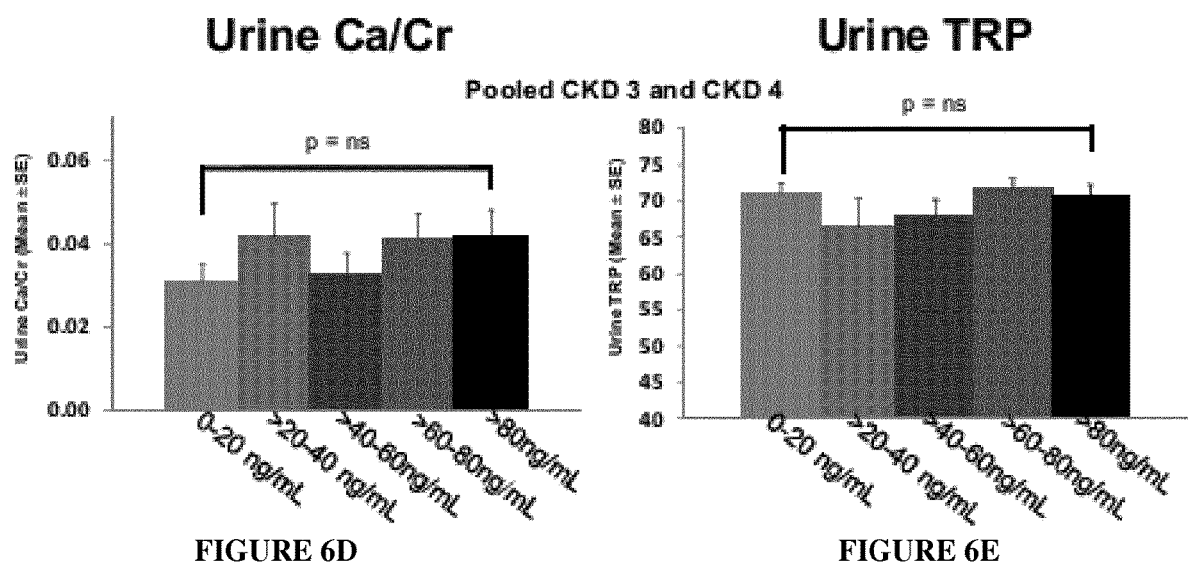
FIG. 6D shows the mean (±SE) urine calcium/creatinine ratio (Ca/Cr) and FIG. 6E shows the mean urine tubular reabsorption of phosphate (TRP) compared to the serum total 25-hydroxyvitamin D level for CKD Stage 3 and Stage 4 patients administered an extended release formulation of 25-hydroxyvitamin $D_3$ for 26 weeks.
Figure 7A:
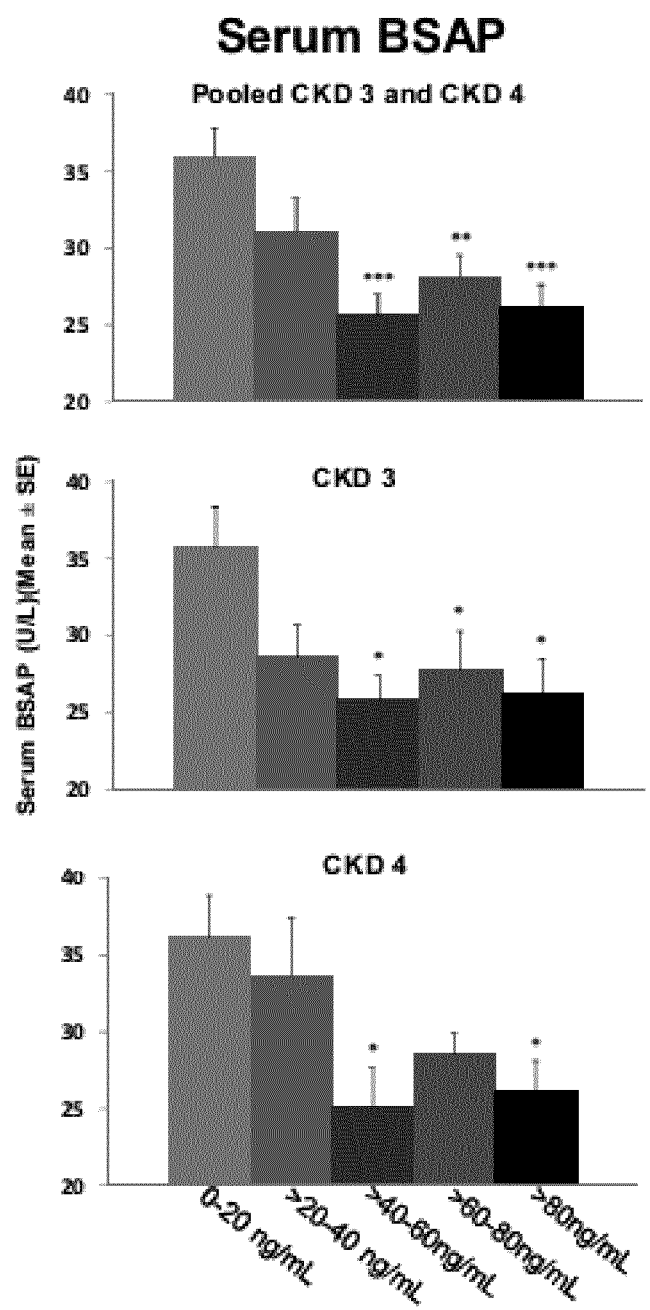
FIG. 7A shows the mean (±SE) serum bone-specific alkaline phosphatase (BSAP) (U/L) compared to the serum total 25-hydroxyvitamin D level (ng/mL) in subjects having CKD Stage 3 or Stage 4 (top graph), CKD Stage 3 (middle graph) or CKD Stage 4 (bottom graph).
Figure 7B:
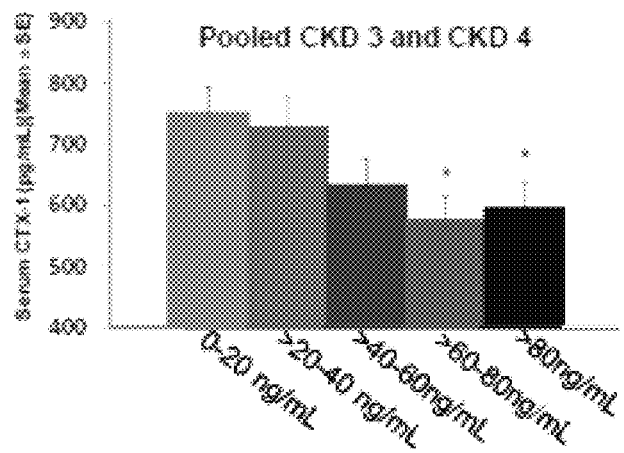
FIG. 7B shows the mean (±SE) serum collagen type 1 cross-linked C-telopeptide (CTX-1) (pg/mL) (top graph) and FIG. 7C shows the mean (±SE) serumtype 1 procollagen N-terminal (P1NP) (ng/mL) (bottom graph) compared to the serum total 25-hydroxyvitamin D level (ng/mL) in subjects having CKD Stage 3 or Stage 4. Asterisks denote statistical significance compared to the group having serum total 25-hydroxyvitamin D of 0-20 ng/mL.
Figure 7C:
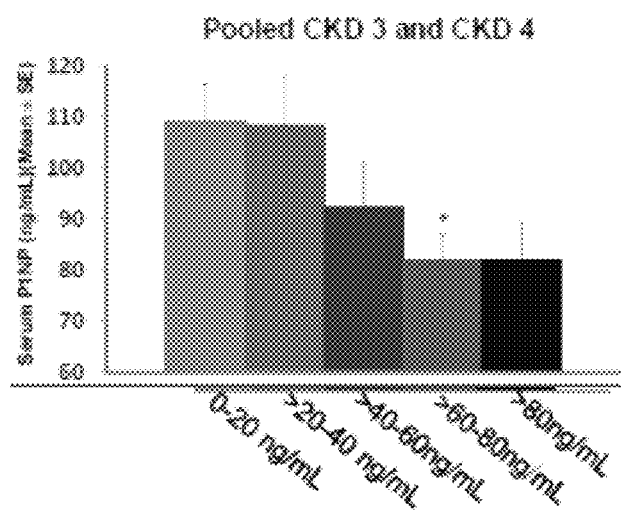

Markers of bone turnover decreased during treatment with RAYALDEE. Urine calcium/creatinine ratio (Ca/Cr) and Tubular Reabsorption of Phosphorus (TRP) were unchanged (FIGS. 6D and 6E). Serum total alkaline phosphatase decreased from 93 to 87 U/L, serum bone-specific alkaline phosphatase (BSAP) decreased from 38 to 27 U/L (FIG. 7A), serum C-Terminal Telopeptide-1 (CTX-1) decreased from 734 to 612 pg/mL (FIG. 7B), and serum Procollagen-1 Amino-terminal Propeptide (P1NP) decreased from 99 to 89 ng/mL (FIG. 7C). During placebo administration, these bone markers either increased or remained relatively unchanged.

A food effect study with a supratherapeutic dose of 450 mcg in healthy subjects showed an approximately 5-fold increase in maximum serum calcifediol concentration (Cmax) and a 3.5-fold increase in $AUC_{0-t}$ when RAYALDEE was administered with a high fat, high calorie meal compared to fasting.

A single-dose study with a supratherapeutic dose of 900 mcg in healthy subjects produced maximum blood calcifediol concentrations in the range of 21 to 32 hours after dosing in the fasted state.

Example 2

Pharmacokinetic Studies

The pharmacokinetics of RAYALDEE were assessed in healthy subjects and subjects with CKD Stage 3 or Stage 4. Exposure to calcifediol increased proportionally over the dose range of 30 to 90 mcg following repeated daily administration of RAYALDEE at bedtime to subjects with secondary hyperparathyroidism, chronic kidney disease and vitamin D insufficiency. Steady-state levels of serum total 25-hydroxyvitamin D were reached after approximately 3 months. Following multiple dose administration of RAYALDEE, the average steady state concentrations of serum total 25-hydroxyvitamin D were 53 ng/mL and 68 ng/mL for doses of 30 mcg and 60 mcg dose group, respectively. With respect to distribution, calcifediol is extensively bound to plasma proteins (>98%). The mean apparent volume of distribution was 8.8 L in healthy subjects following a single oral dose of RAYALDEE, and 30.1 L in subjects with Stage 3 or Stage 4 chronic kidney disease following repeated dosing. With respect to elimination, the mean elimination half-life of calcifediol was approximately 11 days in healthy individuals following a single dose of RAYALDEE, and approximately 25 days in patients with Stage 3 or Stage 4 chronic kidney disease following repeated once daily dosing. With respect to metabolism, production of calcitriol from calcifediol is catalyzed by the 1α-hydroxylase enzyme, CYP27B1, located in the kidney, parathyroid gland, and other tissues. CYP24A1, located in all vitamin D responsive tissues, catabolizes both calcifediol and calcitriol to inactive metabolites. Calcitriol suppresses CYP27B1 and upregulates CYP24A1. Excretion of calcifediol occurs primarily through the biliary fecal route. No effect of CKD stage on steady-state calcifediol concentrations was evident following daily RAYALDEE administration, in an analysis of population pharmacokinetics in subjects with CKD Stage 3 or Stage 4. Table 1 shows a summary of baseline-adjusted pharmacokinetic parameters for calcifediol by treatment group.

TABLE 1

|  | Placebo | 30 μg | 60 μg | 90 μg |
|---|---|---|---|---|
| Baseline (ng/mL) | | | | |
| Mean (SD) | 16.4 (8.2) | 16.2 (7.3) | 19.8 (8.7) | 18.4 (9.8) |
| Median | 12.9 | 17.2 | 21.2 | 16.7 |
| Minimum, Maximum | 4.4, 30.4 | 5.0, 25.8 | 5.8, 32.5 | 6.7, 38.9 |
| $C_{max}$ (ng/mL) | | | | |
| Mean (SD) | 4.1 (3.5) | 27.8 (8.2) | 60.3 (19.0) | 85.7 (26.9) |
| Median | 3.1 | 28.1 | 60.8 | 76.0 |
| Minimum, Maximum | 0.6, 13.8 | 10.8, 43.4 | 30.3, 89.5 | 55.4, 146.4 |
| $AUC_{0-6\ Weeks}$ (ng · d/mL) | | | | |
| Mean (SD) | 45.9 (60.0) | 709.2 (246.3) | 1531.4 (374.8) | 2134.3 (584.3) |
| Median | 32.1 | 684.3 | 1573.0 | 1963.8 |
| Minimum, Maximum | −60.1, 222.3 | 307.8, 1249.0 | 712.7, 2221.8 | 1377.5, 3207.3 |
| $t_{max}$ (d) | | | | |
| Mean (SD) | NA | 37.8 (10.4) | 41.1 (5.2) | 42.6 (5.3) |
| Median | NA | 42.50 | 43.0 | 43.0 |
| Minimum, Maximum | NA | 8.0, 44.0 | 29.0, 45.0 | 35.0, 57.0 |
| $t_{1/2}$ (d) | | | | |
| Mean (SD) | NA | 25.8 (16.3) | 33.1 (9.3) | 50.1 (51.0) |
| Median | NA | 24.1 | 31.6 | 37.7 |
| Minimum, Maximum | NA | 5.2, 52.6 | 17.4, 52.3 | 23.2, 224.0 |

Table 2 shows a summary of baseline-adjusted pharmacokinetic parameters for 1,25-dihydroxyvitamin D by treatment group.

TABLE 2

|  | Placebo N = 23 | 30 μg N = 12 | 60 μg N = 16 | 90 μg N = 14 |
|---|---|---|---|---|
| Baseline (pg/mL) | | | | |
| Mean (SD) | 20.8 (10.11) | 18.3 (7.53) | 20.6 (7.62) | 20.6 (7.29) |
| Median | 17.0 | 17.0 | 18.0 | 21.0 |
| Minimum, Maximum | 7.0, 41.4 | 5.1, 30.7 | 8.2, 33.6 | 9.3, 34.5 |
| $C_{max}$ (pg/mL) | | | | |
| Mean (SD) | 7.6 (5.71) | 6.4 (7.66) | 18.4 (6.24) | 19.9 (14.30) |
| Median | 4.9 | 5.0 | 18.4 | 18.9 |
| Minimum, Maximum | 1.9, 22.6 | −6.3, 21.0 | 7.3, 29.9 | −11.6, 48.3 |
| $AUC_{0-6\ Weeks}$ (g · d/mL) | | | | |
| Mean (SD) | 11.5 (112.97) | 100.6 (185.38) | 249.9 (198.83) | 371.1 (290.81) |
| Median | 16.2 | 23.0 | 298.7 | 352.2 |
| Minimum, Maximum | −267.1, 219.8 | −145.4, 452.3 | −191.7, 563.6 | −5.8, 1235.8 |

TABLE 2-continued

|  | Placebo<br>N = 23 | 30 µg<br>N = 12 | 60 µg<br>N = 16 | 90 µg<br>N = 14 |
|---|---|---|---|---|
| $t_{max}$ (d) | | | | |
| Mean (SD) | 24.4 (15.55) | 16.8 (16.09) | 26.4 (11.52) | 25.5 (13.88) |
| Median | 23.0 | 12.0 | 23.0 | 23.00 |
| Minimum, Maximum | 2.0, 45.0 | 1.0, 44.0 | 8.0, 44.0 | 1.0, 44.0 |

Example 3

Clinical Trial of Extended Release 25-Hydroxyvitamin $D_3$ in Patients with CKD Stage 5

A multi-center, randomized, double-blind, placebo-controlled study clinical study is conducted to evaluate the safety and efficacy of three weekly doses of an extended release formulation of 25-hydroxyvitamin $D_3$ versus placebo in reducing serum intact parathyroid hormone (iPTH) by at least 30% from pre-treatment baseline in subjects with secondary hyperparathyroidism, vitamin D insufficiency and CKD Stage 5, who are undergoing hemodialysis three times per week. The extended release formulation of 25-hydroxyvitamin $D_3$ is provided as a capsule having the same formulation as RAYALDEE, but containing 150 mcg 25-hydroxyvitamin $D_3$. Approximately 600 subjects are screened to randomize approximately 280 eligible subjects balanced for severity of SHPT in a 1:1:1:1 ratio into four parallel groups receiving the following treatments for 52 weeks: (a) extended release formulation of 25-hydroxyvitamin $D_3$ at 300 mcg per week, (b) extended release formulation of 25-hydroxyvitamin $D_3$ at 600 mcg per week, (c) extended release formulation of 25-hydroxyvitamin $D_3$ at 900 mcg per week, or (d) matching placebo.

To be enrolled in the study, subjects must be at least 18 years of age and diagnosed with CKD Stage 5 requiring in-center hemodialysis three times a week for the preceding 9 months, as confirmed by medical history. During the screening visit, subject must exhibit a serum iPTH level ≥150 pg/mL and <600 pg/mL, if receiving calcitriol or active vitamin D analogue, or a serum iPTH level ≥400 pg/mL and <900 pg/mL, if not receiving calcitriol or active vitamin D analogue. Subjects receiving treatment with cinacalcet, etelcalcetide, calcitriol or other 1-hydroxylated vitamin D analogues, or vitamin D supplementation at a rate about 1,000 IU/day forgo further dosing with these agents for the duration of the study and complete a 4-week washout period prior to the 52-week treatment period, to achieve serum iPTH≥400 pg/mL and <900 pg/mL, serum calcium <9.8 mg/dL, and serum total 25-hydroxyvitamin D<30 ng/mL.

Blood samples are collected at the start of the mid-week dialysis session from all subjects for safety and efficacy assessments at weekly or biweekly intervals during the pre-treatment washout period, the 52-week treatment period and the 6-week post-treatment follow-up period. Enrolled subjects in the 600 mcg or 900 mcg group receive one or two capsules containing 150 mcg 25-hydroxyvitamin $D_3$ or placebo three times per week (e.g., on a Monday, Wednesday, Friday schedule or a Tuesday, Thursday, Saturday schedule) for 52 weeks. Subjects in the 300 mcg group receive one capsule containing 150 mcg 25-hydroxyvitamin $D_3$ two times per week (e.g., on Monday/Tuesday and Friday/Saturday). The capsules are administered in the dialysis center at the end of regularly scheduled hemodialysis to achieve the total cumulative weekly dose. Subjects undergo hemodialysis during the study with a dialysate calcium concentration of ≤2.5 mEq/l. Additional blood samples are collected in a subset of subjects from each treatment group during the post-treatment follow-up period in order to establish the pharmacokinetic profile of serum 25-hydroxyvitamin $D_3$ after the last administered dose.

Subjects are eligible for dose titration at the start of week 26 provided that (a) iPTH has not decreased by at least 40% from pretreatment baseline and remains >300 pg/mL, (b) serum calcium is <9.8 mg/dL, (c) serum phosphorus is <6.0 mg/dL, and (d) the currently assigned dosage in the trial is less than 900 mcg/week. Dose titration will occur in increments of 300 mcg/week unless a lower increment is necessary in order to keep the maximum dose from exceeding 900 mcg/week. Subjects reduce the dose by 150 mcg per week in the event that iPTH is confirmed to be <150 pg/mL, serum calcium is confirmed to be >10.3 mg/dL, or serum phosphorus is confirmed to be >6.5 mg/dL, provided that that the investigator deems the elevated serum phosphorus to be related to study drug administration and has taken appropriate and persistent actions to control serum phosphorus by initiating or adjusting phosphate binder therapy. Subjects suspend dosing if iPTH is confirmed to be <100 pg/mL or serum calcium is confirmed to be >11.0 mg/dL, and resume when iPTH is ≥150 pg/mL and serum calcium is ≤9.8 mg/dL at a dose that has been reduced by 150 mcg per week. Subjects who experience more than a 100% increase in iPTH from pre-treatment baseline or exhibit iPTH above 1,200 pg/mL on two consecutive visits (if at least 2 weeks apart) terminate dosing with study drugs and further participation in the treatment period and immediately enter the post-treatment follow-up period.

Key parameters monitored at regular intervals during the study include: iPTH, serum calcium, serum phosphorus, serum total 25-hydroxyvitamin D, serum total 1,25-dihydroxyvitamin D, serum 25-hydroxyvitamin $D_3$; serum 1,25-dihydroxyvitamin $D_3$, serum 24,25-dihydroxyvitamin $D_3$, vital signs (VS), and adverse events (AEs). Electrocardiograms are conducted at baseline and during the last month of treatment. Additional exploratory parameters, including levels of fibroblast growth factor 23 (FGF-23), serum bone-specific alkaline phosphatase (BAP), serum C-terminal telopeptide of type 1 collagen (CTx), serum procollagen type 1 N-terminal propeptide (P1NP), T50 calcification propensity score, other bone markers, and immune function, are also monitored.

A majority of the subjects exhibit a mean decrease in serum iPTH of between 30% and 50% from pre-treatment baseline during the last 6 weeks of treatment (weeks 47-52). After 12 weeks of treatment, steady-state conditions are nearly reached (median time to reach steady state is approximately 16 weeks), with subjects treated with the extended release formulation of 25-hydroxyvitamin $D_3$ exhibiting a serum 25-hydroxyvitamin $D_3$ concentration between about 50 ng/mL and about 90 ng/mL for the group treated with 300 mcg/week, between about 120 ng/mL and about 160 ng/mL for the group treated with 600 mcg/week, and between about 150 ng/mL and about 200 ng/mL for the group treated with 900 mcg/week.

Example 4

Safely Raising Serum 1,25-Dihydroxyvitamin D to Supraphysiologic Levels

Figure 8:
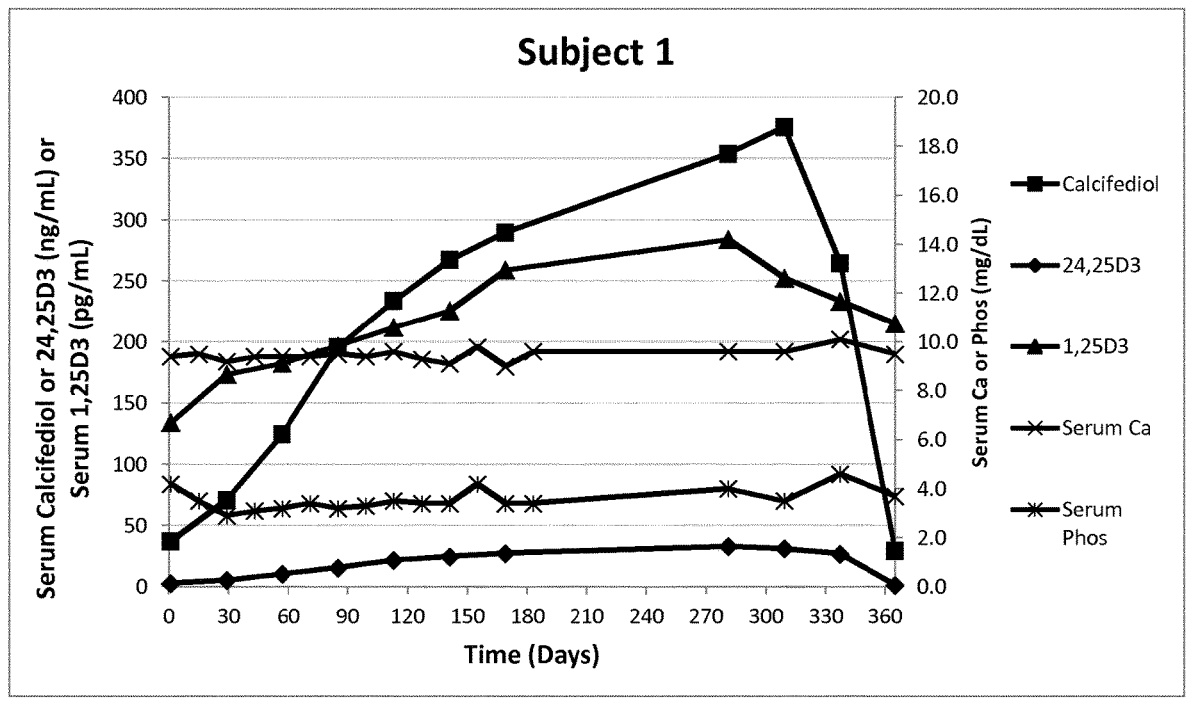
FIGS. 8 and 9 show serum calcifediol, serum calcitriol, serum calcium, serum phosphorous, and serum 24,25-dihydroxyvitamin $D_3$ values resulting from dosing subjects with increasing doses of extended-release, oral calcifediol over a period of up to one year.
Figure 9:
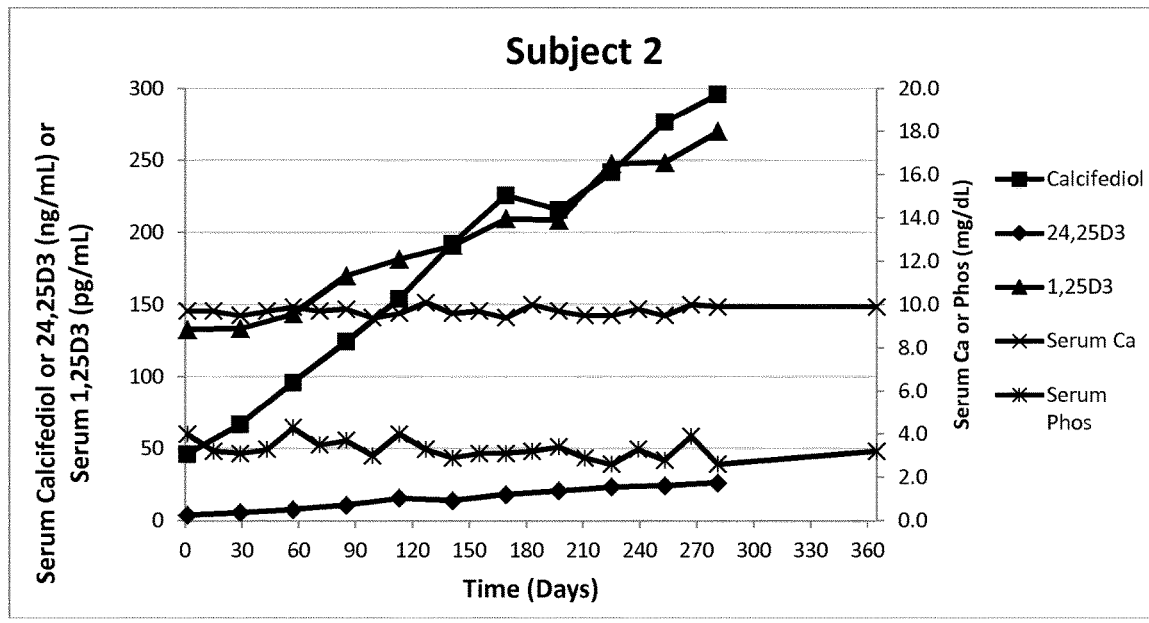

FIGS. 8 and 9 show early results, in two subjects, from a trial involving dosing subjects with extended-release, oral calcifediol over a period of up to one year.

The following protocol was applied. Subjects were to receive extended-release, oral calcifediol capsules at an initial daily dose of 30 micrograms, for four weeks, dosed at bedtime. Following the initial dose, the daily dose was allowed to be increased in 30 microgram increments at four-week intervals, to a maximum of 300 micrograms per day. During the dose escalation, if serum calcium was greater than 10.3 mg/dL for two consecutive visits then dosing was to be discontinued until serum calcium was 10.0 mg/dL or lower, at which time the subject was to recommense dosing at a dose of 30 micrograms lower than the previous dose, and to remain at that dosing level for twelve weeks. Dosing was to be stopped if serum calcium was greater than 10.3 mg/dL for a third time.

The subjects in the trial had advanced breast or prostate carcinomas with metastases to bone, and were receiving ongoing therapy with denosumab or zolendronic acid. Subjects had initial serum calcium less than 9.8 mg/dL and plasma iPTH of greater than 70 pg/mL.

FIGS. 8 and 9 show that serum calcifediol levels in these subjects rose to about 300 ng/ml or greater, while serum calcitriol levels rose to greater than 250 pg/mL. Serum calcium and serum phosphate levels were generally flat. The ratio of 25-hydroxyvitamin $D_3$ to serum 24,25-dihydroxyvitamin $D_3$ in these subjects was less than 20 and was generally about 10:1 or less.

The foregoing description is given for clearness of understanding only, and no unnecessary limitations should be understood therefrom, as modifications within the scope of the invention may be apparent to those having ordinary skill in the art. Throughout this specification and the claims which follow, unless the context requires otherwise, the word "comprise" and variations such as "comprises" and "comprising" will be understood to imply the inclusion of a stated integer or step or group of integers or steps but not the exclusion of any other integer or step or group of integers or steps.

Throughout the specification, where compositions are described as including components or materials, it is contemplated that the compositions can also consist essentially of, or consist of, any combination of the recited components or materials, unless described otherwise. Likewise, where methods are described as including particular steps, it is contemplated that the methods can also consist essentially of, or consist of, any combination of the recited steps, unless described otherwise. The invention illustratively disclosed herein suitably may be practiced in the absence of any element or step which is not specifically disclosed herein.

The practice of a method disclosed herein, and individual steps thereof, can be performed manually and/or with the aid of electronic equipment. Although processes have been described with reference to particular embodiments, a person of ordinary skill in the art will readily appreciate that other ways of performing the acts associated with the methods may be used. For example, the order of the various steps may be changed without departing from the scope or spirit of the method, unless described otherwise. In addition, some of the individual steps can be combined, omitted, or further subdivided into additional steps.

All patents, publications and references cited herein are hereby fully incorporated by reference. In case of conflict between the present disclosure and incorporated patents, publications and references, the present disclosure should control.

What is claimed:

1. A method of treating a patient with Chronic Kidney Disease Stage 5 and having secondary hyperparathyroidism and vitamin D insufficiency, wherein the patient is undergoing hemodialysis three times per week, comprising administering to the patient an extended release formulation of 25-hydroxyvitamin $D_3$ at a dose of 300-900 mcg per week divided into two or three doses per week.

2. The method of claim 1, wherein the patient has a serum iPTH level ≥150 pg/mL and <600 pg/mL.

3. The method of claim 1, wherein the patient has a serum iPTH level ≥400 pg/mL and <900 pg/mL.

4. The method of claim 1, comprising administering to the patient the extended release formulation of 25-hydroxyvitamin $D_3$ at a dose of 600 mcg per week.

5. The method of claim 1, comprising administering to the patient the extended release formulation of 25-hydroxyvitamin $D_3$ at a dose of 900 mcg per week.

6. The method of claim 1, comprising administering to the patient the extended release formulation of 25-hydroxyvitamin $D_3$ to raise the patient's serum 25-hydroxyvitamin $D_3$ level to at least 50 ng/mL.

7. The method of claim 6, comprising administering to the patient the extended release formulation of 25-hydroxyvitamin $D_3$ to raise the patient's serum 25-hydroxyvitamin $D_3$ level to in a range of 50 ng/mL to 200 ng/mL.

8. The method of claim 1, wherein the treatment reduces the patient's serum iPTH level.

9. The method of claim 8, wherein the treatment reduces the patient's serum iPTH level by at least 30%.

10. The method of claim 1, wherein the 25-hydroxyvitamin $D_3$ is administered orally in capsule form.

11. The method of claim 1, wherein the extended release 25-hydroxyvitamin $D_3$ therapy does not increase the patient's serum calcium level.

12. The method of claim 1, wherein the extended release 25-hydroxyvitamin $D_3$ therapy does not increase the patient's serum phosphorous level.

13. A method of treating a patient with Chronic Kidney Disease Stage 5 and having secondary hyperparathyroidism and vitamin D insufficiency, wherein the patient is undergoing hemodialysis three times per week, comprising administering to the patient an extended release formulation of 25-hydroxyvitamin $D_3$ at a dose of 600 mcg to 900 mcg per week, divided into three doses per week.

14. The method of claim 13, wherein the patient's serum 25-hydroxyvitamin $D_3$ level is raised to in a range of 50 ng/mL to 200 ng/mL and the therapy does not increase the patient's serum calcium level and does not increase the patient's serum phosphorous level.

15. A method of treating a patient with Chronic Kidney Disease Stage 5 and having secondary hyperparathyroidism and vitamin D insufficiency, wherein the patient is undergoing hemodialysis three times per week, comprising orally administering to the patient an extended release formulation of 25-hydroxyvitamin $D_3$ at a dose of 600 mcg to 900 mcg per week, divided into three doses per week, and raise the patient's serum 25-hydroxyvitamin $D_3$ level to in a range of 50 ng/mL to 200 ng/mL wherein the therapy does not increase the patient's serum calcium level and does not increase the patient's serum phosphorous level.

* * * * *